(12) United States Patent
Cantor et al.

(10) Patent No.: US 8,197,817 B2
(45) Date of Patent: Jun. 12, 2012

(54) REGULATION OF MINK IN THYMOCYTES AND T LYMPHOCYTES

(75) Inventors: Harvey Cantor, Wellesley, MA (US); Nami McCarty, Houston, TX (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 878 days.

(21) Appl. No.: 11/792,790

(22) PCT Filed: Dec. 16, 2005

(86) PCT No.: PCT/US2005/045800
§ 371 (c)(1),
(2), (4) Date: Jan. 14, 2008

(87) PCT Pub. No.: WO2006/073760
PCT Pub. Date: Jul. 13, 2006

(65) Prior Publication Data
US 2008/0248054 A1    Oct. 9, 2008

Related U.S. Application Data

(60) Provisional application No. 60/637,142, filed on Dec. 17, 2004.

(51) Int. Cl.
*A61K 39/00* (2006.01)
*C12N 5/02* (2006.01)
*G01N 33/567* (2006.01)

(52) U.S. Cl. ............... 424/184.1; 435/375; 435/7.21

(58) Field of Classification Search ............... 424/184.1; 435/375, 7.21
See application file for complete search history.

(56) References Cited

U.S. PATENT DOCUMENTS

| 5,580,723 | A | 12/1996 | Wells et al. |
| 6,207,646 | B1 | 3/2001 | Krieg et al. |
| 7,265,214 | B2 * | 9/2007 | Luo et al. ............ 536/23.1 |

OTHER PUBLICATIONS

Alberola-Ila et al., Selective requirement for MAP kinase activation in thymocyte differentiation, *Nature* 373(6515):620-623 (1995).
Bäckström et al., Positive selection through a motif in the alphabeta T cell receptor, *Science* 281(5378):835-838 (1998).
Bommhardt et al., MEK activity regulates negative selection of immature cd4+cd8+ thymocytes, *J. Immunol.* 164:2326-2337 (2000).
Bouillet et al., BH3-only Bcl-2 family member Bim is required for apoptosis of autoreactive thymocytes, *Nature* 415(6874):922-926 (2002).
Buch et al., Failure of HY-specific thymocytes to escape negative selection by receptor editing, *Immunity* 16:707-718 (2002).
Carrasco et al., A role for the cytoplasmic tail of the pre-T cell receptor (TCR) α chain in promoting constitutive internalization and degradation of the pre-TCR, *J. Biol. Chem.* 278(16):14507-14513 (2003).
Cohen et al., CD4+ T-cells from mice immunized to syngeneic sarcomas recognize distinct, non-shared tumor antigens, *Cancer Res.* 54(4):1055-1058 (1994).
Dan et al., Molecular cloning of MINK, a novel member of mammalian GCK family kinases, which is up-regulated during postnatal mouse cerebral development, *FEBS Lett.* 469:19-23 (2000).
Davis, M., A new trigger for T cells, *Cell* 110:285-287 (2002).
Delgado et al., CD3δ couples T-cell receptor signalling to ERK activation and thymocyte positive selection, *Nature* 406:426-430 (2000).
Dykxhoorn et al., Killing the messenger: short RNAs that silence gene expression, *Nat. Rev. Mol. Cell Biol.* 4:457-467 (2003).
Fu et al., TNIK, a novel member of the germinal center kinase family that activates the c-Jun N-terminal kinase pathway and regulates the cytoskeleton, *J. Biol. Chem.* 274(43):30729-30737 (1999).
GenBank accession No. AB035697, downloaded Aug. 12, 2007.
GenBank accession No. AB041925, downloaded Aug. 12, 2007.
GenBank accession No. AY775058, downloaded Aug. 12, 2007.
GenBank accession No. BAA90752, downloaded Aug. 12, 2007.
GenBank accession No. BC052474, downloaded Aug. 12, 2007.
GenBank accession No. NM_015716, downloaded Aug. 12, 2007.
GenBank accession No. NM_153827, downloaded Aug. 12, 2007.
GenBank accession No. NM_170663, downloaded Aug. 12, 2007.
Gil et al., Recruitment of Nck by CD3ε reveals a ligand-induced conformational change essential for T cell receptor signaling and synapse formation, *Cell* 109:901-912 (2002).
Hailman et al., Immature CD4+CD8+ thymocytes form a multifocal immunological synapse with sustained tyrosine phosphorylation, *Immunity* 16:839-848 (2002).
Harada et al., Survival factor-induced extracellular signal-regulated kinase phosphorylates BIM, inhibiting its association with BAX and proapoptotic activity, *Proc. Nat'l. Acad. Sci. USA* 101(43):15313-15317 (2004).
Hu et al., Identification and functional characterization of a novel human Misshapen/Nck interacting kinase-related kinase, hMINKβ, *J. Biol. Chem.* 279(52):54387-54397 (2004) and 280(6):5128 (2005) (correndum).
Kiefer et al., HPK1, a hematopoietic protein kinase activating the SAPK/JNK pathway, *EMBO J.* 15(24):7013-7025 (1996). Kisielow et al., Positive selection of antigen-specific T cells in thymus by restricting MHC molecules, *Nature* 335(6192):730-733 (1988).
Krystal et al., The selective tyrosine kinase inhibitor STI571 inhibits small cell lung cancer growth, *Clin. Cancer Res.* 6:3319-3326 (2000).

(Continued)

*Primary Examiner* — Marcia S Noble
(74) *Attorney, Agent, or Firm* — Wolf, Greenfield & Sacks, P.C.

(57) ABSTRACT

The invention relates to compositions and methods used to assess and alter the expression and activity of MINK in cells of the immune system, particularly thymocytes and T lymphocytes. The methods and compositions are used in a variety of clinical applications including vaccination, treatment of cancer, infectious disease, allergy, and transplantation. Screening methods are provided to identify inhibitors of MINK and susceptibility to effects of under- or over-expression of MINK.

4 Claims, 23 Drawing Sheets

OTHER PUBLICATIONS

Lim et al., Identification of residues which regulate activity of the STE20-related kinase hMINK, *Biochem. Biophys. Res. Commun.* 300(3):694-698 (2003).

McCarty et al., Signaling by the kinase MINK is essential in the negative selection of autoreactive thymocytes, *Nat. Immunol.* 6(1):65-72 (2005) and 6(2):219 (2005) (corrigendum).

McCarty et al., Detailed analysis of gene expression during development of T cell lineages in the thymus, *Proc. Nat'l. Acad. Sci. USA* 101(25):9339-9344 (2004).

Mello et al., Revealing the world of RNA interference, *Nature* 431:338-342 (2004).

Neilson et al., Calcineurin B1 is essential for positive but not negative selection during thymocyte development, *Immunity* 20:255-266 (2004).

Poinat et al., A conserved interaction between β1 integrin/PAT-3 and Nck-interacting kinase/MIG-15 that mediates commissural axon navigation in *C. elegans*, *Curr. Biol.* 12:622-631 (2002).

Rincon et al., The JNK pathway regulates the in vivo deletion of immature CD4+CD8+ thymocytes, *J. Exp. Med.* 188(10):1817-1830 (1998).

Rincón et al., The JNK and P38 MAP kinase signaling pathways in T cell-mediated immune responses, *Free Radic. Biol. Med.* 28(9):1328-1337 (2000).

Rubinson et al., A lentivirus-based system to functionally silence genes in primary mammalian cells, stem cells and transgenic mice by RNA interference, *Nat. Genet.* 33(3):401-406 (2003).

Sabapathy et al., JNK2 is required for efficient T-cell activation and apoptosis but not for normal lymphocyte development, *Curr. Biol.* 9:116-125 (1999).

Sabapathy et al., c-Jun $NH_2$-terminal kinase (JNK)1 and JNK2 have similar and stage-dependent roles in regulating T cell apoptosis and proliferation, *J. Exp. Med.* 193(3):317-328 (2001).

Sainio et al., Antisense inhibition of low-affinity nerve growth factor receptor in kidney cultures: power and pitfalls, *Cell Mol. Neurobiol.* 14(5):439-457 (1994).

Strasser et al., The control of apoptosis in lymphocyte selection, *Immunol. Rev.* 193:82-92 (2003).

Su et al., NIK is a new Ste20-related kinase that binds NCK and MEKK1 and activates the SAPK/JNK cascade via a conserved regulatory domain, *The EMBO J.* 16(6):1279-1290 (1997).

Teh et al., Early deletion and late positive selection of T cells expressing a male-specific receptor in T-cell receptor transgenic mice, *Dev. Immunol.* 1(1):1-10.

Valitutti et al., Serial triggering of many T-cell receptors by a few peptide-MHC complexes, *Nature* 375(6527):148-151 (1995).

Verma et al., RNA-mediated gene silencing: mechanisms and its therapeutic applications, *J. Clin. Pharm Ther.* 29:395-404 (2004).

Werlen et al., A motif in the αβ T-cell receptor controls positive selection by modulating ERK activity, *Nature* 406:422-426 (2000).

Yang et al., An SH3-binding site conserved in Bruton's tyrosine kinase and related tyrosine kinases mediates specific protein interactions in vitro and in vivo, *J. Biol. Chem.* 270(35):20832-20840 (1995).

Yao et al., A novel human STE20-related protein kinase, HGK, that specifically activates the c-Jun N-terminal kinase signaling pathway, *J. Biol. Chem.* 274(4):2118-2125 (1999).

Zhan et al., Without peripheral interference, thymic deletion is mediated in a cohort of double-positive cells without classical activation, *Proc. Nat'l. Acad. Sci. USA* 100(3):1197-1202 (2003).

GENBANK Submission; NIH/NCBI, Accession No. AAH52474 ; Strausberg et al.; Oct. 7, 2003, 3 pages.

GENBANK Submission; NIH/NCBI, Accession No. AAV41830; Hu et al.; Dec. 20, 2004, 2 pages.

GENBANK Submission; NIH/NCBI, Accession No. AB070507; Watanabe et al.; Jul. 3, 2002, 2 pages.

GENBANK Submission; NIH/NCBI, Accession No. BAA94837; Dan et al.; Aug. 22, 2000, 2 pages.

GENBANK Submission; NIH/NCBI, Accession No. NP_056531; Olsen et al.; Oct. 5, 2003, 3 pages.

GENBANK Submission; NIH/NCBI, Accession No. NP_722549; Olsen et al.; Oct. 5, 2003, 3 pages.

GENBANK Submission; NIH/NCBI, Accession No. NP_733763; Olsen et al.; Oct. 5, 2003, 3 pages.

Akashi et al., Two distinct pathways of positive selection for thymocytes. Proc. Natl Acad Sci U S A. Mar. 3, 1998;95(5):2486-91.

Ali et al., Differential regulation of peripheral CD4+ T cell tolerance induced by deletion and TCR revision. J Immunol. Dec. 1, 2003;171(11):6290-6.

Baribaud et al., Identification of key amino acids of the mouse mammary tumor virus superantigen involved in the specific interaction with T-cell receptor V(beta) domains. J Virol. Aug. 2001;75(16):7453-61.

Behrens et al., Jun N-terminal kinase 2 modulates thymocyte apoptosis and T cell activation through c-Jun and nuclear factor of activated T cell (NF-AT) Proc Natl Acad Sci U S A. Feb. 13, 2001;98(4):1769-74.

Dan et al., The Ste20 group kinases as regulators of MAP kinase cascades. Trends Cell Biol. May 2001;11(5):220-30.

Davis, Signal transduction by the JNK group of MAP kinases. Cell. Oct. 13, 2000;103(2):239-52.

Dong et al., Signaling by the JNK group of MAP kinases c-jun N-terminal Kinase. J Clin Immunol. Jul. 2001;21(4):253-7. Review.

Fanger et al., MEKKs, GCKs, MLKs, PAKs, TAKs, and tpls: upstream regulators of the c-Jun amino-terminal kinases? Curr Opin Genet Dev. Feb. 1997;7(1):67-74.

Harris et al., BH3-only Bcl-2 family members are coordinately regulated by the JNK pathway and require Bax to induce apoptosis in neurons. J Biol Chem. Oct. 12, 2001;276(41):37754-60. Epub Aug. 8, 2001.

Kunkel, Rapid and efficient site-specific mutagenesis without phenotype selection. Proc Natl Acad Sci U S A. 1985;82(2):488-92.

Lei et al., The Bax subfamily of Bcl2-related proteins is essential for apoptotic signal transduction by c-Jun NH(2)-terminal kinase. Mol Cell Biol. Jul. 2002;22(13):4929-42.

McCarty, The Nck SH2/SH3 adaptor protein: a regulator of multiple intracellular signal transduction events. Bioessays. Nov. 1998;20(11):913-21.

Ninomiya-Tsuji et al. The kinase TAK1 can activate the NIK-1 kappaB as well as the MAP kinase cascade in the IL-1 signalling pathway. Nature. Mar. 18, 1999;398(6724):252-6.

Putcha et al. Induction of BIM, a proapoptotic BH3-only BCL-2 family member, is critical for neuronal apoptosis. Neuron. Mar. 2001;29(3):615-28.

Singer, New perspectives on a development dilemma: the kinetic signaling model and the importance of signal duration for the CD4/CD8 lineage decision. Curr Opin Immunol. Apr. 2002;14(2):207-15.

Svensson et al., Involvement of CCR9 at multiple stages of adult T lymphopoiesis. J Leukoc Biol. Jan. 2008;83(1):156-64. Epub Oct. 2, 2007.

Whitfield et al., Dominant-negative c-Jun promotes neuronal survival by reducing BIM expression and inhibiting mitochondrial cyctochrome c release. Neuron. Mar. 2001:29(3):629-43.

* cited by examiner

FIG. 1
Comparison of MINK Isoforms

```
BAA90752    mouse  (SEQ ID NO:7)
NP_722549   human  (SEQ ID NO:8)
AAV41830    human  (SEQ ID NO:9)
NP_733763   human  (SEQ ID NO:10)
NP_056531   human  (SEQ ID NO:11)

BAA90752    MGDPAPARSLDDIDLSALRDPAGIFELVEVVGNGTYGQVYKGRHVKTGQLAAIKVMDVTE   60
NP_722549   MGDPAPARSLDDIDLSALRDPAGIFELVEVVGNGTYGQVYKGRHVKTGQLAAIKVMDVTE   60
AAV41830    MGDPAPARSLDDIDLSALRDPAGIFELVEVVGNGTYGQVYKGRHVKTGQLAAIKVMDVTE   60
NP_733763   MGDPAPARSLDDIDLSALRDPAGIFELVEVVGNGTYGQVYKGRHVKTGQLAAIKVMDVTE   60
NP_056531   MGDPAPARSLDDIDLSALRDPAGIFELVEVVGNGTYGQVYKGRHVKTGQLAAIKVMDVTE   60

BAA90752    DEEEEIKQEINMLKKYSHHRNIATYYGAFIKKSPPGNDDQLWLVMEFCGAGSVTDLVKNT  120
NP_722549   DEEEEIKQEINMLKKYSHHRNIATYYGAFIKKSPPGNDDQLWLVMEFCGAGSVTDLVKNT  120
AAV41830    DEEEEIKQEINMLKKYSHHRNIATYYGAFIKKSPPGNDDQLWLVMEFCGAGSVTDLVKNT  120
NP_733763   DEEEEIKQEINMLKKYSHHRNIATYYGAFIKKSPPGNDDQLWLVMEFCGAGSVTDLVKNT  120
NP_056531   DEEEEIKQEINMLKKYSHHRNIATYYGAFIKKSPPGNDDQLWLVMEFCGAGSVTDLVKNT  120

BAA90752    KGNALKEDCIAYICREILRGLAHLHAHKVIHRDIKGQNVLLTENAEVKLVDFGVSAQLDR  180
NP_722549   KGNALKEDCIAYICREILRGLAHLHAHKVIHRDIKGQNVLLTENAEVKLVDFGVSAQLDR  180
AAV41830    KGNALKEDCIAYICREILRGLAHLHAHKVIHRDIKGQNVLLTENAEVKLVDFGVSAQLDR  180
NP_733763   KGNALKEDCIAYICREILRGLAHLHAHKVIHRDIKGQNVLLTENAEVKLVDFGVSAQLDR  180
NP_056531   KGNALKEDCIAYICREILRGLAHLHAHKVIHRDIKGQNVLLTENAEVKLVDFGVSAQLDR  180
```

| | | |
|---|---|---|
| BAA90752 | TVGRRNTFIGTPYWMAPEVIACDENPDATYDYRSDIWSLGITAIEMAEGAPPLCDMHPMR | 240 |
| NP_722549 | TVGRRNTFIGTPYWMAPEVIACDENPDATYDYRSDIWSLGITAIEMAEGAPPLCDMHPMR | 240 |
| AAV41830 | TVGRRNTFIGTPYWMAPEVIACDENPDATYDYRSDIWSLGITAIEMAEGAPPLCDMHPMR | 240 |
| NP_733763 | TVGRRNTFIGTPYWMAPEVIACDENPDATYDYRSDIWSLGITAIEMAEGAPPLCDMHPMR | 240 |
| NP_056531 | TVGRRNTFIGTPYWMAPEVIACDENPDATYDYRSDIWSLGITAIEMAEGAPPLCDMHPMR | 240 |
| BAA90752 | ALFLIPRNPPPPRLKSKKKWSKKFIDFIDTCLIKTYLSRPPTEQLLKFPFIRDQPTERQVRI | 300 |
| NP_722549 | ALFLIPRNPPPPRLKSKKKWSKKFIDFIDTCLIKTYLSRPPTEQLLKFPFIRDQPTERQVRI | 300 |
| AAV41830 | ALFLIPRNPPPPRLKSKKKWSKKFIDFIDTCLIKTYLSRPPTEQLLKFPFIRDQPTERQVRI | 300 |
| NP_733763 | ALFLIPRNPPPPRLKSKKKWSKKFIDFIDTCLIKTYLSRPPTEQLLKFPFIRDQPTERQVRI | 300 |
| NP_056531 | ALFLIPRNPPPPRLKSKKKWSKKFIDFIDTCLIKTYLSRPPTEQLLKFPFIRDQPTERQVRI | 300 |
| BAA90752 | QLKDHIDRSRKKRGEKEETEYEYSGSEEDDSHGEEGEPSSIMNVPGESTLRREFLRLQQ | 360 |
| NP_722549 | QLKDHIDRSRKKRGEKEETEYEYSGSEEDDSHGEEGEPSSIMNVPGESTLRREFLRLQQ | 360 |
| AAV41830 | QLKDHIDRSRKKRGEKEETEYEYSGSEEDDSHGEEGEPSSIMNVPGESTLRREFLRLQQ | 360 |
| NP_733763 | QLKDHIDRSRKKRGEKEETEYEYSGSEEDDSHGEEGEPSSIMNVPGESTLRREFLRLQQ | 360 |
| NP_056531 | QLKDHIDRSRKKRGEKEETEYEYSGSEEDDSHGEEGEPSSIMNVPGESTLRREFLRLQQ | 360 |
| BAA90752 | ENKSNSEALKQQQQLQQQQQRDPEAHIKHLLHQRQRRIEEQKEERRVEEQQRREREQRK | 420 |
| NP_722549 | ENKSNSEALKQQQQLQQQQQRDPEAHIKHLLHQRQRRIEEQKEERRVEEQQRREREQRK | 420 |
| AAV41830 | ENKSNSEALKQQQQLQQQQQRDPEAHIKHLLHQRQRRIEEQKEERRVEEQQRREREQRK | 420 |
| NP_733763 | ENKSNSEALKQQQQLQQQQQRDPEAHIKHLLHQRQRRIEEQKEERRVEEQQRREREQRK | 420 |
| NP_056531 | ENKSNSEALKQQQQLQQQQQRDPEAHIKHLLHQRQRRIEEQKEERRVEEQQRREREQRK | 420 |

Fig. 1 (cont.)

| | | |
|---|---|---|
| BAA90752 | LQEKEQQRRLEDMQALRREEERRQAEREQEYKRKQLEEQRQSERLQRQLQQEHAYLKSLQ | 480 |
| NP_722549 | LQEKEQQRRLEDMQALRREEERRQAEREQEYKRKQLEEQRQSERLQRQLQQEHAYLKSLQ | 480 |
| AAV41830 | LQEKEQQRRLEDMQALRREEERRQAEREQEYKRKQLEEQRQSERLQRQLQQEHAYLKSLQ | 480 |
| NP_733763 | LQEKEQQRRLEDMQALRREEERRQAEREQEYKRKQLEEQRQSERLQRQLQQEHAYLKSLQ | 480 |
| NP_056531 | LQEKEQQRRLEDMQALRREEERRQAEREQEYKRKQLEEQRQSERLQRQLQQEHAYLKSLQ | 480 |
| BAA90752 | QQQQQQQQLQKQQQQQQQILLPGDRKPLYHYGRGINPADKPAWAREVEERARMNKQQNSPLA | 540 |
| NP_722549 | QQQQQQQQLQKQQQQQ..LLPGDRKPLYHYGRGMNPADKPAWAREVEERTRMNKQQNSPLA | 538 |
| AAV41830 | QQQQQQQQLQKQQQQQ..LLPGDRKPLYHYGRGMNPADKPAWAREVEERTRMNKQQNSPLA | 538 |
| NP_733763 | QQQQQQQQLQKQQQQQ..LLPGDRKPLYHYGRGMNPADKPAWAREVEERTRMNKQQNSPLA | 538 |
| NP_056531 | QQQQQQQQLQKQQQQQ..LLPGDRKPLYHYGRGMNPADKPAWAREVEERTRMNKQQNSPLA | 538 |
| BAA90752 | KRSQAGAGPEPPISQASPSPPGPLSQTPPMQRPVEPQEGPHKSLVAHRVPLKPYAAPVPR | 600 |
| NP_722549 | KSKPGSTGPEPPIPQASPGPPGPLSQTPPMQRPVEPQEGPHKSLVAHRVPLKPYAAPVPR | 598 |
| AAV41830 | KSKPGSTGPEPPIPQASPGPPGPLSQTPPMQRPVEPQEGPHKSL........ | 582 |
| NP_733763 | KSKPGSTGPEPPIPQASPGPPGPLSQTPPMQRPVEPQEGPHKSLVAHRVPLKPYAAPVPR | 598 |
| NP_056531 | KSKPGSTGPEPPIPQASPGPPGPLSQTPPMQRPVEPQEGPHKSLVAHRVPLKPYAAPVPR | 598 |
| BAA90752 | SQSLQDQPTRNLAAFPASHDPDPAAVPTPTATPSARGAVIRQNSDPTSEGPGPSPNPPSW | 660 |
| NP_722549 | SQSLQDQPTRNLAAFPASHDPDPA.IPAPTATPSARGAVIRQNSDPTSEGPGPSPNPPAW | 657 |
| AAV41830 | ...QDQPTRNLAAFPASHDPDPA.IPAPTATPSARGAVIRQNSDPTSEGPGPSPNPPAW | 637 |
| NP_733763 | SQSLQDQPTRNLAAFPASHDPDPA.IPAPTATPSARGAVIRQNSDPTSEGPGPSPNPPAW | 657 |
| NP_056531 | SQSLQDQPTRNLAAFPASHDPDPA.IPAPTATPSARGAVIRQNSDPTSEGPGPSPNPPAW | 657 |

Fig. 1 (cont.)

```
BAA90752    VRPDNEAPPKVPQRTSSIATALNTSGAGGSRPAQAVRA..........................  698
NP_722549   VRPDNEAPPKVPQRTSSIATALNTSGAGGSRPAQAVRARPRSNSAWQIYLQRRAERGTPK  717
AAV41830    VRPDNEAPPKVPQRTSSIATALNTSGAGGSRPAQAVRARPRSNSAWQIYLQRRAERGTPK  697
NP_733763   VRPDNEAPPKVPQRTSSIATALNTSGAGGSRPAQAVRA..........................  695
NP_056531   VRPDNEAPPKVPQRTSSIATALNTSGAGGSRPAQAVRA..........................  695

BAA90752    ............SNPDLRRSDPGWERSDSVLPASHGHLPQAGSLERNRNRVGASTKL  743
NP_722549   PPGPPAQPPGPPNASSNPDLRRSDPGWERSDSVLPASHGHLPQAGSLERNR..VGVSSKP  775
AAV41830    PPGPPAQPPGPPNASSNPDLRRSDPGWERSDSVLPASHGHLPQAGSLERNR..VGASSKL  755
NP_733763   ............SNPDLRRSDPGWERSDSVLPASHGHLPQAGSLERNR..VGVSSKP  738
NP_056531   ............SNPDLRRSDPGWERSDSVLPASHGHLPQAGSLERNR..VGVSSKP  738

BAA90752    DSSPVLSPGNKAKPEDHRSRPGRPA.........DFVLLKERTLDEAPKPPKKAMDYSSSS  795
NP_722549   DSSPVLSPGNKAKPDDHRSRPGRPA.........DFVLLKERTLDEAPRPPKKAMDYSSSS  827
AAV41830    DSSPVLSPGNKAKPDDHRSRPGRPA.........DFVLLKERTLDEAPRPPKKAMDYSSSS  807
NP_733763   DSSPVLSPGNKAKPDDHRSRPGRPASYKRAIGEDFVLLKERTLDEAPRPPKKAMDYSSSS  798
NP_056531   DSSPVLSPGNKAKPDDHRSRPGRPA.........DFVLLKERTLDEAPRPPKKAMDYSSSS  790

BAA90752    EEVESSEEEEEGDGEPSEGSRDTPGGRSDGDTDSVTTMVVHDVEEISGTQPSYGGGTMV  855
NP_722549   EEVESSEDDEEEGEGEGGPAEGSRDTPGGRSDGDTDSVSTMVVHDVEEITGTQPPYGGGTMV  887
AAV41830    EEVESSEDDEEEGEGEGGPAEGSRDTPGGRSDGDTDSVSTMVVHDVEEITGTQPPYGGGTMV  867
NP_733763   EEVESSEDDEEEGEGEGGPAEGSRDTPGGRSDGDTDSVSTMVVHDVEEITGTQPPYGGGTMV  858
NP_056531   EEVESSEDDEEEGEGEGGPAEGSRDTPGGRSDGDTDSVSTMVVHDVEEITGTQPPYGGGTMV  850
```

Fig. 1 (cont.)

| | | |
|---|---|---|
| BAA90752 | VQRTPEEERSLLLADSNGYTNLPDVVQPSHSPTENSKGQSPPTKDGGSDYQSRGLVKAPG | 915 |
| NP_722549 | VQRTPEEERNLLHADSNGYTNLPDVVQPSHSPTENSKGQSPPSKGSPPSKDGSGDYQSRGLVKAPG | 947 |
| AAV41830 | VQRTPEEERNLLHADSNGYTNLPDVVQPSHSPTENSKGQSPPSKGSPPSKDGSGDYQSRGLVKAPG | 927 |
| NP_733763 | VQRTPEEERNLLHADSNGYTNLPDVVQPSHSPTENSKGQSPPSKDGSGDYQSRGLVKAPG | 918 |
| NP_056531 | VQRTPEEERNLLHADSNGYTNLPDVVQPSHSPTENSKGQSPPSKDGSGDYQSRGLVKAPG | 910 |
| | | |
| BAA90752 | KSSFTMFVDLGIYQPGGSGDTIPITALVGGEGGRLDQLQFDVRKGSVVNVNPTNTRAHSE | 975 |
| NP_722549 | KSSFTMFVDLGIYQPGGSGDSIPITALVGGEGTRLDQLQYDVRKGSVVNVNPTNTRAHSE | 1007 |
| AAV41830 | KSSFTMFVDLGIYQPGGSGDSIPITALVGGEGTRLDQLQYDVRKGSVVNVNPTNTRAHSE | 987 |
| NP_733763 | KSSFTMFVDLGIYQPGGSGDSIPITALVGGEGTRLDQLQYDVRKGSVVNVNPTNTRAHSE | 978 |
| NP_056531 | KSSFTMFVDLGIYQPGGSGDSIPITALVGGEGTRLDQLQYDVRKGSVVNVNPTNTRAHSE | 970 |
| | | |
| BAA90752 | TPEIRKYKKRFNSEILCAALWGVNLLLVGTENGLMLLDRSGQGKVYGLIGRRRFQQMDVLE | 1035 |
| NP_722549 | TPEIRKYKKRFNSEILCAALWGVNLLLVGTENGLMLLDRSGQGKVYGLIGRRRFQQMDVLE | 1067 |
| AAV41830 | TPEIRKYKKRFNSEILCAALWGVNLLLVGTENGLMLLDRSGQGKVYGLIGRRRFQQMDVLE | 1047 |
| NP_733763 | TPEIRKYKKRFNSEILCAALWGVNLLLVGTENGLMLLDRSGQGKVYGLIGRRRFQQMDVLE | 1038 |
| NP_056531 | TPEIRKYKKRFNSEILCAALWGVNLLLVGTENGLMLLDRSGQGKVYGLIGRRRFQQMDVLE | 1030 |
| | | |
| BAA90752 | GLNLLITISGKRNKLRVYYLSWLRNKILHNDPEVEKKQGWTTVGDMEGCGHYRVVKYERI | 1095 |
| NP_722549 | GLNLLITISGKRNKLRVYYLSWLRNKILHNDPEVEKKQGWTTVGDMEGCGHYRVVKYERI | 1127 |
| AAV41830 | GLNLLITISGKRNKLRVYYLSWLRNKILHNDPEVEKKQGWTTVGDMEGCGHYRVVKYERI | 1107 |
| NP_733763 | GLNLLITISGKRNKLRVYYLSWLRNKILHNDPEVEKKQGWTTVGDMEGCGHYRVVKYERI | 1098 |
| NP_056531 | GLNLLITISGKRNKLRVYYLSWLRNKILHNDPEVEKKQGWTTVGDMEGCGHYRVVKYERI | 1090 |

Fig. 1 (cont.)

| | | |
|---|---|---|
| BAA90752 | KFLVIALKNSVEVYAWAPKPYHKFMAFKSFADLPHRPLLVDLTVEEGQRLKVIYGSSAGF | 1155 |
| NP_722549 | KFLVIALKSSVEVYAWAPKPYHKFMAFKSFADLPHRPLLVDLTVEEGQRLKVIYGSSAGF | 1187 |
| AAV41830 | KFLVIALKSSVEVYAWAPKPYHKFMAFKSFADLPHRPLLVDLTVEEGQRLKVIYGSSAGF | 1167 |
| NP_733763 | KFLVIALKSSVEVYAWAPKPYHKFMAFKSFADLPHRPLLVDLTVEEGQRLKVIYGSSAGF | 1158 |
| NP_056531 | KFLVIALKSSVEVYAWAPKPYHKFMAFKSFADLPHRPLLVDLTVEEGQRLKVIYGSSAGF | 1150 |
| | | |
| BAA90752 | HAVDVDSGNSYDIYIPVHIQSQITPHAIIFLPNTDGMEMLLCYEDEGVYVNTYGRIIKDV | 1215 |
| NP_722549 | HAVDVDSGNSYDIYIPVHIQSQITPHAIIFLPNTDGMEMLLCYEDEGVYVNTYGRIIKDV | 1247 |
| AAV41830 | HAVDVDSGNSYDIYIPVHIQSQITPHAIIFLPNTDGMEMLLCYEDEGVYVNTYGRIIKDV | 1227 |
| NP_733763 | HAVDVDSGNSYDIYIPVHIQSQITPHAIIFLPNTDGMEMLLCYEDEGVYVNTYGRIIKDV | 1218 |
| NP_056531 | HAVDVDSGNSYDIYIPVHIQSQITPHAIIFLPNTDGMEMLLCYEDEGVYVNTYGRIIKDV | 1210 |
| | | |
| BAA90752 | VLQWGEMPTSVAYICSNQIMGWGEKAIEIRSVETGHLDGVFMHKRAQRLKFLCERNDKVF | 1275 |
| NP_722549 | VLQWGEMPTSVAYICSNQIMGWGEKAIEIRSVETGHLDGVFMHKRAQRLKFLCERNDKVF | 1307 |
| AAV41830 | VLQWGEMPTSVAYICSNQIMGWGEKAIEIRSVETGHLDGVFMHKRAQRLKFLCERNDKVF | 1287 |
| NP_733763 | VLQWGEMPTSVAYICSNQIMGWGEKAIEIRSVETGHLDGVFMHKRAQRLKFLCERNDKVF | 1278 |
| NP_056531 | VLQWGEMPTSVAYICSNQIMGWGEKAIEIRSVETGHLDGVFMHKRAQRLKFLCERNDKVF | 1270 |
| | | |
| BAA90752 | FASVRSGGSSQVYFMTLNRNCIMNW | 1300 |
| NP_722549 | FASVRSGGSSQVYFMTLNRNCIMNW | 1332 |
| AAV41830 | FASVRSGGSSQVYFMTLNRNCIMNW | 1312 |
| NP_733763 | FASVRSGGSSQVYFMTLNRNCIMNW | 1303 |
| NP_056531 | FASVRSGGSSQVYFMTLNRNCIMNW | 1295 |

Fig. 1 (cont.)

1. Control thymus
2. MINK thymus
3. Control spleen
4. MINK spleen

Random RNAi in lentivirus vector

REGULATION OF MINK IN THYMOCYTES AND T LYMPHOCYTES

FIELD OF THE INVENTION

The present invention relates generally to the field of immunology, more particularly to thymocyte and T cell apoptosis, and compositions and methods for use in the diagnosis and treatment of various diseases and conditions including autoimmunity, cancer, allergy, infectious disease, and transplantation.

BACKGROUND OF THE INVENTION

Thymocytes bearing T cell receptors (TCRs) that engage MHC self-peptide complexes with intermediate affinity are expanded in the thymus in a process called positive selection, whereas a subset that expresses high affinity receptors for self-peptides are eliminated through a process called negative selection. There is evidence that distinct TCR-linked signaling pathways culminate in these alternate fates. Engagement of the TCR by positive selecting ligands transmits calcineurin-dependent signals and activates the extracellular signal-regulated protein kinase (ERK) (Alberola-Ila J et al., 1995, *Nature* 373:620-3; Backstrom B T et al., 1998, *Science* 281:835-8; Werlen G et al., 2000, *Nature* 406:422-6; Delgado P et al., 2000, *Nature* 406:426-30; Hailman E et al., 2002, *Immunity* 16:839-48; Neilson J R et al., 2004, *Immunity* 20:255-66). In contrast, negative selection may depend on the action of Bim, a BH3—only proapoptotic Bcl-2 family member, which provokes downstream signals through Bax and Bak leading to cell death (Bouillet P et al., 2002, *Nature* 415:922-6; Strasser A et al., 2003, *Immunol Rev* 193:82-92). Although Jun kinase (JNK) has also been implicated in a TCR-signaling pathway that can lead to thymocyte apoptosis, the early signaling events that lead to negative selection have not previously been identified (Rincon M et al., 1998, *J Exp Med* 188:1817-30).

SUMMARY OF THE INVENTION

The invention in one aspect is a method for inhibiting negative selection of thymocytes in a mammal. The method according to this aspect of the invention includes the step of down-regulating MINK in thymocytes of the mammal.

In one aspect the invention is a method for inhibiting activation-induced cell death of T cells of a mammal. The method according to this aspect of the invention includes the step of down-regulating MINK in T cells of the mammal.

The invention in one aspect is a method for biasing an immune response away from a Th1 response in a subject. The method according to this aspect of the invention includes the step of administering to the subject an effective amount of a MINK inhibitor.

In one aspect the invention is a method for enhancing negative selection of thymocytes in a mammal. The method according to this aspect of the invention includes the step of up-regulating MINK in thymocytes of the mammal.

The invention in one aspect is a method for enhancing activation-induced cell death of T cells of a mammal. The method according to this aspect of the invention includes the step of up-regulating MINK in T cells of the mammal.

In one aspect the invention is a method for biasing an immune response toward a Th1 response in a subject. The method according to this aspect of the invention includes the step of administering to the subject an effective amount of a MINK activator.

The invention in one aspect is a method for vaccinating a subject. The method according to this aspect of the invention includes the steps of administering to the subject a vaccine comprising an antigen; and administering to the subject an effective amount of a MINK inhibitor.

In one aspect the invention is a method for treating a subject with cancer. The method according to this aspect of the invention includes the step of administering to the subject an effective amount of a MINK inhibitor.

The invention in one aspect is a method for treating a subject with an infectious disease. The method according to this aspect of the invention includes the step of administering to the subject an effective amount of a MINK inhibitor.

In one aspect the invention is a method for preparing bone marrow cells for a subject receiving a bone marrow autograft. The method according to this aspect of the invention includes the step of down-regulating MINK in autograft bone marrow cells.

The invention in one aspect is a preparation of bone marrow cells with reduced MINK.

In one aspect the invention is a method for treating a subject having autoimmune disease (AID). The method according to this aspect of the invention includes the step of administering to the subject an effective amount of a MINK activator.

The invention in one aspect is a method for treating a subject receiving an allograft. The method according to this aspect of the invention includes the step of administering to the subject an effective amount of a MINK activator.

In one aspect the invention is a method for treating a subject having allergy. The method according to this aspect of the invention includes the step of administering to the subject an effective amount of a MINK activator.

The invention in one aspect is a method for identifying a MINK-specific inhibitor. The method according to this aspect of the invention includes the steps of contacting a test population of T cells with a MINK activator and a test agent; measuring a test MINK activity (D) in the contacted test population of T cells; comparing the test MINK activity (D) to a first control MINK activity (A) in a first control population of T cells, said first control population of T cells not having MINK activity, wherein the first control population of T cells is contacted with the MINK activator; comparing the test MINK activity (D) to a second control MINK activity (B) in a second control population of T cells, said second control population of T cells having MINK activity, wherein the second control population of T cells is contacted with the MINK activator; and identifying the test agent as a MINK-specific inhibitor when $(D-A)/(B-A)$ is less than 1.

In one aspect the invention is a method for determining if a subject has impaired negative selection of developing thymocytes. The method according to this aspect of the invention includes the steps of isolating messenger RNA, cDNA, or genomic DNA from the subject; screening the messenger RNA, cDNA, or genomic DNA for a nucleic acid molecule encoding a mutant MINK; and determining the subject has impaired negative selection of developing thymocytes when the messenger RNA, cDNA, or genomic DNA comprises a nucleic acid molecule encoding a mutant MINK.

The invention in one aspect is a method for identifying a subject as susceptible to development of an autoimmune disease (AID). The method according to this aspect of the invention includes the steps of measuring MINK activity in a population of T cells of a test subject suspected of being susceptible to development of an AID; comparing the MINK activity in the population of T cells of the test subject to MINK activity in a population of T cells of a control subject; and identifying the test subject as susceptible to development of the AID when the MINK activity in the population of T cells of the control subject exceeds the MINK activity in the population of T cells of the test subject.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 1 is an alignment of amino acid sequences of murine MINK (SEQ ID NO:7) and four known human MINK isoforms (SEQ ID NOs:8, 9, 10, and 11). Highly conserved lysine K54 is shown in bold, and prolines P551, P657, and P764 in the murine MINK sequence are shown underlined.

DETAILED DESCRIPTION OF THE INVENTION

Figure 2A:
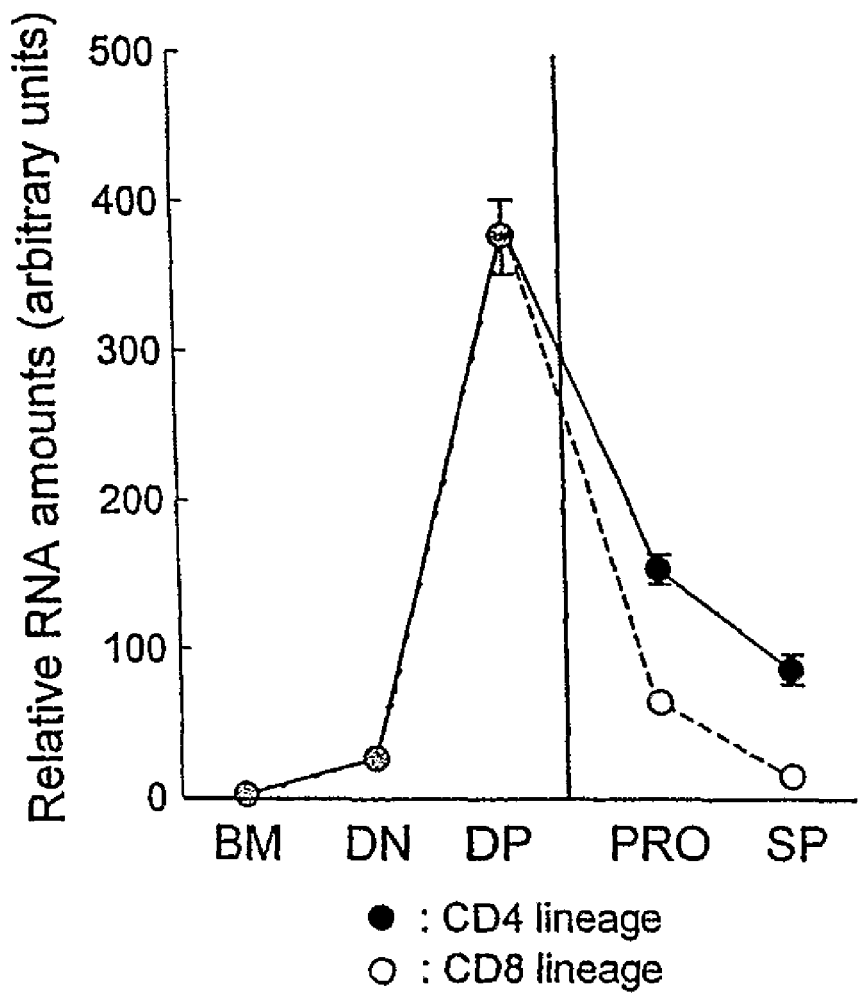
FIG. 2A shows a graph demonstrating MINK expression as measured by relative RNA levels (y-axis) in bone marrow and thymocyte subpopulations.

The invention is based in part on the discovery by the inventors that apoptosis in thymocytes and T cells involves signaling in those cells by MINK. More particularly, the invention is based in part on the discovery by the inventors that MINK expression is particularly high in double positive (DP; CD4+CD8+) thymocytes, and signaling by MINK is essential in negative selection of autoreactive thymocytes. In addition, the invention is based in part on the discovery by the inventors that MINK is normally upregulated in activated but not resting T cells and is involved in promoting activation-induced cell death (AICD) of certain T cells in the periphery. Overall, MINK is thus associated with deletion of thymocytes and certain activated T cells. The deletion of these thymocytes and certain activated T cells in the periphery is believed to promote a state of self tolerance. Conversely, MINK deficiency is thus associated with diminished deletion of thymocytes and certain activated T cells. The diminished deletion of these thymocytes and certain activated T cells in the periphery is believed to promote a state of immune reactivity toward self, i.e., autoimmunity.

The invention generally provides methods and compositions useful for manipulating and assessing MINK in thymocytes and T cells, both in vitro and in vivo. Methods and compositions of the invention generally will find use whenever it is desirable to increase or decrease negative selection and/or AICD. For example, the methods and compositions will find use in diagnosing and treating a variety of diseases and conditions, in which the immune system, particularly the adaptive immune system, is involved. These applications, diseases, and conditions include, without limitation, cancer, infectious disease, allergy, vaccination, autoimmunity, and transplantation. The invention also provides methods useful for identifying agents that can be used to alter MINK expression and activity in thymocytes and T cells.

A thymocyte is a precursor cell of a mature T lymphocyte present in the thymus. Thymocytes include double positive (DP) thymocytes, expressing both CD4 and CD8; single positive (SP) thymocytes, expressing CD4 or CD8; and double negative (DN) thymocytes, expressing neither CD4 nor CD8.

Negative selection is the process that eliminates developing lymphocytes whose antigen receptors bind strongly to self antigens present in generative lymphoid organs. With respect to developing T lymphocytes, the generative lymphoid organ is the thymus. Developing T lymphocytes, also called thymocytes, undergo positive and negative selection in the thymus upon their expression of antigen receptors. Positive selection ensures maturation of T lymphocytes with low avidity for self major histocompatibility complex (MHC), so that mature T cells will recognize foreign antigen presented in the context of self MHC. Negative selection deletes those clones of developing T cells that would otherwise be harmfully reactive with self antigens. The mechanism of negative selection is apoptosis, induced by antigen receptor-generated signals in the immature lymphocytes.

A T cell is a mature T lymphocyte found in the periphery, i.e., a circulating T cell. T cells include CD4+ T cells and CD8+ T cells. T cells mature from thymocytes in the thymus, circulate in the blood and lymph, populate secondary lymphoid tissues such as spleen and lymph nodes, and are recruited to peripheral sites of antigen exposure. T cells characteristically express clonally selected T cell antigen receptors (also called T cell receptors or TCR).

Activation-induced cell death (AICD) refers to a form of programmed cell death (apoptosis) of T cells that are repeatedly stimulated by antigen. AICD is believed to be transduced by signals from membrane death receptors including Fas. Signaling by Fas involves interaction with Fas ligand (FasL), leading eventually to activation of caspase-8 (and caspase-10 in humans) and activation of effector caspases (e.g., caspase-3 and caspase-6) to initiate DNA fragmentation and nuclear breakdown. AICD thus results in depletion in the periphery of T cells specific for antigen that, due to its persistence, repeatedly stimulates those cells. Such antigens are usually self antigens. Defective in vivo expression of Fas or of FasL results in autoimmunity.

Misshapen/NIKs-related kinase (MINK), also known as mitogen-activated protein kinase kinase kinase kinase 6, is a member of the germinal center family of kinases (GCKs) that are homologous to the yeast sterile 20 (Step 20) kinases. GCKs regulate a wide variety of cellular processes, including cell morphology, cytoskeletal rearrangement, and survival. The serine/threonine kinase MINK is closely related to Nck-interacting kinase (NIK) and binds to Nck protein in response to T-cell receptor (TCR) ligation. MINK activates both the JNK MAPK and p38 pathways. The cloning of MINK and its identification as novel GCK was first reported in 2000 (Dan I et al., 2000, *FEBS Lett* 469:19-23).

The human MINK gene is located on chromosome 17. A genomic DNA sequence that includes the last exon of MINK corresponds to GenBank accession no. AB070507. Since the cloning of human MINK in 2000 (Dan et al, 2000; GenBank accession no. NM_015716), three additional isoforms have been reported resulting from alternate splicing (GenBank accession nos. NM_170663, AY775058, and NM_153827). Human MINK isoform 1 and murine MINK share 97% amino acid sequence identity and all 32 exon/intron boundaries in CDS matched consensus sequences for splicing. FIG. 1 shows an alignment of a murine MINK and four isoforms of human MINK.

MINK is expressed in most tissues, with the highest abundance in brain, heart, kidney, and spleen (Dan I et al., 2000, *FEBS Lett* 469:19-23). The N-terminal catalytic domain of each of these shows 89% identity with that of NIK and TNIK at the amino acid level. At the C-terminus of MINK is a GCK homology domain sharing 88% amino acid identity with NIK and TNIK, respectively. GCK homology domains, also known as C-terminal citron homology (CNH) domains, are thought to be important for protein-protein interactions in the JNK pathway (Poinat et al., 2002, *Curr Biol* 12:622-31; Su et al., 1997, *EMBO J.* 16:1279-90). The intermediate region between these two domains shares less homology with the NIK-related kinases. However, there are several clusters of proline-rich motifs (PXXP) which are thought to be Src homology 3 (SH3)-binding domains. Proline-rich regions such as these are important for protein/protein binding interactions in several NIK subfamily members and thus may interact with the Nck adaptor protein through binding of proline-rich regions of MINK to SH3 domains of Nck.

Thymocytes bearing T cell receptors (TCRs) that engage MHC self-peptide complexes with intermediate affinity are expanded in the thymus in a process called positive selection, whereas a subset that expresses high affinity receptors for self-peptides are eliminated through a process called negative selection. There is evidence that distinct TCR-linked signaling pathways culminate in these alternate fates. Engagement of the TCR by positive selecting ligands transmits calcineurin-dependent signals and activates the extracellular signal-regulated protein kinase (ERK). In contrast, negative selection may depend on the action of Bim, a BH3-only proapoptotic Bcl-2 family member, which provokes downstream signals through Bax and Bak leading to cell death. Although Jun kinase (JNK) has also been implicated in a TCR-signaling is pathway that can lead to thymocyte apoptosis, the early signaling events that lead to negative selection have not previously been identified.

It has now been discovered according to the invention that MINK is an essential signaling element that couples the TCR to apoptotic pathways. More specifically, it has now been discovered according to the invention that MINK is an essential signaling element that couples the TCR to negative but not positive selection. It has also now been discovered according to the invention that in developing thymocytes, MINK expression increases 20-50 fold during the transition from DN thymocytes to DP thymocytes. It has also now been discovered according to the invention that in T cells, MINK is activated after ligation of a self-antigen to the T-cell receptor. MINK binds to the Nck adaptor protein and becomes phosphorylated at the receptor. MINK then activates the downstream pathway that leads to JNK activation and, ultimately, cell death. Analysis of this pathway suggests that an upstream interaction of MINK with the Nck adaptor protein may direct the flow of TCR-based signals towards Jun kinase activation and upregulation of Bim and BimEL proapoptotic protein.

The invention in certain aspects provides methods for inhibiting MINK. Inhibition of MINK refers to any process by which the expression and/or activity of MINK is reduced from a corresponding reference amount of MINK expression and/or activity. Inhibition of MINK is desirable whenever it is desirable to boost immune reactivity toward an antigen. Because MINK is involved in promoting negative selection of thymocytes and AICD of T cells in the periphery, inhibition of MINK is desirable whenever it is desirable to inhibit negative selection of thymocytes and/or AICD of T cells in the periphery. For example, inhibition of MINK is desirable when vaccinating a subject, treating a subject with cancer, treating a subject with an infectious disease, and preparing bone marrow cells for a subject receiving a bone marrow autograft. The methods for inhibiting MINK generally include contacting MINK-expressing cells such as thymocytes and T cells with an effective amount of a MINK inhibitor. MINK inhibitors as used herein generally include certain nucleic acid molecules specific for corresponding MINK nucleic acid molecules, as well as other types of MINK inhibitors.

The invention in certain aspects provides methods for increasing MINK. Increasing MINK refers to any process by which the expression and/or activity of MINK is increased from a corresponding reference amount of MINK expression and/or activity. Increasing MINK is desirable whenever it is desirable to reduce immune reactivity toward an antigen. Because MINK is involved in promoting negative selection of thymocytes and AICD of T cells in the periphery, increasing MINK is desirable whenever it is desirable to increase negative selection of thymocytes and/or AICD of T cells in the periphery. For example, increasing MINK is desirable when treating a subject with an autoimmune disease (AID), treating a subject receiving an allograft, treating a subject having allergy. The methods for increasing MINK generally include contacting MINK-expressing cells such as thymocytes and T cells with an effective amount of a MINK activator. MINK activators as used herein generally include certain nucleic acid molecules specifically encoding MINK or encoding gene activation sequences specific for MINK, as well as other types of MINK activators.

Certain aspects of the invention involve inhibition of MINK to modify basic elements in immunity. These aspects of the invention include methods for inhibiting negative selection of thymocytes, inhibiting AICD of T cells, and biasing an immune response away from a Th1 response.

In one aspect the invention provides a method for inhibiting negative selection of thymocytes in a mammal. The method according to this aspect of the invention includes the step of down-regulating MINK in thymocytes of the mammal. Down-regulating refers generally to inhibiting the expression and/or function of a particular biological molecule or process. In one embodiment down-regulating refers to eliminating the expression and/or function of a particular biological molecule or process. As used herein, down-regulating MINK thus refers to inhibiting the expression and/or function of MINK. In one embodiment down-regulating MINK refers to inhibiting expression of MINK protein. In one embodiment down-regulating MINK refers to inhibiting expression of a nucleic acid encoding MINK protein. In one embodiment down-regulating MINK refers to inhibiting the function of MINK protein, e.g., by inhibiting enzymatic activity of MINK, inhibiting interaction between MINK and at least one other protein, or inhibiting conformational changes of MINK.

Down-regulation of MINK can be assessed by direct measurement of reduced MINK expression or function, by measurement of reduced downstream signaling events in MINK signaling pathway, and by measurement of reduced downstream consequences of signaling by MINK, e.g., reduced negative selection and reduced AICD of T cells (see below).

In one embodiment according to this and other aspects of the invention, MINK is down-regulated by contacting thymocytes of the mammal with a MINK inhibitor. The contacting can be accomplished using any suitable method, including for example by administering the MINK inhibitor systemically or by administering the MINK inhibitor by direct injection into the thymus. As used herein a MINK inhibitor is an agent that specifically reduces expression and/or function of MINK. In one embodiment the MINK inhibitor is an agent that specifically reduces expression of MINK. In one embodiment the MINK inhibitor is an agent that specifically inhibits MINK function. In one embodiment the MINK inhibitor is an agent that specifically inhibits a conformation change in MINK.

As used herein MINK function and, equivalently, MINK activity refer to at least one function or activity of MINK. The function or activity can be a manifestation of ATP binding by MINK, MINK kinase activity, interaction of MINK proline-rich domain with another protein, interaction of the MINK GCK homology domain with another protein, and any combination thereof. Thus a MINK inhibitor includes an agent that specifically inhibits ATP binding by MINK, MINK kinase activity, interaction of MINK proline-rich domain with another protein, interaction of the MINK GCK homology domain with another protein, and any combination thereof.

MINK activity can be reduced in the cell by disrupting its ability to bind to other proteins or by disrupting its kinase activity. In one embodiment, the MINK mutation is a point mutation in the kinase domain resulting in the substitution of one amino acid for another in the sequence of MINK. Amino acid residue changes which confer altered properties include changes in (1) active site residues involved in substrate binding or catalytic events or the internal surface of the active site cavity, (2) residues lining the entrance to the active site which exert electrostatic or steric influence on substrate binding or product release, or (3) residues that confer structure to the active site activity or entrance such that the ability of MINK to engage substrate is altered. Such substitutions can be made by a variety of methods known to one of ordinary skill in the art. For example, amino acid substitutions may be made by PCR-directed mutation, site-directed mutagenesis according to the method of Kunkel (Kunkel, 1985, *Proc Natl Acad Sci USA* 82:488-92), or by chemical synthesis of a gene encoding MINK.

In one embodiment MINK activity can be reduced by eliminating or replacing with another amino acid the highly conserved lysine residue K54 that binds ATP.

In one embodiment according to this and other aspects of the invention, the MINK inhibitor includes a nucleic acid molecule encoding a dominant negative mutant MINK. In one embodiment according to this and other aspects of the invention, the MINK inhibitor is a nucleic acid molecule encoding a dominant negative mutant MINK. A dominant negative mutant MINK is an inactive variant of MINK which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein concerning MINK structure and function, one of ordinary skill in the art can modify the sequence of MINK by site-specific mutagenesis, scanning mutagenesis, partial gene deletion or truncation, and the like (See, e.g., U.S. Pat. No. 5,580,723 and Sambrook et al., *Molecular Cloning: A Laboratory Manual*, Second Edition, Cold Spring Harbor Laboratory Press, 1989). The skilled artisan then can test the population of mutagenized polypeptides for diminution in a selected activity and/or for retention of such an activity. Other similar methods for creating and testing dominant negative variants of a protein will be apparent to one of ordinary skill in the art.

In one embodiment according to this and other aspects of the invention, the MINK inhibitor includes a nucleic acid molecule encoding an siRNA specific for MINK. RNA interference (RNAi) is now a well described mechanism for silencing gene expression by double-stranded RNA (dsRNA) having complementary sequence to a target gene to be silenced. The process is known to occur naturally in a wide variety or organisms, including embryos of mammals and other vertebrate. Small interfering RNAs (siRNAs) are 21- to 23-nucleotide (nt) dsRNAs, in which the sense strand is the complement of the target mRNA sequence. These are the effector molecules for inducing RNAi, leading to posttranscriptional gene silencing with RNA-induced silencing complex. In addition to siRNA, which can be chemically synthesized, various other systems in the form of potential effector molecules for posttranscriptional silencing are available, including short hairpin RNAs (shRNAs), long dsRNAs, short temporal RNAs, and micro RNAs (miRNAs) These effector molecules either are processed into siRNA, such as in the case of shRNA, or directly aid gene silencing, as in the case of miRNA. This present invention encompasses the use of shRNA to enable the targeting of MINK mRNAs for degradation in mammalian cells useful in the therapeutic applications discussed herein.

Use of shRNA has the advantage over use of chemically synthesized siRNA in that the suppression of the target gene is typically long-term and stable. Methods and materials for design of the RNAs that mediate RNAi and the methods for transfection of the RNAs into cells and animals are well known in the art and are readily commercially available (Verma N K et al., 2004, *J Clin Pharm Ther* 28:395-404; Mello C C et al., 2004, *Nature* 431:338-42; Dykxhoom D M et al., 2003, *Nat Rev Mol Cell Biol* 4:457-67; Proligo, Hamburg, Germany; Dharmacon Research, Lafayette, Colo., USA; Pierce Chemical—part of Perbio Science—Rockford, Ill., USA; Glen Research, Sterling, Va., USA; ChemGenes, Ashland, Mass., USA; and Cruachem, Glasgow, UK).

The MINK cDNA-specific shRNA can be designed by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The shRNA targeted sequence can be further evaluated using a BLAST homology search to avoid off-target effects on other genes or sequences. Negative controls are designed by scrambling targeted shRNA sequences.

The selected sequence for a shRNA typically has a stem length from 25 to 29 nt and loop size between 4 and 23 nt. DNA insert sequences that encode for shRNA are typically around 70 bp. In one embodiment the insert includes 20 nt inverted repeats that code for a portion of the stem complementary to the target gene and 10 nt spacers that code for the hairpin structure. The portions of the stem structure that binds to the target mRNA are critical for silencing capability of the shRNA and are therefore designed to be completely complementary. Restriction site overhangs of the insert can be conveniently designed to be specific to the vector to be used. In one embodiment the first base of the shRNA corresponding to the target mRNA sequence starts with nucleotides that correspond to the transcription start site for the particular promoter.

shRNAs can be generated in cell lines with the help of commercially available shRNA expression vectors such as pSilencer™ 2.0-U6 and 3.0-H1 vectors from Ambion (Austin, Tex.), the psiRNA™ system including psiRNA-hH1, psiRNA-hH1neo, and psiRNAhH1zeo vectors from InvivoGen (San Diego, Calif.), the psiCHECK™ vectors which include silencing optimization capability, from Promega (Madison, Wis.), and siRNA expression cassettes (SECs) from Ambion's Silencer™ Express system. The shRNA expression vectors are engineered plasmid vectors containing promoters of the type III class of Pol III promoters (H1 RNA, U 6 promoter), a cloning site for stem-looped RNA insert, and a 4 or 5-thymidine transcription termination signal. The polymerase III promoters have well-defined initiation and stop sites, and the transcripts lack a poly (A) tail. Five thymidines define the termination signal for these promoters, and transcript is cleaved after the second uridine, which generates the 3' UU overhang in expressed siRNA, similar to the 3' overhang of synthetic siRNA.

In one embodiment according to this and other aspects of the invention, the MINK inhibitor is a nucleic acid molecule encoding an antisense molecule specific for MINK. In one embodiment according to this and other aspects of the invention, the MINK inhibitor is a nucleic acid molecule encoding an antisense molecule specific for MINK. As used herein, the term "antisense oligonucleotide" or "antisense" describes an oligonucleotide which hybridizes under physiological conditions to DNA comprising a particular gene or to an RNA transcript of that gene and, thereby, inhibits transcription of that gene and/or translation of the mRNA. The antisense molecules are designed so as to hybridize with the target gene or target gene product and thereby interfere with transcription or translation of the target mammalian cell gene. Those skilled in the art will recognize that the exact length of the antisense oligonucleotide and its degree of complementarity with its target will depend upon the specific target selected, including the sequence of the target and the particular bases which comprise that sequence. In one embodiment the antisense oligonucleotide is a unique fragment. A unique fragment is one that is a 'signature' for the larger nucleic acid. For example, a unique fragment is long enough to assure that its precise sequence is not found in molecules outside of the MINK gene. As will be recognized by those skilled in the art, the size of the unique fragment will depend upon its conservancy in the genetic code. Thus, some regions of the MINK gene will require longer segments to be unique while others will require only short segments, typically between 12 and 32 base pairs (e.g., 12, 13, 14, 15, 16, 17, 18, 19, 20, 21, 22, 23, 24, 25, 26, 27, 28, 29, 30, 31, and 32 bases long).

It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, the antisense oligonucleotide should comprise at least 7 and, more preferably, at least 15 consecutive bases which are complementary to the target. Most preferably, the antisense oligonucleotide comprises a complementary sequence of 20-30 bases. Although oligonucleotides may be chosen which are antisense to any region of the gene or RNA (e.g., mRNA) transcripts, in one embodiment the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., 1994, *Cell Mol Neurobiol* 14:439-57) and at which proteins are not expected to bind. The selective binding of the antisense oligonucleotide to a mammalian target cell nucleic acid effectively decreases or eliminates the transcription or translation of the mammalian target cell nucleic acid molecule.

In one embodiment according to this and other aspects of the invention, the MINK inhibitor is contained in a vector that specifically targets thymocytes. For example, the vector that specifically targets thymocytes can be used in the context of bone marrow and organ transplantation.

In one embodiment according to this and other aspects of the invention, the MINK inhibitor is a serine-threonine kinase inhibitor. Serine-threonine inhibitors are known in the art and include ST1571 (Gleevec, also known as Glivec and as CGP57148B; available from Novartis, East Hanover, N.J.), PD98059 (an inhibitor of MAP kinase kinase, i.e., MAP/ERK kinase, from Biosource International, Camarillo, Calif.).

The invention in one aspect provides a method for inhibiting activation-induced cell death of T cells of a mammal. The method according to this aspect of the invention includes the step of down-regulating MINK in T cells of the mammal. In one embodiment according to this aspect of the invention, the MINK is down-regulated by contacting T cells of the mammal with the MINK inhibitor. The contacting can be accomplished using any suitable method, including for example by administering the MINK inhibitor systemically. In one embodiment the MINK inhibitor is contained in a vector that specifically targets T cells. In one embodiment the MINK inhibitor is contained in a vector that specifically targets activated T cells.

Also according to this aspect of the invention, in certain embodiments the MINK inhibitor is a nucleic acid molecule encoding a dominant negative mutant MINK, a nucleic acid molecule encoding an siRNA specific for MINK, or a nucleic acid molecule encoding an antisense molecule specific for MINK. The MINK inhibitor in another embodiment is a serine-threonine kinase inhibitor, as described above.

Further in connection with this and other aspects of the invention, in one embodiment the method further includes the step of contacting the T cells of the mammal with an antigen. An antigen as used herein is a molecule capable of provoking an immune response. The term antigen broadly includes any type of molecule which is recognized by a host immune system as being foreign. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites. Antigens specifically include cancer antigens, infectious disease antigens, and allergens (see below).

In one embodiment according to this and other aspects of the invention, the antigen is a nucleic acid molecule encoding the antigen. Thus according to this and other aspects of the invention, in one embodiment contacting the T cells of the mammal with an antigen refers to contacting the T cells of the mammal with a nucleic acid molecule encoding the antigen. The nucleic acid molecule encoding the antigen can be introduced into cells of the mammal, whereby the resulting cells express the encoded protein, polypeptide, or peptide antigen. The nucleic acid molecule encoding the antigen can be, for example, a virus or a plasmid into which has been introduced a nucleic acid sequence encoding the antigen. In one embodiment the nucleic acid molecule encoding the antigen is part of a nucleic acid molecule encoding a MINK inhibitor. In another embodiment the nucleic acid molecule encoding the antigen is separate from a nucleic acid molecule encoding a MINK inhibitor.

In one embodiment according to this and other aspects of the invention, the antigen is an antigen per se. An antigen per se refers to a preformed antigen, e.g., an antigen other than a nucleic acid molecule encoding the antigen.

The invention is also based in part on the discovery by the inventors that $CD4^+$ T cells emerging from the thymus following negative selection are biased toward a Th1 phenotype. The invention in another aspect provides a method for biasing an immune response away from a Th1 response in a subject. The method according to this aspect of the invention includes the step of administering to the subject an effective amount of a MINK inhibitor. The administering can be accomplished using any suitable method, including for example by administering the MINK inhibitor systemically. A Th1 response as used herein refers to an immune response characterized by activation of $CD4^+$ Th1 cells and production of IFN-γ, IL-12, and/or antibody isotype switching to IgG2a (in the mouse) or IgG1 (in humans). Th1 responses are typically mounted in response to infection by intracellular pathogens including viruses, *Leishmania*, and microbes that infect or activate macrophages, including *Listeria* and mycobacteria. In addition, Th1 responses are typically mounted in response to microbes and antigens that activate NK cells. A Th1 response is to be distinguished from a Th2 response, the latter characterized by activation of $CD4^+$ Th2 cells and production of IL-4, IL-5, IL-13, and/or antibody isotype switching to IgE. Th2 responses are typically mounted in response to infection with extracellular pathogens such as helminths and in response to contact with allergens. While Th1 responses and Th2 responses are generally regarded as counter-regulatory, it is to be understood that Th1 responses and Th2 responses represent extremes of a continuum and need not be absolutely mutually exclusive. Thus a Th1 response specifically includes an immune response that is predominantly Th1 in character, as opposed to predominantly Th2 in character.

Also according to this aspect of the invention, in certain embodiments the MINK inhibitor is a nucleic acid molecule encoding a dominant negative mutant MINK, a nucleic acid molecule encoding an siRNA specific for MINK, a nucleic acid molecule encoding an antisense molecule specific for MINK, or a serine-threonine kinase inhibitor, as described above. Further according to this aspect of the invention, in one embodiment the MINK inhibitor is contained in a vector that specifically targets activated T cells.

Further still in accord with this aspect of the invention, in one embodiment the method further includes the step of administering an antigen to the subject. The antigen can be in the form of a nucleic acid molecule encoding the antigen or an antigen per se.

Certain aspects of the invention involve increasing MINK to modify basic immune properties. These aspects of the invention include methods for enhancing negative selection of thymocytes, enhancing AICD of T cells, and biasing an immune response toward a Th1 response.

In one aspect the invention provides a method for enhancing negative selection of thymocytes in a mammal. The method according to this aspect of the invention includes the step of up-regulating MINK in thymocytes of the mammal. Up-regulating refers generally to increasing the expression and/or function of a particular biological molecule or process. In one embodiment up-regulating refers to de novo expression and/or function of a particular biological molecule or process. As used herein, up-regulating MINK thus refers to increasing the expression and/or function of MINK. In one embodiment up-regulating MINK refers to increasing the expression of MINK protein. In one embodiment up-regulating MINK refers to increasing the expression of a nucleic acid encoding MINK protein. In one embodiment up-regulating MINK refers to increasing the function of MINK protein, e.g., by increasing enzymatic activity of MINK, increasing interaction between MINK and at least one other protein, or increasing conformational changes of MINK. Up-regulation of MINK can be assessed by direct measurement of enhanced MINK expression or function, by measurement of enhanced downstream signaling events in MINK signaling pathway, and by measurement of enhanced downstream consequences of signaling by MINK, e.g., enhanced negative selection and enhanced AICD of T cells (see below).

In one embodiment according to this and other aspects of the invention, MINK is upregulated by contacting thymocytes of the mammal with a MINK activator. The contacting can be accomplished using any suitable method, including for example by administering the MINK activator systemically or by administering the MINK activator by direct injection into the thymus. As used herein a MINK activator is an agent that specifically increases expression and/or function of MINK. In one embodiment the MINK activator is an agent that specifically increases expression of MINK. In one embodiment the MINK activator is an agent that specifically increases MINK function.

In one embodiment according to this and other aspects of the invention, the MINK activator includes a nucleic acid molecule encoding MINK. In one embodiment according to this and other aspects of the invention, the MINK activator is a nucleic acid molecule encoding MINK.

A nucleic acid molecule encoding MINK refers to any DNA or RNA molecule that encodes a protein product corresponding to a MINK protein. In one embodiment the nucleic acid molecule encoding MINK is a DNA or RNA encoding a naturally occurring isoform of MINK. In one embodiment the nucleic acid molecule encoding MINK is a DNA or RNA encoding a naturally occurring isoform of human MINK. Examples of nucleic acid molecules encoding MINK have been described and include, for example, the following GenBank accession numbers for various isoforms of human MINK: NM_015716, NM_170663, AY775058, and NM_153827. Protein products of the forgoing include NP_056531 (1295 amino acids; SEQ ID NO: 1), NP_733763 (1303 amino acids; SEQ ID NO:10), AAV41830 (1312 amino acids; SEQ ID NO:9), and NP_722549 (1332 amino acids; SEQ ID NO:8), respectively. In one embodiment the nucleic acid molecule encoding MINK is a DNA or RNA encoding a naturally occurring isoform of murine MINK. Examples of nucleic acid molecules encoding murine MINK have been described and include, for example, the following GenBank accession numbers: AB035697, AB041925, and BC052474. Protein products of the forgoing include BAA90752 (1300 amino acids; SEQ ID NO:7), BAA94837 (1302 amino acids), and AAH52474 (1334 amino acids), respectively. The forgoing GenBank accession numbers are provided only as exemplification and are not meant to be limiting.

In one embodiment according to this and other aspects of the invention, the MINK activator includes a nucleic acid molecule encoding gene activation sequences specific for MINK. In one embodiment according to this and other aspects of the invention, the MINK activator is a nucleic acid molecule encoding gene activation sequences specific for MINK.

In one embodiment according to this and other aspects of the invention, the nucleic acid molecule encoding gene activation sequences specific for MINK includes a DNA construct including a targeting sequence, a regulatory sequence, a MINK exon, and an unpaired splice-donor site, such that the regulatory sequence, the MINK exon, and the unpaired splice-donor site are operatively linked to genomic MINK sequence upon integration of the DNA construct into genomic DNA of activated T cells of the subject. In one embodiment according to this and other aspects of the invention, the nucleic acid molecule encoding gene activation sequences specific for MINK is a DNA construct including a targeting sequence, a regulatory sequence, a MINK exon, and an unpaired splice-donor site, such that the regulatory sequence, the MINK exon, and the unpaired splice-donor site are operatively linked to genomic MINK sequence upon integration of the DNA construct into genomic DNA of activated T cells of the subject.

In one embodiment according to this and other aspects of the invention, the MINK activator is an anti-T-cell receptor complex antibody. An anti-T-cell receptor complex antibody refers to an antibody that is specific for at least one component a T-cell receptor complex. T-cell receptors (TCR) are expressed on thymocytes as well as on T cells. As used herein, T-cell receptor complex refers to a complex including a clonotypic α/β or γ/δ TCR heterodimer and invariant signaling proteins CD3 δ, ε, γ, and the ζ chain. An anti-T-cell receptor complex antibody thus can be specific for any one or more of these individual components. In one embodiment the anti-T-cell receptor complex antibody is an anti-CD3 antibody. For example, OKT3 is a murine monoclonal antibody specific for human CD3ε.

Further according to this and other aspects of the invention, in one embodiment the MINK activator is contained in a vector that specifically targets thymocytes.

Further still in accord with this aspect of the invention, in one embodiment the method further includes the step of contacting the thymocytes of the mammal with an antigen, wherein the antigen is as described above.

In one aspect the invention provides a method for enhancing activation-induced cell death of T cells of a mammal. The method according to this aspect of the invention includes the step of up-regulating MINK in T cells of the mammal. In one embodiment according to this aspect of the invention, the MINK is up-regulated by contacting T cells of the mammal with a MINK activator. The contacting can be accomplished using any suitable method, including for example by administering the MINK activator systemically. In one embodiment the MINK activator is contained in a vector that specifically targets T cells. In one embodiment the MINK activator is contained in a vector that specifically targets activated T cells.

Also according to this aspect of the invention, in certain embodiments the MINK activator is a nucleic acid molecule encoding MINK or a nucleic acid molecule encoding gene activation sequences specific for MINK, as described above. In one embodiment according to this aspect of the invention, the MINK activator is an anti-T-cell receptor complex antibody.

Further in connection with this aspect of the invention, in one embodiment the method further includes the step of contacting the T cells of the mammal with an antigen, as described above.

The invention in another aspect provides a method for biasing an immune response toward a Th1 response in a subject. The method according to this aspect of the invention includes the step of administering to the subject an effective amount of a MINK activator. The administering can be accomplished using any suitable method, including for example by administering the MINK activator systemically. In certain embodiments the MINK activator is contained in a vector that specifically targets T cells; the MINK activator is contained in a vector that specifically targets activated T cells; and/or the MINK activator is a nucleic acid molecule encoding MINK or a nucleic acid molecule encoding gene activation sequences specific for MINK, as described above. In one embodiment according to this aspect of the invention, the MINK activator is an anti-T-cell receptor complex antibody.

Further in connection with this aspect of the invention, in one embodiment the method further includes the step of administering an antigen to the subject, wherein the antigen is as described above.

Certain aspects of the invention involve reducing MINK in a subject to treat a subject having a specific disease or condition. These aspects of the invention include methods for vaccinating a subject, treating a subject with cancer, and treating a subject with an infectious disease. Also included is a method for preparing bone marrow cells for a subject receiving a bone marrow autograft.

As used herein, the terms treat and treating refer to preventing, reducing, or eliminating at least one symptom or sign of a disease or condition in a subject. Thus for example treating a subject having cancer refers to preventing, reducing, or eliminating at least one symptom or sign of a cancer in a subject. As another example treating a subject having an infectious disease refers to preventing, reducing, or eliminating at least one symptom or sign of an infectious disease in a subject. As yet another example, treating a subject having an allergy refers to preventing, reducing, or eliminating at least one symptom or sign of an allergy in a subject. Persons of skill in the medical arts will be aware of suitable methods for assessing the status of a subject having or at risk of having a particular disease or condition.

In one aspect the invention provides a method for vaccinating a subject. The method according to this aspect of the invention includes the steps of administering to the subject a vaccine comprising an antigen, and administering to the subject an effective amount of a MINK inhibitor. The vaccine and the MINK inhibitor can be administered together or separately, and they each can be administered by any suitable route of administration. Preferably the method results in an enhanced immune response to the antigen compared to vaccination without the MINK inhibitor.

A vaccine as used herein refers to a pharmaceutical preparation including at least one antigen that is administered to a subject to induce protective immunity against the antigen. The vaccine can optionally include at least one adjuvant. An adjuvant refers to a substance that non-specifically enhances T cell activation, either directly or indirectly. Examples of adjuvants are well known in the art and include, for example, certain aluminum salts, Freund's adjuvant (complete or incomplete), saponins purified from the bark of the *Q. saponaria* tree (e.g., QS21, Aquila Biopharmaceuticals, Worcester, Mass.), derivatives of lipopolysaccharides such as monophosphoryl lipid A (MPL, Ribi ImmunoChem Research, Hamilton, Mont.), muramyl dipeptide (MDP. Ribi), and CpG nucleic acid (see, e.g., U.S. Pat. No. 6,207, 646). In one embodiment the vaccine includes an antigen per se, i.e., a preformed antigen. In one embodiment a vaccine includes a nucleic acid encoding a polypeptide or protein antigen.

MINK inhibitors and antigens according to this aspect of the invention are as described above. In one embodiment in which the antigen is a nucleic acid molecule encoding the antigen, the MINK inhibitor and the nucleic acid molecule encoding the antigen are present in a single vector.

In one aspect the invention provides a method for treating a subject with cancer. The method according to this aspect of the invention includes the step of administering to the subject an effective amount of a MINK inhibitor. The MINK inhibitor can be administered to the subject by any suitable route of administration, including for example, systemically and locally (into tumor or lymph node draining a site of a tumor). MINK inhibitors according to this aspect of the invention are as described above.

A subject with cancer is a subject having an objective manifestation of a cancer. "Cancer" as used herein refers to a population of abnormal cells, generally of host origin, the growth of which is not regulated by external signals and which cells have the capacity to invade normal tissues and metastasize to nonadjacent sites. Cancers which migrate from their original location and seed vital organs can eventually lead to the death of the subject through the functional deterioration of the affected organs. Cancer includes both solid organ cancers and hematopoietic cancers. Hematopoietic cancers, such as leukemia, are able to outcompete the normal hematopoietic compartments in a subject, thereby leading to hematopoietic failure (in the form of anemia, thrombocytopenia and neutropenia), ultimately causing death.

A metastasis is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of various diagnostic imaging modalities, including magnetic resonance imaging (MRI) scans, computed tomography (CT) scans, X-rays and bone scans, in addition to physical examination, biopsy, blood and platelet counts, liver function studies, and other tests and techniques known in the art.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

In one embodiment the method according to this aspect of the invention further includes the step of administering a cancer antigen to the subject. A cancer antigen as used herein is a compound, such as a peptide or protein, associated with a tumor or cancer cell surface and which is capable of provoking an immune response when expressed on the surface of an antigen presenting cell in the context of an MHC molecule. Some of these antigens are encoded, although not necessarily expressed, by normal cells. These antigens can be characterized as those which are normally silent (i.e., not expressed) in normal cells, those that are expressed only at certain stages of differentiation, and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Cancer antigens can be prepared from cancer cells either by preparing crude extracts of cancer cells, for example, as described in Cohen P A et al. (1994, *Cancer Res* 54:1055-8), by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

In one embodiment the cancer antigen is a nucleic acid encoding the cancer antigen. In one embodiment in which the cancer antigen is a nucleic acid molecule encoding the cancer antigen, the MINK inhibitor and the nucleic acid molecule encoding the cancer antigen are present in a single vector. In another embodiment the cancer antigen is a cancer antigen per se.

The invention in according to one aspect of the invention provides a method for treating a subject with an infectious disease. The method according to this aspect of the invention includes the step of administering to the subject an effective amount of a MINK inhibitor. The MINK inhibitor can be administered to the subject by any suitable route of administration, including for example, systemically. MINK inhibitors according to this aspect of the invention are as described above.

A subject with an infectious disease refers to a subject having an objective manifestation of infection with an infectious microbe. An "infectious disease" as used herein refers to a disorder arising from the invasion of a host, superficially, locally, or systemically, by an infectious microorganism (microbe). Infectious microorganisms (microbes) include bacteria, viruses, parasites, and fungi.

Examples of viruses that have been found in humans include but are not limited to: Retroviridae (e.g. human immunodeficiency viruses, such as HIV-1, also referred to as HDTV-III, LAVE or HTLV-III/LAV, or HIV-III; and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunya viruses, phleboviruses and Nairo viruses); Arenaviridae (hemorrhagic fever viruses); Reoviridae (e.g. reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Bacteria include both gram negative and gram positive bacteria. Such gram positive bacteria include, but are not limited to, *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borrelia burgdorferi, Legionella pneumophilia, Mycobacteria* sps (e.g. *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelii*.

Examples of fungi include *Cryptococcus neoformans, Histoplasma capsulatum, Coccidioides immitis, Blastomyces dermatitidis, Chlamydia trachomatis, Candida albicans*, and *Aspergillus* spp.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissue parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

In one embodiment the method according to this aspect of the invention further includes the step of administering a microbial antigen to the subject. A microbial antigen as used herein is an antigen of an infectious microorganism, wherein the infectious microorganism includes but is not limited to viruses, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

In one embodiment the microbial antigen is a nucleic acid encoding the microbial antigen. In one embodiment in which the microbial antigen is a nucleic acid molecule encoding the microbial antigen, the MINK inhibitor and the nucleic acid molecule encoding the microbial antigen are present in a single vector. In another embodiment the microbial antigen is a microbial antigen per se.

In one aspect the invention provides a method for preparing bone marrow cells for a subject receiving a bone marrow autograft. The method according to this aspect of the invention includes the step of down-regulating MINK in autograft bone marrow cells. Bone marrow cells so prepared by this method are believed to exhibit increased immune activity directed against cancerous bone marrow-derived or other cancer cells that represent non-self. The method according to this aspect of the invention will be of particular use in the treatment of multiple myeloma (see below).

Bone marrow cells shall refer to hematopoietic cells, including but not limited to hematopoietic stem cells, that are normally found in the marrow. The bone marrow is the major site of generation of all circulating blood cells, including immature lymphocytes, in adult mammals. Bone marrow cells can be harvested for ex vivo treatment and for use as autografts and for use as bone marrow transplants (see below).

A subject receiving a bone marrow autograft is a subject that is about to receive or that has already received a population of bone marrow cells originally derived from that subject. A bone marrow autograft is also known in the art as an autologous bone marrow transplant. In one embodiment the subject receiving a bone marrow autograft is a subject that is about to receive a population of bone marrow cells originally derived from itself. In one embodiment the subject receiving a bone marrow autograft is a subject that has already received a population of bone marrow cells originally derived from itself. Typically the bone marrow autograft includes bone marrow cells of the subject which have been modified ex vivo through some process that involves modification, selection, or expansion of specific cells present in the bone marrow cells. For example, in one embodiment the bone marrow cells are modified ex vivo by introducing into the cells a lentivirus vector encoding a short homologous RNA targeting MINK.

Indications for and methods of performing bone marrow autografts are well known in the art. Indications include various hematologic malignancies, including leukemia, lymphoma, and multiple myeloma, as well as certain solid tumors, including breast cancer, testicular cancer, ovarian cancer, Wilms' tumor, and Ewing's sarcoma. This list is not meant to be limiting.

Autograft bone marrow cells refers to bone marrow cells included in and derived from bone marrow cells administered to a subject receiving a bone marrow autograft.

In one embodiment according to this aspect of the invention, the down-regulating MINK in autograft bone marrow cells involves contacting the autograft bone marrow cells with a MINK inhibitor. MINK inhibitors are as described above.

In one embodiment the subject receiving the bone marrow autograft has multiple myeloma. Multiple myeloma as used herein refers to a well known disease involving a malignant proliferation of plasma cells derived from a single clone. Multiple myeloma is associated with various clinical manifestations including bone pain, hypercalcemia, pathologic fractures, cord compression, lytic bone lesions, and osteoporosis, all associated with skeletal destruction by the tumor; renal failure arising from secreted tumor products; anemia; infection; neurologic symptoms arising from hyperviscosity and hypercalcemia, bleeding, and mass lesions. Diagnosis is usually based on findings of marrow plasmacytosis, lytic bone lesions, and serum and/or urine M component, although all three features are not required to make a diagnosis. Conventional treatment is based on chemotherapy, for example repeated courses of an alkylating agent (e.g., melphalan and cyclophosphamide) and prednisone.

In one aspect the invention provides a preparation of isolated bone marrow cells with reduced MINK. The preparation is made by contacting bone marrow cells with a MINK inhibitor, such that MINK expression and/or MINK function is inhibited in the bone marrow cells.

Certain aspects of the invention involve increasing MINK in a subject to treat a subject having a specific disease or condition. These aspects of the invention include methods for treating a subject having autoimmune disease, treating a subject receiving an allograft, and treating a subject having allergy.

In one aspect the invention provides a method for treating a subject having autoimmune disease (AID). The method according to this aspect of the invention includes the step of administering to the subject an effective amount of a MINK activator. The MINK activator can be administered by any suitable route of administration, including for example systemically. MINK activators are as described above.

A subject having an autoimmune disease is a subject with an objective manifestation of an autoimmune disease. Autoimmune disease refers to a class of diseases in which a subject's own antibodies react with host tissue or in which immune effector T cells are autoreactive to endogenous self peptides and cause destruction of tissue. Thus an immune response is mounted against a subject's own antigens, referred to as self antigens. A "self-antigen" as used herein refers to an antigen of a normal host tissue. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer.

Autoimmune diseases include but are not limited to rheumatoid arthritis, insulin-dependent diabetes mellitus (type I diabetes), Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, and insulin resistance. Recently atherosclerosis has also been classified as an autoimmune disease.

In one embodiment according to this aspect of the invention, the subject having AID is a subject having insulin-dependent diabetes mellitus (also known as type 1 diabetes and IDDM).

In one embodiment according to this aspect of the invention, the method further includes the step of administering an antigen to the subject.

The invention in one aspect provides a method for treating a subject receiving an allograft. The method according to this aspect of the invention includes the step of administering to the subject an effective amount of a MINK activator. The MINK activator can be administered by any suitable route of administration, including for example systemically. MINK activators are as described above.

A subject receiving an allograft refers to a subject that is about to receive or that has already received an allograft. In one embodiment the subject receiving an allograft refers to a subject that is about to receive an allograft. In one embodiment the subject receiving an allograft refers to a subject that has already received an allograft. An allograft refers to any cell, tissue, or organ transplanted from one individual (the donor) of a species to another individual (the recipient) of the same species. The immune system of the recipient typically will respond to an allograft as foreign (not self). Allografts specifically include both solid organ allografts and bone marrow allografts. Solid organ allografts include but are not limited to kidney, liver, heart, pancreas, lung, and small intestine allografts, as well as any combination thereof.

In one embodiment according to this aspect of the invention, the subject receiving the allograft has allograft rejection. Allograft rejection refers to an immunological response directed against an allograft mounted by the immune system of the recipient. The rejection can be hyperacute, acute, or chronic. Hyperacute rejection is usually associated with the presence of circulating preformed antibodies specific for antigens of the allograft. Acute rejection is believed to represent primarily T-cell-mediated immunity directed against the allograft. Chronic rejection is believed to be a complex mixture of T-cell-mediated (cellular) immunity, B-cell-mediated (humoral) immunity, and more nonspecific inflammatory response resulting in chronic injury to the allograft with consequent loss of graft function. Unless it can be avoided or controlled, allograft rejection typically leads to loss of graft function and viability. Allograft rejection is readily recognized by those of skill in the art. Various non-invasive and invasive tests, including allograft biopsy, can be performed to diagnose and to monitor allograft rejection. Conventional methods for treating allograft rejection are well known in the art and include administration of one or more agents including cyclosporine A, tacrolimus (FK-506), prednisone, methylprednisolone, sirolimus (rapamycin), mycophenolate mofetil, azathioprine, anti-CD25 monoclonal antibody, anti-CD3 monoclonal antibody (OKT3), and antithymocyte globulin.

In one embodiment according to this aspect of the invention, the subject receiving the allograft is a subject receiving a bone marrow transplant. A subject receiving a bone S marrow transplant refers to a subject that is about to receive or that has already received a population of bone marrow cells originally derived from a donor other than the subject, i.e., a subject that is about to receive or that has already received a bone marrow allograft. In one embodiment the subject receiving a bone marrow transplant is a subject that is about to receive a bone marrow allograft. In one embodiment the subject receiving a bone marrow transplant is a subject that has already received a bone marrow allograft. Subjects receiving bone marrow transplants typically include subjects having hematologic malignancies and other hematologic disorders including leukemia, lymphoma, multiple myeloma, aplastic anemia, thalassemia, sickle cell anemia, severe combined immunodeficiency (SCID), Wiskott-Aldrich syndrome, and Chediak-Higashi syndrome; subjects having other malignancies, including neuroblastoma; and subjects having other nonmalignant conditions including radiation injury. Those of skill in the art are familiar with the indications for and methods for carrying out bone marrow transplant.

In one embodiment according to this aspect of the invention, the subject receiving a bone marrow transplant has graft-versus-host disease. Graft-versus-host disease (GvHD) refers to an immunological response mounted by an allograft against tissues of the recipient. GvHD most typically occurs in the setting of bone marrow transplant, where bone marrow-derived cells of donor origin recognize antigens of the recipient as non-self. GvHD includes both acute GvHD and chronic GvHD. Tissues of the recipient usually most affected by GvHD include those of skin, liver, and intestine. GvHD is readily recognized by those of skill in the art. Conventional methods for treating GvHD are well known in the art and include administration of one or more agents including methylprednisolone and anti-T-cell antibodies.

In one embodiment according to this aspect of the invention, the subject receiving the allograft is a subject receiving a solid organ transplant. A subject receiving a solid organ transplant refers to a subject that is about to receive or that has already received an allograft of a solid organ. In one embodiment the subject receiving a solid organ transplant is a subject that is about to receive a solid organ allograft. In one embodiment the subject receiving a solid organ transplant is a subject that has already received a solid organ allograft. Solid organ allografts include but are not limited to kidney, liver, heart, pancreas, lung, and small intestine allografts, as well as any combination thereof. Solid organ allografts also include skin allografts, limb allografts, and allografts of partial organs such as partial liver allograft.

In one embodiment according to this aspect of the invention, the subject receiving the allograft is a subject receiving a cell or tissue transplant other than a bone marrow transplant or solid organ transplant. A subject receiving a cell or tissue transplant other than a bone marrow transplant or solid organ transplant refers to a subject that is about to receive or that has already received an allograft of cells or of a tissue other than a bone marrow transplant or a solid organ transplant. In one embodiment the subject receiving a cell or tissue transplant is a subject that is about to receive a cell or tissue allograft. In one embodiment the subject receiving a cell or tissue transplant is a subject that has already received a cell or tissue allograft. In one embodiment a cell allograft is an islet cell allograft.

In one aspect the invention provides a method for treating a subject having allergy. The method according to this aspect of the invention includes the step of administering to the subject an effective amount of a MINK activator. The MINK activator can be administered by any suitable route of administration, including for example systemically or locally, for example to skin, nasal mucosa, or lung. MINK activators are as described above.

A "subject having an allergy" is a subject that has an allergic reaction in response to an allergen. An "allergy" refers to acquired hypersensitivity to a substance (allergen). An allergen refers to a substance (antigen) that can induce an allergic or asthmatic response in a susceptible subject. While the list of allergens is enormous, commonly recognized allergens include pollens, insect venoms, animal dander, dust, fungal spores, drugs (e.g. penicillin), and foods (e.g., peanuts). Examples of natural, animal and plant allergens include but are not limited to proteins specific to the following genuses: *Agropyron* (e.g. *Agropyron repens*); *Agrostis* (e.g. *Agrostis alba*); Alder; *Alnus* (*Alnus gultinoasa*); *Alternaria* (*Alternaria alternata*); *Ambrosia* (*Ambrosia artemiisfolia; Anthoxanthum* (e.g. *Anthoxanthum odoratum*); *Apis* (e.g. *Apis multiflorum*); *Arrhenatherum* (e.g. *Arrhenatherum elatius*); *Artemisia* (*Artemisia vulgaris*); *Avena* (e.g. *Avena sativa*); *Betula* (*Betula verrucosa*); *Blattella* (e.g. *Blattella germanica*); *Bromus* (e.g. *Bromus inermis*); *Canis* (*Canis familiaris*); *Chamaecyparis* (e.g. *Chamaecyparis obtusa*); *Cryptomeria* (*Cryptomeria japonica*); *Cupressus* (e.g. *Cupressus sempervirens, Cupressus arizonica* and *Cupressus macrocarpa*); *Dactylis* (e.g. *Dactylis glomerata*); *Dermatophagoides* (e.g. *Dermatophagoides farinae*); *Felis* (*Felis domesticus*); *Festuca* (e.g. *Festuca elatior*); *Holcus* (e.g. *Holcus lanatus*); *Juniperus* (e.g. *Juniperus sabinoides, Juniperus virginiana, Juniperus communis* and *Juniperus ashei*); *Lolium* (e.g. *Lolium perenne* or *Lolium multiflorum*); *Olea* (*Olea europa*); *Parietaria* (e.g. *Parietaria officinalis* or *Parietaria judaica*); *Paspalum* (e.g. *Paspalum notatum*); *Periplaneta* (e.g. *Periplaneta americana*); *Phalaris* (e.g. *Phalaris arundinacea*); *Phleum* (e.g. *Phleum pratense*); *Plantago* (e.g. *Plantago lanceolata*); *Poa* (e.g. *Poa pratensis* or *Poa compressa*); *Quercus* (*Quercus alba*); *Secale* (e.g. *Secale cereale*); *Sorghum* (e.g. *Sorghum halepensis*); *Thuya* (e.g. *Thuya orientalis*); and *Triticum* (e.g. *Triticum aestivum*).

In one embodiment the subject having allergy is a subject having asthma.

In one embodiment according to this aspect of the invention, the method further includes the step of contacting T cells of the subject with an allergen. In one embodiment the contacting step involves exposing the subject to the allergen, for example through environmental contact. In one embodiment the contacting step involves administering the allergen to the subject. As in other aspects of the invention involving antigens, in one embodiment the allergen is a nucleic acid encoding the allergen. Similarly, in one embodiment the allergen is an allergen per se.

Certain aspects of the invention relate to screening methods. Methods according to these aspects of the invention are useful for identifying MINK-specific inhibitor compounds, determining if a subject has impaired negative selection of developing thymocytes, and identifying a subject a susceptible to development of an autoimmune disease.

In one aspect the invention provides a method for identifying a MINK-specific inhibitor. The method according to this aspect of the invention includes the steps of contacting a test population of T cells with a MINK activator and a test agent, measuring a test MINK activity (D) in the contacted test population of T cells, comparing the test MINK activity (D) to a first control MINK activity (A) in a first control population of T cells, said first control population of T cells not having MINK activity, wherein the first control population of T cells is contacted with the MINK activator, comparing the test MINK activity (D) to a second control MINK activity (B) in a second control population of T cells, said second control population of T cells having MINK activity, wherein the second control population of T cells is contacted with the MINK activator, and identifying the test agent as a MINK-specific inhibitor when (D−A)/(B−A) is less than 1. In one embodiment the test population of T cells and the second control population of T cells are derived from a single common population of T cells, such that they differ only in that the test population is contacted with the test agent while the second control population is not contacted with the test agent.

In one embodiment according to this aspect of the invention, the MINK activator is an anti-T-cell receptor complex antibody.

In one embodiment according to this aspect of the invention, the MINK activity is JNK activation. JNK activation includes phosphorylation of JNK. In one embodiment measurement of JNK activation can be determined directly using anti-phosphoJNK antibodies. In one embodiment measurement of JNK activation can be indirect, for example, by measuring phosphorylation of elements downstream of JNK activation or by measuring apoptosis, e.g., by TUNEL assay. In one embodiment according to this aspect of the invention, the MINK activity is autophosphorylation of MINK. In one embodiment autophosphorylation of MINK can be measured using anti-phosphoMINK antibodies.

In one embodiment according to this and other aspects of the invention, the method is performed in a high throughput manner. As used herein high throughput refers to the serial or parallel performance of multiple assays such that the rate of assay performance significantly exceeds a corresponding rate performed by a standard or non-high throughput manner. For example, the rate of assay performance can be at least two-fold greater, and more typically 10- to 1000-fold greater than the rate performed by a standard or non-high throughput manner. High throughput screening frequently achieves assay rates of tens, hundreds, thousands, or even tens of thousands of assays performed in a single day. General methods and devices useful for performing high throughput screening are well known in the art. These include the use of multiwell plates, robotic sample handling devices, multichannel analyzers of various types, and the like.

The invention in one aspect provides a method for determining if a subject has impaired negative selection of developing thymocytes. The method according to this aspect of the invention includes the steps of isolating messenger RNA, cDNA, or genomic DNA from the subject; screening the messenger RNA, cDNA, or genomic DNA for a nucleic acid molecule encoding a mutant MINK; and determining the subject has impaired negative selection of developing thymocytes when the messenger RNA, cDNA, or genomic DNA comprises a nucleic acid molecule encoding a mutant MINK. In one embodiment according to this aspect of the invention, mutant MINK refers to a particular isoform of MINK. For example, specific isoforms of MINK may turn out to be more or less effective at inducing negative selection of thymocytes. In another embodiment according to this aspect of the invention, mutant MINK refers to a MINK polypeptide including at least one amino acid substitution or deletion compared to any recognized isoform of MINK.

In one embodiment according to this aspect of the invention, the nucleic acid molecule encoding the mutant MINK comprises a mutation of sequence encoding a catalytic domain of MINK. A catalytic domain of MINK in one embodiment corresponds to amino acid residues 25-307 of murine MINK, GenBank accession no. BAA90752 (SEQ ID NO:7). In one embodiment according to this aspect of the invention, the nucleic acid molecule encoding the mutant MINK comprises a mutation of sequence encoding a proline-rich domain of MINK. A proline-rich domain of MINK in one embodiment corresponds to amino acid residues 551-764 of murine MINK, GenBank accession no. BAA90752. In one embodiment according to this aspect of the invention, the nucleic acid molecule encoding the mutant MINK comprises a mutation of sequence encoding a GCK homology domain of MINK. A GCK homology domain of MINK in one embodiment corresponds to amino acid residues 976-1300 of murine MINK, GenBank accession no. BAA90752.

The methods of this aspect of the invention can be used to support or suggest a diagnosis of an autoimmune disease. In one embodiment according to this aspect of the invention, the subject is suspected of having insulin-dependent diabetes mellitus. In one embodiment according to this aspect of the invention, the subject is suspected of having multiple sclerosis.

In one aspect the invention provides a method for identifying a subject as susceptible to development of an autoimmune disease (AID). The method according to this aspect of the invention includes the steps of measuring MINK activity in a population of T cells of a test subject suspected of being susceptible to development of an AID, comparing the MINK activity in the population of T cells of the test subject to MINK activity in a population of T cells of a control subject, and identifying the test subject as susceptible to development of the AID when the MINK activity in the population of T cells of the control subject exceeds the MINK activity in the population of T cells of the test subject.

The methods of the invention involve the use of effective amounts of various MINK inhibitors and MINK activators. The term effective amount refers generally to the amount necessary or sufficient to realize a desired biologic effect. A therapeutically effective amount, as used herein, refers to the amount necessary or sufficient to realize a desired therapeutic effect, i.e., to treat a condition or disease. The therapeutically effective amount can vary depending on the route of administration, the formulation, the disease or condition being treated, the particular active agent being administered, the size of the subject, or the severity of the disease or condition. A therapeutically effective amount can be administered as one or more doses.

Combined with the teachings provided herein, by choosing among the various active compounds and weighing factors such as potency, relative bioavailability, patient body weight, severity of adverse side-effects, and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular MINK inhibitor or MINK activator being administered, the size of the subject, or the severity of the disease or condition. One of ordinary skill in the art can empirically determine the effective amount of a particular MINK inhibitor or MINK activator and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

It is believed by the inventors that effects of MINK may be dose-dependent. More specifically, it is believed by the inventors that MINK can induce AICD and/or increased survival of Th1 cells. Which of these will predominate for a given level of MINK is to be further delineated. However, it is currently the belief of the inventors that apoptotic effects of MINK will involve greater amounts of MINK activity than do Th1 biasing effects of MINK. Thus it may be possible to effect an amount of MINK to favor AICD or Th1 biasing.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from animal models. A therapeutically effective dose can also be determined from human data for MINK inhibitors or MINK activators which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the MINK inhibitor or MINK agonist can be administered to a subject by any mode allowing the MINK inhibitor or MINK agonist to be taken up by the appropriate target cells. "Administering" the pharmaceutical composition of the present invention may be accomplished by any means known to the skilled artisan. Routes of administration include but are not limited to parenteral (e.g., intravenous, intramuscular, subcutaneous, intradermal, intraperitoneal, intrathecal) oral, transdermal (e.g., via a patch), or mucosal (e.g., intranasal, buccal, sublingual, intratracheal, pulmonary, intrarectal, intravaginal, etc.). An injection may be in a bolus or a continuous infusion.

The MINK inhibitors, MINK activators, antigens, and adjuvants may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a combination of adjuvants and antigens optionally included in a pharmaceutically-acceptable carrier. The term "pharmaceutically-acceptable carrier" means one or more compatible solid or liquid fillers, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being co-mingled with the compounds of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

Antigens or adjuvants useful in the invention may be delivered in mixtures of two or more antigens or adjuvants.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

General Methods

Mice. Except as noted otherwise, all mice used in the experiments were age- and sex-matched C57BL/6 (female or male), Rag2$^{-/-}$ (H-2b, female or male), HY TCR transgenic (tg) mice (male), $\beta_2$m$^{-/-}$, Abb$^{-/-}$ and Abb$^{-/-}$ KbDb$^{-/-}$ mice (Taconic, Germantown, N.Y.). OTII TCR tg mice were a gift from Dr. Hidde Ploegh (Harvard Medical School, Boston, Mass.). All experiments involving animals were performed in compliance with Federal laws and Institutional guidelines and approved by the Dana-Farber Cancer Institute Animal Care Use Committee.

Flow Cytometry and Cell Sorting. Single cell suspensions of lymphocytes from thymus, spleen, lymph node (LN), or bone marrow (BM) were prepared and stained for three- or four-color FACS analysis by standard procedures. Results were analyzed using either Expo32 (Beckman Coulter) or Flow Jo (San Carlos, Calif.) software. CD4 precursors were isolated from class I$^{-/-}$ mice according to IL-7R$^+$CD4$^{hi}$CD8$^{lo}$, while CD8 precursors were isolated from class II$^{-/-}$ mice according to IL-7R$^+$CD4$^{lo}$CD8$^{hi}$ [34,35]. Mature CD4 SP cells were sorted according to CD4$^+$HSA$^{lo}$ and mature CD8 SP cells were sorted according to CD8$^+$HSA$^{lo}$. CD4$^+$HSA$^{lo}$ (CD4SP) or CD8$^+$HSA$^{lo}$ (CD8SP) mature thymocytes were sorted using enriched CD4$^+$ or CD8$^+$ cells as a starting population. Immediate reanalysis of double sorted populations by three-color flow cytometry revealed contamination with <1-2% of cells expressing the inappropriate cell surface markers in all cases.

Real time PCR. Total RNA was prepared from thymocytes in different stages using RNeasy Mini Kit (Qiagen, Valencia, Calif.). cDNA was synthesized using oligo dT primers and ThermoScript reverse polymerase (Invitrogen, Carlsbad, Calif.) according to the manufacturer's instructions. Quantitative real-time PCR was performed on an ABI 7700 (Applied Biosystems, Foster City, Calif.) using the QuantiTect Probe PCR kit (Qiagen, Valencia, Calif.). Taqman real time PCR primers were as follows: Mink-F: acacttacgggcggatca (SEQ ID NO:1); Mink-B: tatggccttctcacccca (SEQ ID NO:2); Probe: tgtggcctacatctgctccaaccag (SEQ ID NO:3).

Antibodies. The following monoclonal antibodies were obtained from PharMingen (San Diego, Calif.): anti-CD8a-FITC and PE (Ly-2); anti-CD4-Cychrome and APC (L3T4); anti-HSA (CD24)-PE (M1/69); anti-CD3ε-FITC (145-2C11); anti-V$_\beta$5 (MR 9-4); anti-CD117 (2B8)-PE; anti-Ly-6A/E (Sca-1, D7)-Biotin; anti-CD8a (Ly-2); anti-CD4 (L3T4); anti-NK1.1 (PK136); anti-B220 (RA3-6B2); anti Gr-1 (RB6-8c5); anti-Mac-1 (M1/70); anti-CD19 (1D3); anti-CD49b/pan NK (DX5); anti-CD3 complex (17A2). Biotin-conjugated CD127 (IL-7Ra) (A7R34) was purchased from eBioscience (San Diego, Calif.). PE-Texas Red-conjugated CD8a was purchased from Caltag (Burlingame, Calif.). For immunoprecipitation and immunoblots, the following antibodies were used. MINK antibody was a gift from Dr. A. Kusumi and A. Zucconi. Anti-Nck was purchased from Transduction Laboratories (Lexington Ky.). Anti-CD3ε antibody was purchased from Santa Cruz.

Immunoblots and Immunoprecipitation. Protein lysates were made from T cells of 4-5 week old C57BL/6 mice (T cells were enriched by negatively selecting B cells, NK cells, granulocytes, macrophages, dendritic cells (DC)) using NP-40 lysis buffer (50 mM Tris, 150 mM NaCl, 1 mM EDTA, 1% NP-40, pH 7.4) supplemented with protease inhibitor (Sigma, St Louis, Mo.). Soluble fractions were assayed by the Bradford assay and boiled in 1×SDS loading buffer prior to electrophoresis. Gels were transferred to nitrocellulose membrane and blocked with 5% milk/TBS-T. Blots were probed with primary and secondary antibodies and developed with the enhanced chemiluminescence system. For immunoprecipitation, immune complexes were recovered using protein A/G-conjugated sepharose beads and followed the Western blot analysis procedure described above.

Immune complex kinase assay. 293 cells grown in DMEM with 10% FCS were seeded at a density of 2×10$^6$ cells in a 100 mm dishes for 16 hours and then transfected with 4-5 μg of DNA using Superfect transfection method (Qiagen, Valencia, Calif.). Jurkat T cells were maintained in RPMI supplemented with 10% FCS and transfected using the same way. Cells were lysed with lysis buffer (20 mM Tris (pH 7.4), 150 mM NaCl, 1 mM EDTA, 1 mM EGTA, 1% triton, 2.5 mM sodium pyrophosphate, 1 mM β-glycerolphosphate, 1 mM Na$_3$VO$_4$, 1 μg/ml leupeptin). The cell lysates (250 μg) were precleared by shaking with protein A/G sepharose beads for 1 h at 4° C. and immunoprecipitated with anti-HA antibody (for 293 cells). After overnight incubation, immune complexes were recovered with protein A/G beads and washed. Pellets were processed to either immunoblotting or kinase assay as previously described (Dan I et al., 2000, *FEBS Lett* 469:19-23).

Intrathymic injection. Double negative cells from MINK-deficient and control vector only mice were isolated by negative selection. 5000 cells/10 μl DN cells were injected into lightly irradiated (300 rads) Abb$^{-/-}$ KbDb$^{-/-}$ double knockout (DKO) hosts. FACS analysis was done seven days later. Control DKO is PBS (buffer) injected at 10 μl instead of cells into double deficient mice (not irradiated).

Example 2

Generation of Virus

A previously described protocol (Rubinson D A et al., 2003, *Nat Genet.* 33:401-6) was used, with minor modifications, to generate virus bearing sequences to generate RNAi against MINK. Briefly, 293 T cells were maintained in DMEM with 10% FCS/2 mM L-glutamine/100 units/ml penicillin/100 μg/ml streptomycin (all from Gibco/BRL, Grand Island, N.Y.). 293 T cells (5-7×10$^6$ cells) were transfected by calcium phosphate precipitation with 4 μg VSV-G, 4 μg of RSV-REV, 4 μg of pMDL g/p RRE and 8 μg of lentivirus vector (pLentiLox 3.7, kindly provided by C. Dillon) with RNAi sequences against Mink or transfected as an empty vector. The oligonucleotide sequences to generate RNAi against Mink were as follows:

```
                                              (SEQ ID NO: 4)
5'-tgtactctcaccatcgcaatttcaagagaattgcgatggtgagagta
ctttttttc-3';

(SEQ ID NO: 5)
5'-tcgagaaaaaagtactctcaccatcgcaattctcttgaaattgcgat
ggtgagagtaca-3'.
```

Medium was replaced 4 h post-transfection. Thirty-six hours post-transfection, supernatants were collected and filtered through a 0.45 μm syringe filter. The filtered supernatant was concentrated by ultracentrifugation for 1.5 h at 25,000 rpm (Sorvall Ultra Pro80), and virus pellet was re-suspended in phosphate-buffered saline (15-100 μl).

Example 3

Generation of MINK-Deficient (Knock-Down) Mice

BM cells were isolated from healthy mice (C57BL/6, female, 4-5 weeks) and lineage positive cells were depleted with anti-CD4, anti-CD8, anti-CD3, anti-Grl, anti-Mac1, anti-CD19, anti-DX followed by sheep anti-rat IgG-conjugated immunomagnetic beads (Dynal, Oslo, Norway). For MINK-deficient/OTII and MINK-deficient/HY BM chimeric mice, hematopoietic stem cells (HSC) from OTII mice and HY mice were used, respectively. The remaining cells were stained and sorted for sca-1$^+$ c-kit$^+$ cells by high speed cell sorting (Moflo-MLS, Cytomation, Fort Collins, Colo.). These hematopoietic stem cells were infected with virus at an MOI of ~25-60 by spin infection (1200 g×1.5 h at 25° C.) with polybrene (final concentration, 9 μg/ml). Cells were incubated for 1 h at 37° C. before 75% of supernatants were removed. Cells were sorted for GFP$^+$ after 24-36 hours. Cells were maintained during infection and incubation in IMDM, 20% FCS, L-glutamine, Pen/Strep, Na-pyruvate, non-essential amino acids with cytokines (50 ng/ml SCF; 50 ng/ml Flt3L; 20 ng/ml IL-7; 20 ng/ml IL-6). GFP$^+$ HSC cells (3-5×

10⁴) were injected into irradiated (400 rads) Rag2⁻/⁻ mice, and reconstituted mice were analyzed at various time points.

Example 4

Expression of MINK During Thymocyte Development

Serial analysis of gene expression (SAGE) and real-time PCR analysis of genes expressed in developing thymocytes were combined to define genes that might contribute to thymocyte selection according to expression in pre- and post-selection thymocyte subpopulations and functional activity. McCarty N et al. (2004) *Proc Natl Acad Sci USA* 101:9339-44.

FIG. 2A shows MINK expression in bone marrow and thymocyte subpopulations as examined by real-time PCR (Taqman). The indicated thymic subpopulations isolated from 4-5 wk old C57BL/6 mice were sorted to >98% purity. DP (CD4⁺CD8⁺) thymocytes were obtained from Abb⁻/⁻KbDb⁻/⁻ mice. Data shown is representative of multiple independent experiments. BM: Bone Marrow, DN: Double Negative (CD4⁻CD8⁻), DP: Double Positive, PRO: Progenitor cells for SP, SP: Single Positive (CD4⁺CD8⁻ and CD8⁺CD4⁻).

Figure 2B:
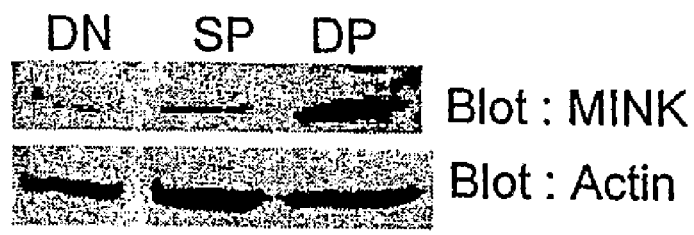
FIG. 2B shows a western blot of MINK expression in double negative (DN), single positive (SP), and double positive (DP) cell populations.

FIG. 2B shows MINK protein expression in each thymic subset. Cell lysates (50-60 μg protein/lane) from DN, SP, and DP were used for immunoblot analysis. Blots were developed with antibodies to either MINK or actin and data shown are representative of three independent experiments.

This example shows that MINK gene expression increased about 20-fold during the transition from double negative thymocytes to double positive thymocytes, before attenuation in post-selection CD4 and CD8 SP thymocytes. These PCR-based RNA measurements, confirmed by Northern analysis, were consistent with a robust increase in MINK protein expression in DP thymocytes.

Example 5

MINK Deficiency and Thymocyte Development

To generate mice containing a lymphoid-specific deficiency of MINK gene expression, purified GFP⁺ hematopoietic stem cells (HSC) from bone marrow (BM) infected with lentivirus containing either GFP-MINK RNAi-inducing small hairpin RNA (shRNA) or GFP-vector only (control) for 48 h were injected into irradiated Rag2⁻/⁻ mice. Eight weeks later, 75-90% of thymocytes from both groups expressed lentiviral GFP.

Figure 3A:
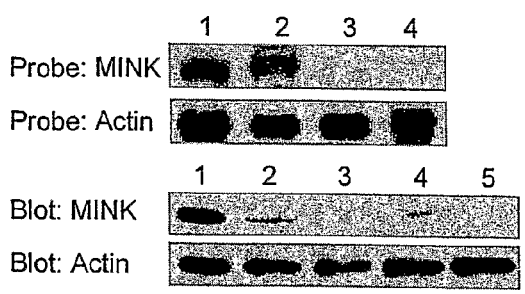
FIG. 3A shows a northern blot and western blot analysis of MINK expression in MINK knockdown (KD) mice.

MINK RNA or protein was easily detected in thymocytes and splenocytes from mice reconstituted with GFP lentiviral vector-infected (control) HSC, but was not detectable in cells from MINK-RNAi-infected HSC (knock-down). BM chimeric mice were generated as described in Example 3, and RNA amounts in tissues were analyzed with either MINK or actin probe. The upper panel of FIG. 3A shows RNA blot analysis of control spleen (lane 1), control thymus (lane 2), MINK-deficient spleen (lane 3), and MINK-deficient thymus (lane 4). The lower panel of FIG. 3A shows immunoblot analysis of brain cortex (lane 1), control thymus (lane 2), MINK-deficient thymus (lane 3), control spleen (lane 4), and MINK-deficient spleen (lane 5). Brain tissues (lanes 1) were used as a positive control. Lysates from GFP⁺-sorted thymocytes or splenocytes (lanes 2-5) are shown. Data is representative of five independent experiments.

Figure 3B:
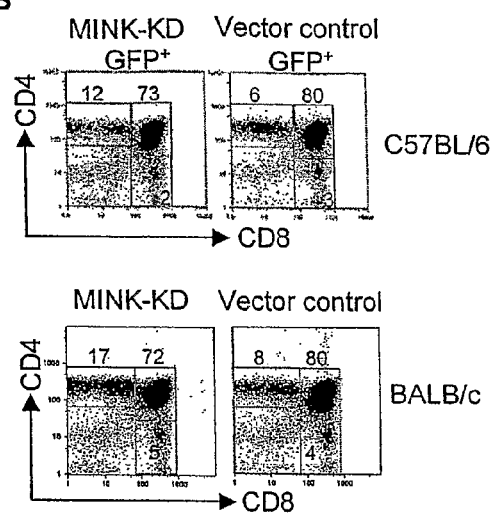
FIG. 3B shows FACS analyses of cell surface expression of CD4 and CD8 in thymic subpopulations in MINK KD and control C57BL/6 and BALB/c mice.
Figure 3C:
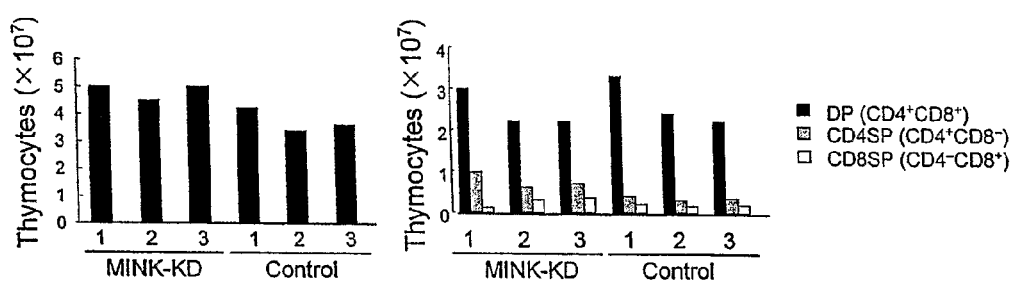
FIG. 3C shows two graphs comparing numbers of green fluorescent protein positive (GFP$^+$) thymocytes in MINK-KD mice and control mice. The left panel represents total cellularity, and the data in the right panel are divided among thymocyte subpopulations. The y-axis represents relative numbers of thymocytes ($\times 10^7$); the x-axis represents MINK-KD mice (left) and control mice (right).

CD4 SP thymocyte numbers were increased in MINK-deficient mice by 2-3-fold (i.e., 1×10⁷ in MINK-deficient vs. ~5×10⁶ in control thymus). FIG. 3B shows the results of FACS analysis of cell surface expression of CD4, CD8 in MINK-deficient vs. control vector only mice (upper panel) and BALB/c (lower panel). Cells were gated on GFP⁺ thymocytes from MINK-deficient and control mice. (MINK-deficient thymus, 5×10⁷; LN/spleen, 13×10⁷; vector control: thymus, 4.2×10⁷; LN/spleen, 7.5×10⁷) (FIG. 3B). These measurements were associated with an increase in thymic cellularity, as shown in FIG. 3C. The numbers of GFP⁺ thymocytes (left) and thymic subpopulations (right) from individual MINK-deficient or control vector only mice are shown.

Figure 3D:
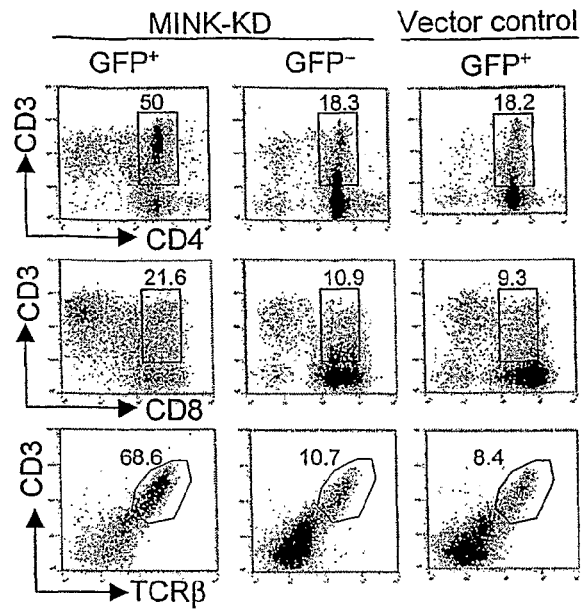
FIG. 3D shows FACS analyses of cell surface expression of CD4, CD8, CD3, and TCRβ in thymic subpopulations in MINK KD and control C57BL/6 and BALB/c mice.

Increased production and accumulation of mature thymocytes in MINK-deficient mice were most clearly indicated from analysis of TCRβ and CD3 expression. Approximately 70% of MINK-deficient thymocytes were TCRβ$^{hi}$CD3$^{hi}$, compared to 8-10% TCRβ$^{hi}$CD3$^{hi}$ thymocytes in control thymuses. Cells were gated on GFP⁺ or GFP⁻ thymocytes from MINK-deficient mice and on GFP⁺ thymocytes from controls, and the percentage of gated cells that fell within the indicated region are indicated in FIG. 3D. Data shown in FIG. 3D are representative of four independent experiments. Although purified GFP⁺ cells were transferred to irradiated Rag2⁻/⁻ mice, thymocytes from reconstituted mice contained a 10-25% GFP⁻ subpopulation, possibly due to the low activity of the CMV viral promoter for GFP.

Figure 3E:
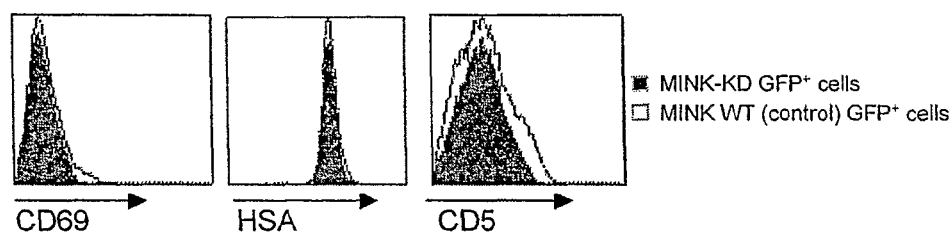
FIG. 3E shows a histogram profile of CD69, HSA, and CD5 surface expression on DP thymocytes from MINK-KD and control mice.

Although the numbers of SP CD4 cells was somewhat increased in MINK-deficient mice, positive selection of DP thymocytes was not obviously impaired compared to control mice, as judged by the expression of CD69, HSA and CD5 on CD3⁺ DP thymocytes from MINK-deficient and control mice. Superimposed histogram profiles in FIG. 3E show surface expression of CD69 (left panel), HSA (CD24; middle panel), and CD5 (right panel) on DP thymocytes from MINK-deficient (gray) or control vector only mice (white).

Figure 4A:
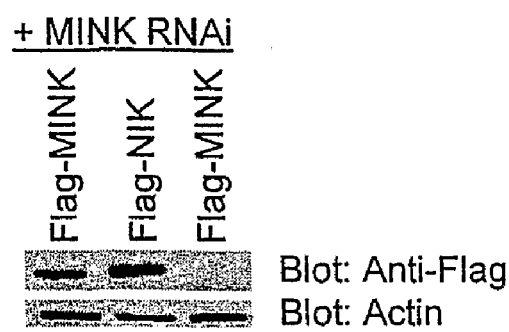
FIG. 4A shows a western blot analyzed with anti-Flag (for MINK expression, top panel) or anti-actin (bottom panel).
Figure 4B:
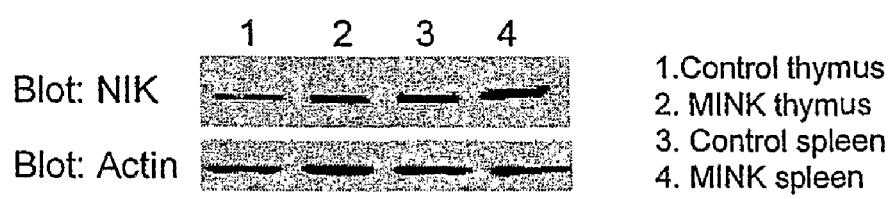
FIG. 4B shows a western blot analyzed with anti-NIK (top panel) or anti-actin (bottom panel) of samples from MINK-KD and control thymus and spleen.
Figure 4C:
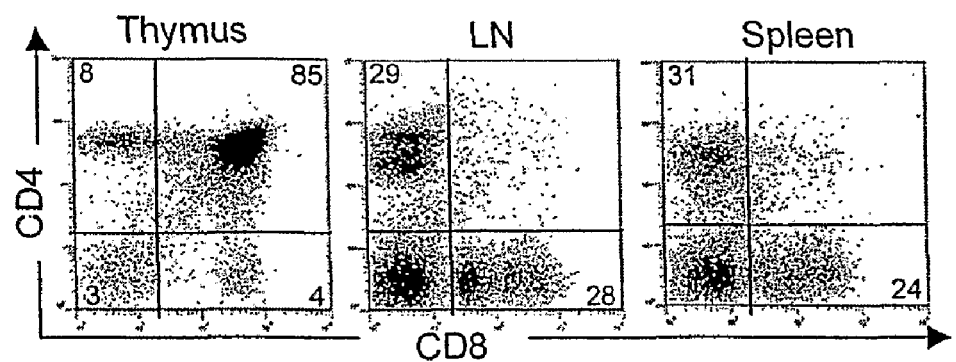
FIG. 4C shows FACS analysis of CD4 and CD8 surface markers in cells of thymus, lymph node (LN), and spleen.

The specificity of MINK RNAi-dependent inhibition was confirmed in primary T cells and T cell lines transfected with Flag-tagged MINK and Flag-tagged NIK. Jurkat T cells (5×10⁷) were transfected with Flag-MINK or Flag-NIK. After 24 hours of transfection, MINK lentivirus RNAi was infected or not transfected into Jurkat T cells. 48 hours post-infection, GFP cells were sorted and cell lysates (25 μg/lane) were made. NIK and MINK are highly homologous at nucleotide sequence level (75%). The RNAi target sequence of MINK is 5'-acacttacgggcggatca-3' (SEQ ID NO:1) and the sequence of NIK in the same region differs by only three nucleotides 5'-acacgtacggaaggatca-3' (SEQ ID NO:6). The amount of protein was determined by immunoblotting. As shown in FIG. 4A, MINK RNAi only inhibited Flag-tagged MINK. Thus RNAi-inducing shRNA corresponding to a MINK hairpin RNA sequence inhibited MINK protein expression but not expression of the highly homologous NIK protein, which shares 14 of the 16 nucleotides with the targeted MINK RNAi sequence. This was consistent with unaltered amounts of NIK protein expression in thymocytes from MINK-deficient mice (i.e., Rag2⁻/⁻ mice reconstituted with hematopoietic stem cells infected with MINK-RNAi) and GFP-control mice (i.e., Rag2⁻/⁻ mice reconstituted with hematopoietic stem cells infected with RNAi vector only) (FIG. 4B). The specificity of MINK-RNAi thymocyte phenotype in vivo was also confirmed by comparison with the thymocyte phenotype after infection of lentiviral vectors containing a random RNAi sequence (FIG. 4C).

Figure 3F:
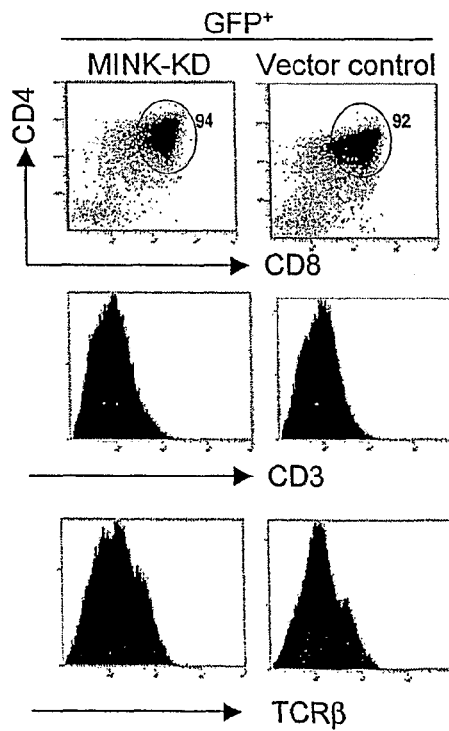
FIG. 3F shows (top row) FACS analyses of CD4 and CD8 surface GFP$^+$ cells in MINK-KD and control mice; (middle row) histograms of CD3 surface marker; and (bottom row) histograms of TCRβ surface marker.

GFP⁺ thymocytes that arose 1 week after intrathymic transfer of MINK-deficient or control DN cells into MHC-deficient thymus were indistinguishable in terms of total numbers and surface expression of CD4, CD8, CD3 and TCRβ (FIG. 3F). This suggests that MINK deficiency had no detectable impact on MHC-independent homeostatic expansion associated with the transition to DP thymocytes from DN precursors and MHC-TCR interactions with developing thymocytes were essential for expression of the abnormal thymocyte phenotype of MINK-deficient cells. Phenotypes include increased CD3 and TCRβ expression on thymocytes and increased numbers of SP CD4 thymocytes. When FACS-purified GFP$^+$ cells (>98% GFP$^+$) were transferred to irradiated Rag2$^{-/-}$ mice, reconstituted thymus routinely contained 10-25% GFP$^-$ cells, possibly due to relatively low activity of the CMV viral promoter in the bicistronic (GFP-RNAi) vector (Rubinson D A et al., 2003, *Nat Genet.* 33:401-6). Importantly, the phenotype of GFP$^-$ thymocyte fraction from MINK-deficient mice was indistinguishable from that of thymocytes from vector-only controls, i.e., GFP expression correlated with altered thymocyte development and presumably, RNAi activity of the bicistronic vector (FIG. 3C).

Example 6

Figure 5A:
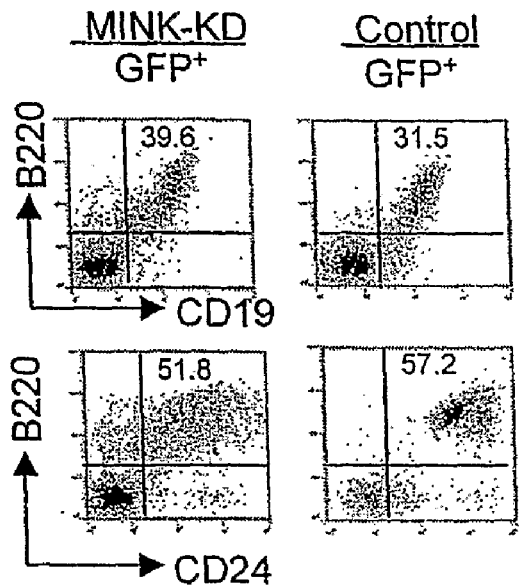
FIG. 5A shows FACS analyses of splenic B cell subpopulations in MINK-KD (left panels) and control (right panels) mice. Top row: the y-axis represents the B220 surface marker and the x-axis represents the CD19 surface marker. Bottom row: the y-axis represents the B220 surface marker and the x-axis represents the CD24 surface marker.

MINK-Deficient Mice Have Normal Peripheral B Cell Development and T Cell Reactivity Analysis of splenic B cell development in MINK-deficient and control chimeras did not reveal an obvious defect, as judged by numbers and proportion of B220$^+$CD19$^+$ and B220$^+$CD24$^+$ B cell subpopulations (FIG. 5A). Splenocytes from lentiviral-infected BM chimeric MINK-deficient and control mice were isolated and stained with anti-B220, anti-CD19, and anti-CD24 surface antibodies to distinguish subpopulations of B cells. Cells in the indicated profiles are GFP$^+$. Data shown are representative of three independent experiments.

Figure 5B:
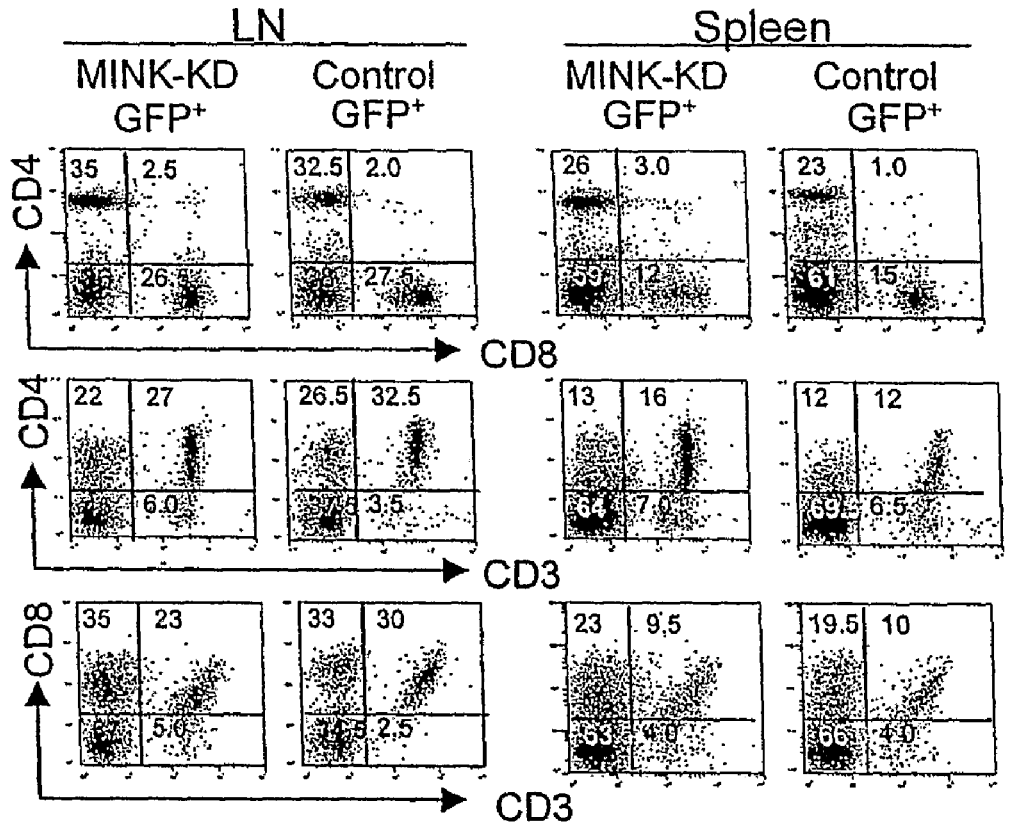
FIG. 5B shows FACS analyses of LN and spleen cell subpopulations in MINK-KD (columns 1 and 3) and control (columns 2 and 4) mice. Top row: the y-axis represents the CD4 surface marker and the x-axis represents the CD8 surface marker. Middle row: the y-axis represents the CD4 surface marker and the x-axis represents the CD3 surface marker. Bottom row: the y-axis represents the CD8 surface marker and the x-axis represents the CD3 surface marker.

The proportions of peripheral CD3$^+$ CD8$^+$ and CD3$^+$ CD4$^+$ cells in MINK-deficient mice and controls were similar (FIG. 5B). Splenocytes and LN from lentiviral-infected BM chimeric MINK-deficient and control mice were isolated and stained with anti-CD3, anti-CD4, and anti-CD8 surface antibodies to distinguish subpopulations of T cells. All cells were gated on live GFP$^+$ cells, and the percentage of cells is indicated in each quadrant. These data are representative of three independent experiments.

Figure 5C:
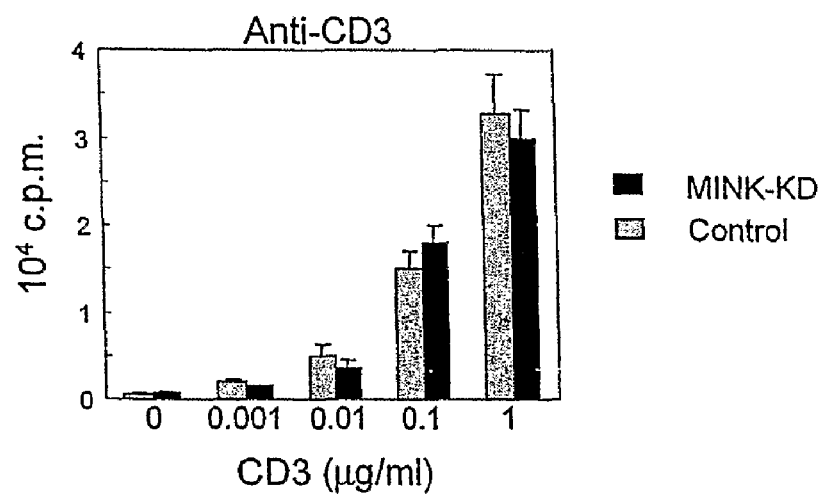
FIG. 5C is a bar graph depicting proliferation responses of purified double positive thymocytes from MINK-KD (black bars) and control (gray bars) mice. The y-axis represents counts per minute (CPM), and the x-axis represents anti-CD3 (μg/ml).
Figure 5D:
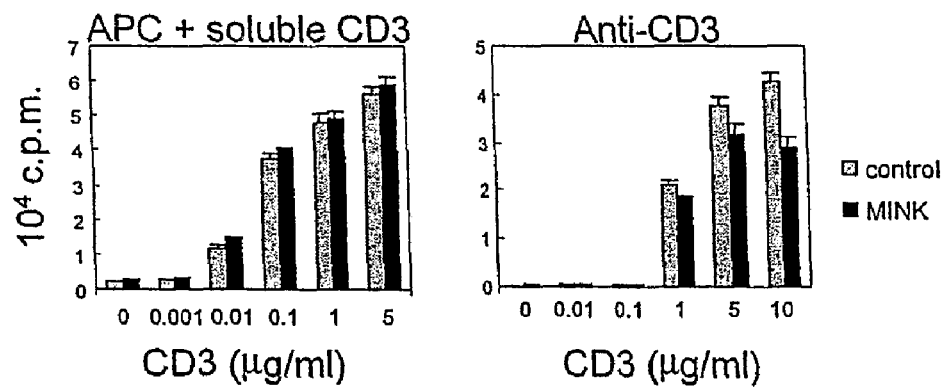
FIG. 5D is a pair of bar graphs depicting proliferation responses of peripheral T cells from MINK-KD (black bars) and control (gray bars) mice. In each panel the y-axis represents counts per minute (CPM), and the x-axis represents anti-CD3 (μg/ml). Left panel: stimulation with APC plus soluble anti-CD3. Right panel: stimulation with immobilized anti-CD3.

Analysis of proliferation responses with purified double positive T cells from control mice or MINK-deficient demonstrated that the response of MINK-deficient DP cells (FIG. 5C) and peripheral T cells (FIG. 5D) to anti-CD3ε alone or activated dendritic cells (DC) did not differ from GFP control cells. Therefore MINK deficiency does not have an obvious effect on the response of T cells to antibody-dependent CD3ε ligation. Purified peripheral T cells from control mice (grey bars) or MINK-deficient (black bars) were incubated with DC plus soluble anti-CD3ε (at the indicated amounts) or plate bound anti-CD3ε and CD28 in 96-well plates for 48 hours. Purified GFP$^+$ cells after sorting were used to measure proliferation. Results shown in FIG. 5C and FIG. 5D are representative of two independent experiments.

Example 7

MINK is Necessary for Negative Selection and Not Positive Selection

In this example we investigated whether the thymic phenotype associated with deficient expression of MINK reflected impaired negative selection, as judged by deletion of autoreactive thymocytes specific for endogenous Mtv superantigen, a MHC class II-binding peptide, or MHC class I-binding peptide.

Figure 6A:
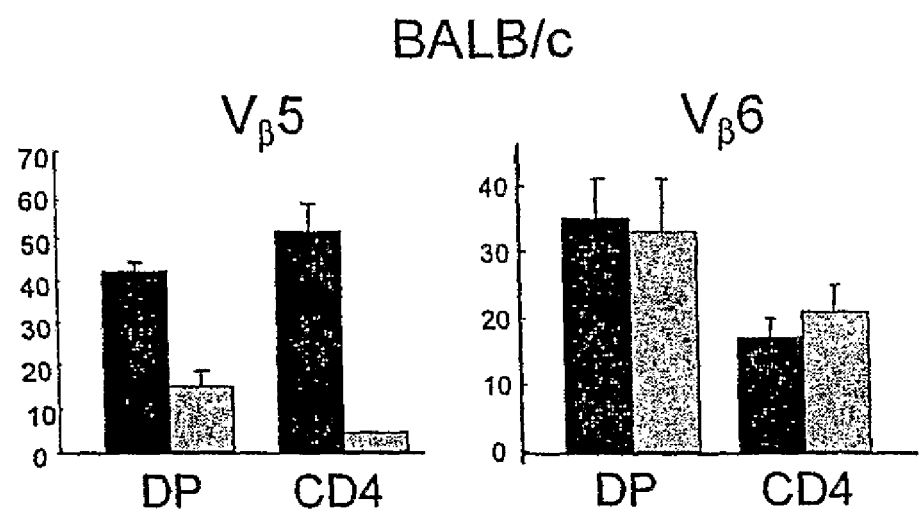
FIG. 6A shows two graphs depicting numbers of $V_\beta 5$ and $V_\beta 6$ positive cells (left and right panels, respectively) in double positive (DP, left sides) and CD4 positive (right sides) cells. The y-axis represents numbers of cells$\times 10^5$.
Figure 6B:
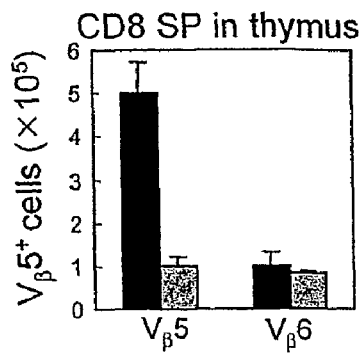
FIG. 6B is a bar graph depicting number of $V_\beta 5^+$ thymocytes in MINK-KD (black bars) and control (gray bars) mice.
Figure 6C:
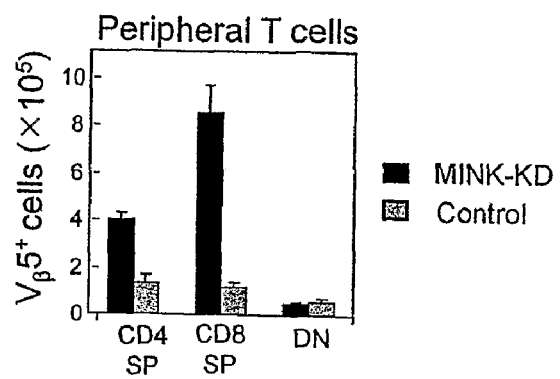
FIG. 6C is a bar graph depicting number of $V_\beta 5^+$ peripheral T cells in MINK-KD (black bars) and control (gray bars) mice.

A comparison of Mtv-9-dependent deletion of V$_β$5$^+$ thymocytes in MINK-deficient and control mice revealed a 5-6 fold increase of V$_β$5$^+$ CD4$^+$ thymocytes in MINK-deficient mice and a 2 fold increase in V$_β$5$^+$ DP thymocytes compared to control thymocytes (FIG. 6A), whereas the numbers of V$_β$6$^+$ thymocytes were unchanged. Increased numbers of MINK-deficient V$_β$5$^+$ thymocytes were also associated with increased V$_β$5$^+$ CD8$^+$ single positive thymocytes (FIG. 6B) and resulted in increased V$_β$5$^+$ peripheral T cells (FIG. 6C). Because Mtv-9-dependent deletion of V$_β$5$^+$ thymocytes is relatively inefficient in C57BL/6 mice, the impact of MINK deficiency was analyzed in BALB/c HSC chimeras, where I-E/Mtv-dependent interactions with V$_β$5$^+$ thymocytes allow more robust deletional effects (FIG. 6A). HSC from female BALB/c mice infected with MINK RNAi lentivirus or control GFP lentivirus were sorted for GFP$^+$ cells before transfer into irradiated BALB/c-Rag2$^{-/-}$ female mice followed by analysis of GFP$^+$ thymocytes 6 weeks later. The mean number of TCR V$_β$5$^+$ or TCR V$_β$6$^+$ DP and SP thymocytes is shown in FIG. 6A. There were very small numbers (3×10$^5$ V$_β$5$^+$ CD4/thymus) of Vβ5$^+$ CD4 SP thymocytes in control Rag2$^{-/-}$ BALB/c chimeras generated with HSC infected with GFP-only vectors. In contrast, MINK-KD thymuses contained about 5×10$^6$ V$_β$5$^+$ CD4 SP cells/thymus, a 15-fold increase. The levels of control V$_β$6+ CD4 thymocytes (~1.8×10$^6$) were unchanged by MINK deficiency in the BALB/c HSC chimeras (FIG. 6A). A MINK-dependent defect in Mtv-associated deletion of V$_β$5$^+$ cells was more striking in IE$^+$ BALB/c-Rag2$^{-/-}$ mice after reconstitution with HSC infected with either MINK or control lentiviral vectors (FIG. 6A).

Figure 6D:
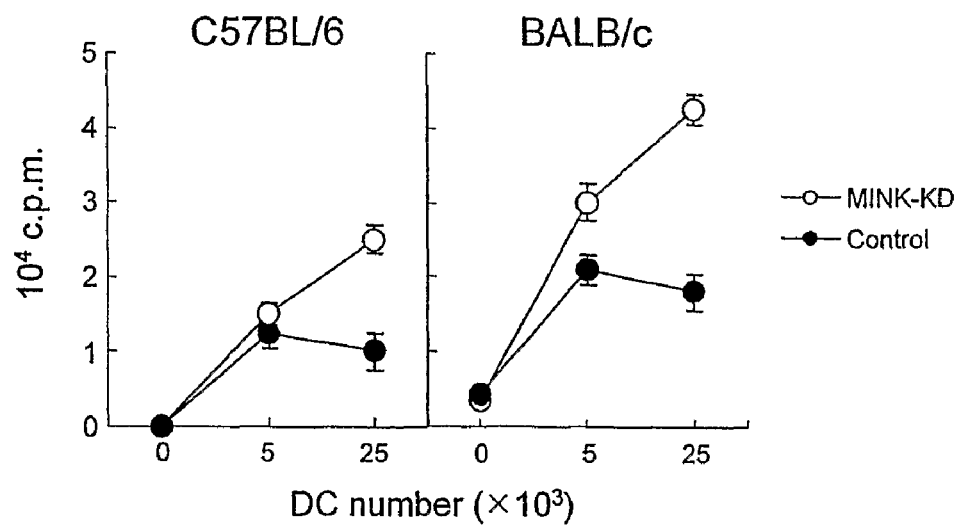
FIG. 6D is a pair of graphs depicting proliferation of GFP$^+$ CD4$^+$ CD25$^-$ cells from MINK-deficient and control chimeras following 48 hours of incubation in the presence of the indicated number of dendritic cells (DC). Left panel: C57BL/6 MINK-KD (open symbols) and control (filled symbols); Right panel: BALB/c MINK-KD (open symbols) and control (filled symbols)

Examination of reactivity of peripheral CD4 cells from MINK-deficient B6 and BALB/c HSC chimeras in autologous mixed lymphocyte responses (AMLR) showed a 3-fold increase in the proliferative response, consistent with export of autoreactive CD4 SP thymocytes to the periphery, where they were detected 4 weeks after thymocyte development in these Rag2-deficient HSC chimeras (FIG. 6D).

Figure 6E:
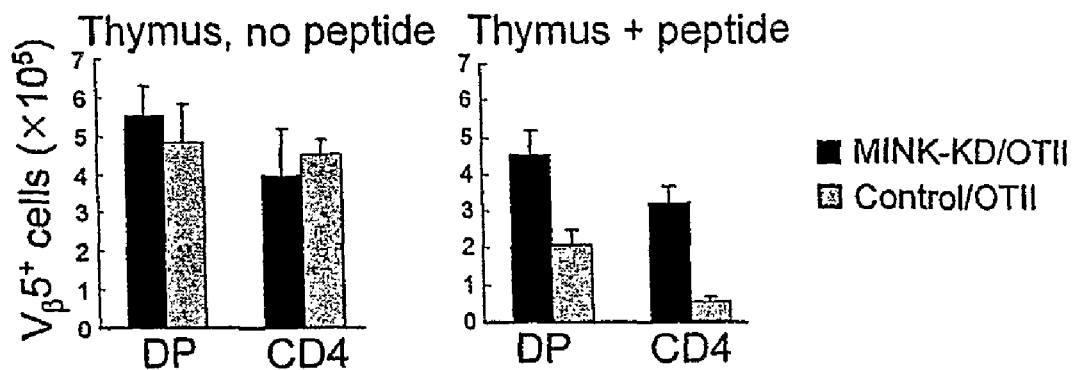
FIG. 6E shows a graph depicting numbers of $V_\beta 5^+$ cells in thymus with no ova peptide treatment (left panel) and thymus with peptide treatment (right panel) in DP (left sides of panels) and CD4 (right sides of panels) positive cells. The x axis represents numbers of $V_\beta 5^+$ cells$\times 10^4$ and the x axis represents DP and CD4 markers. Cells from MINK-KD mice and from control mice are represented by black bars gray bars, respectively.
Figure 6F:
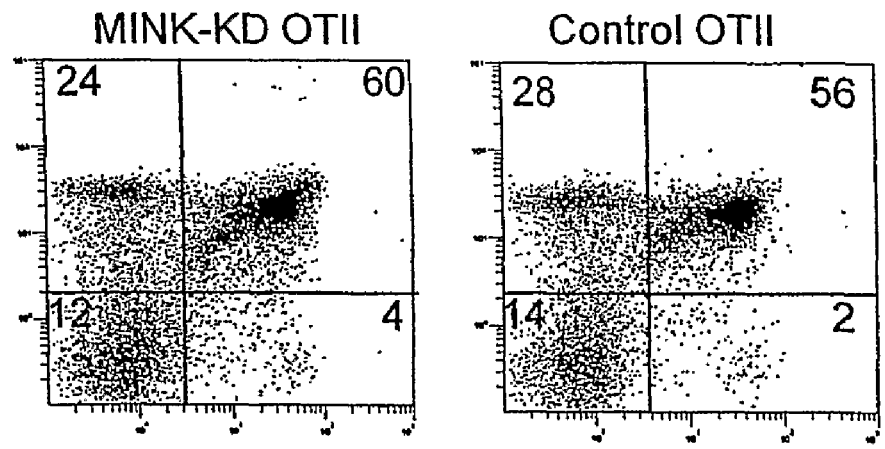
FIG. 6F is a pair of graphs depicting thymic profiles in MINK-KD OTII (left panel) and control OTII (right panel) mice according to FACS analysis. Cells were stained for surface expression of CD4, CD8 and gated on GFP$^+$ cells. Percentages of gated cells in each quadrant are indicated.
Figure 6G:
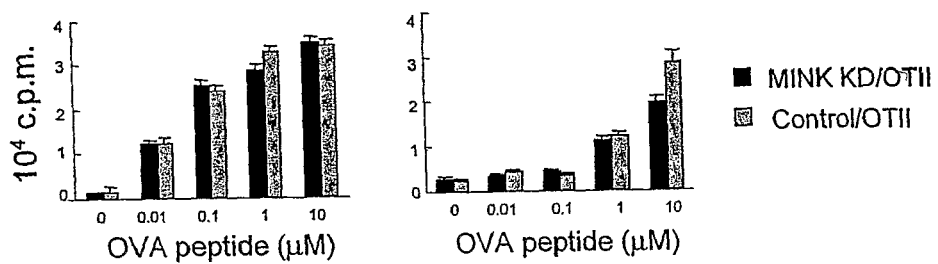
FIG. 6G is a pair of bar graphs depicting response of T cells from MINK-deficient-OTII mice to OVA peptide in vitro. CD4$^+$ GFP$^+$ cells from MINK-deficient-OTII or GFP control OTII were incubated with the indicated concentrations of OVA peptide with anti-CD40 activated DC (left panel) or splenocytes (right panel) for 48 hours before measurement of the proliferative response.

Further analysis of the potential impact of MINK deficiency on negative selection utilized transgenic (tg) mice that express the class II restricted OTII TCR tg (Bouillet et al., 2002, *Nature* 415:922-926). HSC cells from OTII tg mice were infected with MINK-RNAi-GFP lentivirus before sorting of GFP+ cells and transfer into irradiated Rag2$^{-/-}$ mice. After eight weeks, MINK KD/OTII mice or control KD/OTII mice were injected with 1 mg OVA peptide/saline or saline alone, sacrificed 72 hr later, and thymocytes were analyzed after staining with antibodies to CD4, CD8, TCR V$_β$5 and GFP expression by FACS. Results representative of three independent experiments are shown in FIG. 6E. The left panel of FIG. 6E shows arithmetic mean of total number of GFP$^+$ TCR V$_β$5$^+$ CD4$^+$ CD8$^+$ (DP) or thymocytes. The right panel of FIG. 6E shows numbers of percentage of V$_β$5$^+$ DP or V$_β$5$^+$ CD4 SP thymocytes after OVA peptide injection, three mice for each group. Injection of soluble OVA peptide into GFP control/OTII mice led to elimination of ~75% of Vβ5$^+$ SP CD4 and ~45% of DP thymocytes compared with uninjected mice. In contrast, the numbers of V$_β$5$^+$ thymocytes in injected and uninjected MINK-KD OTII mice were not distinguishable from each other or wt-OTII thymus. The thymocyte deletional profile (greater reduction in SP thymocytes compared with DP thymocytes) is consistent with a cytokine-independent effect (Zhan et al., 2003, *Proc Natl Acad Sci U.S.A* 100, 1197-1202) because MINK expression did not contribute to positive selection but was essential for peptide-induced thymocyte deletion (FIG. 6E and FIG. 6F). The inability of OVA peptide to delete $V_\beta 5^+$ cells in MINK-deficient mice did not reflect a blunted or attenuated response of MINK-deficient CD4 cells to OVA peptide, which was indistinguishable from the response of control CD4 cells in vitro (FIG. 6G). Taken together, these data demonstrate the requirement of MINK for negative selection.

Figure 6H:
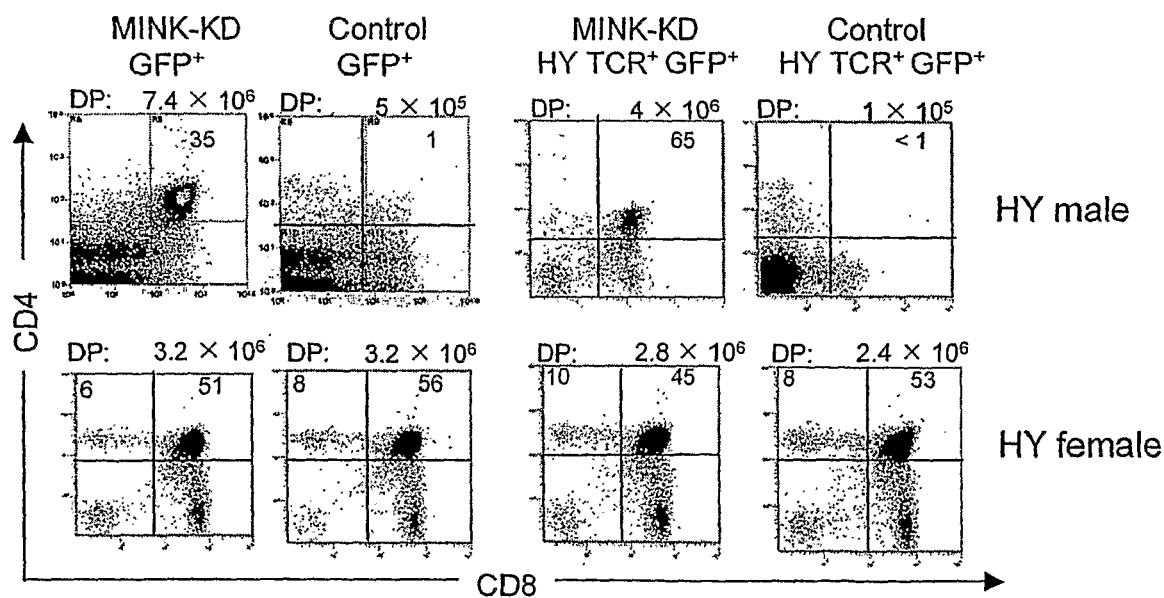
FIG. 6H shows FACS analyses of HY TCR$^+$ thymocytes in MINK-KD and control mice. Y-axes represent CD4 surface marker, x-axes represent CD8 surface marker. The top row of panels represents HY male mice; the bottom row represents HY female mice.
Figure 6I:
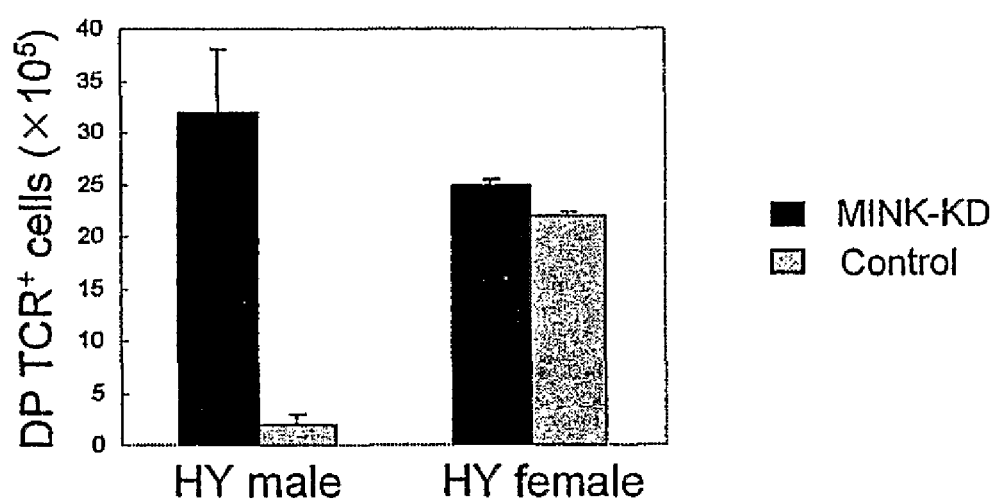
FIG. 6I shows a graph depicting numbers of DP thymocytes in HY TCR female and male mice. The y-axis represents cell number×10⁵. The x-axis represents MINK-KD (black bars) and control (gray bars) male (left columns) and female (right columns) mice.
Figure 6J:
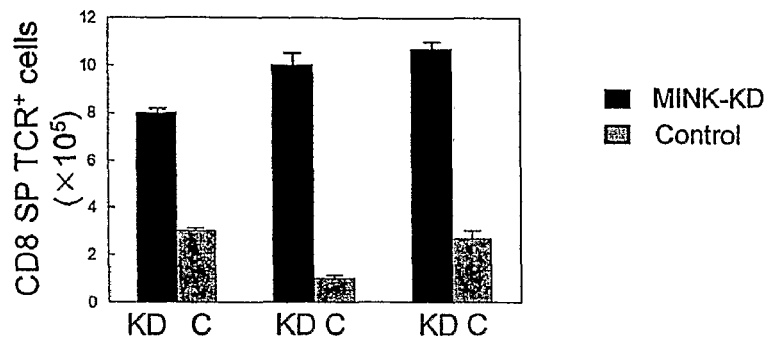
FIG. 6J is a bar graph depicting the numbers of CD8 SP TCR⁺ cells from individual MINK-KD HY TCR male (black bars) and control vector HY TCR male (gray bars) mice.
Figure 6K:
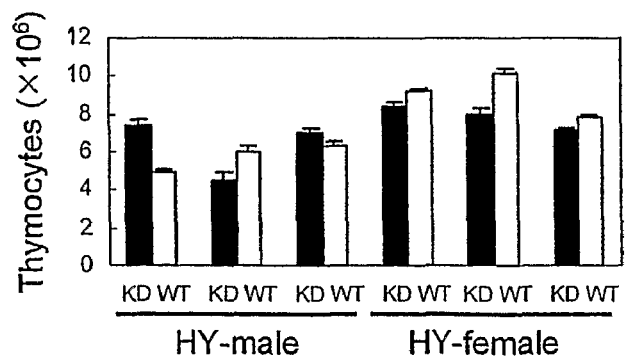
FIG. 6K is a bar graph depicting numbers of total thymocytes from individual MINK-KD HY-male, MINK-KD HY-female mice, control (WT) HY male, and control HY female mice.

We then investigated the impact of MINK deficiency on negative selection of HY TCR$^+$ (B6.2.16 TCR) DP thymocytes specific for a peptide from the HY male antigen associated with H-2 D$^b$ class I MHC. HSC from male HY TCR tg mice or female HY TCR tg mice infected with MINK RNAi lentivirus or control lentivirus were sorted for GFP fraction and transferred into irradiated Rag2$^{-/-}$ male or female mice followed by analysis of thymus two months later. Representative dot plots of GFP$^+$ thymocytes (left panel) and HY TCR thymocytes (right panel) from MINK-KD or GFP control mice are shown in FIG. 6H. Data shown is representative of three independent experiments. Since the HY antigen is expressed in thymus (Kisielow et al., 1988, Nature 335, 730-733), most autoreactive B6.2.16 thymocytes in HY-male (C57BL/6) mice are deleted at the DP (CD4$^+$ CD8$^+$) stage (Teh et al., 1990, Immunol 1, 1-10). Thus, GFP vector control HY TCR tg$^+$ male mice contained virtually undetectable levels of HY TCR$^+$ DP thymocytes, while MINK-deficient males contained substantial numbers of HY TCR$^+$ DP cells that are equivalent to the numbers present in the thymus of female MINK-KD or vector control mice (FIGS. 6H, 6I, 6J). The numbers of DP (TCR$^+$) thymocytes from individual MINK-KD/HY/male, MINK-KD/HY/female, control vector/HY male or control vector/HY female mice were determined. Bars indicate one standard error of the mean. Since the numbers of HY TCR$^+$ DP and SP thymocytes in MINK-deficient and control female mice were similar (FIG. 6H and FIG. 6K), the impact of MINK on negative selection of developing thymocytes does not extend to positive selection (FIG. 6H).

Example 8

Analysis of TCR-Linked MINK-Dependent Signaling In Vitro

Figures 7A, 7B:
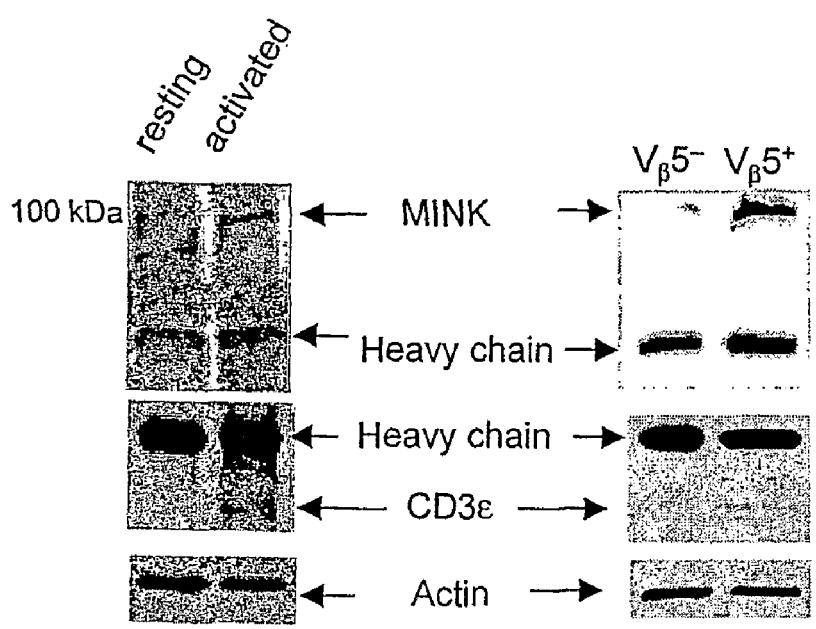
FIG. 7A shows a western blot of anti-Nck immunoprecipitates from resting (left panels) and activated (right panels) T cells. Top panels: anti-MINK; middle panels: anti-CD3ε; bottom panels: anti-actin.
FIG. 7B shows a western blot of anti-Nck immunoprecipitates from $V_\beta 5^-$ (left panels) and $V_\beta 5^+$ (right panels) thymocytes. Top panels: anti-MINK; middle panels: anti-CD3ε; bottom panels: anti-actin.
Figure 7C:
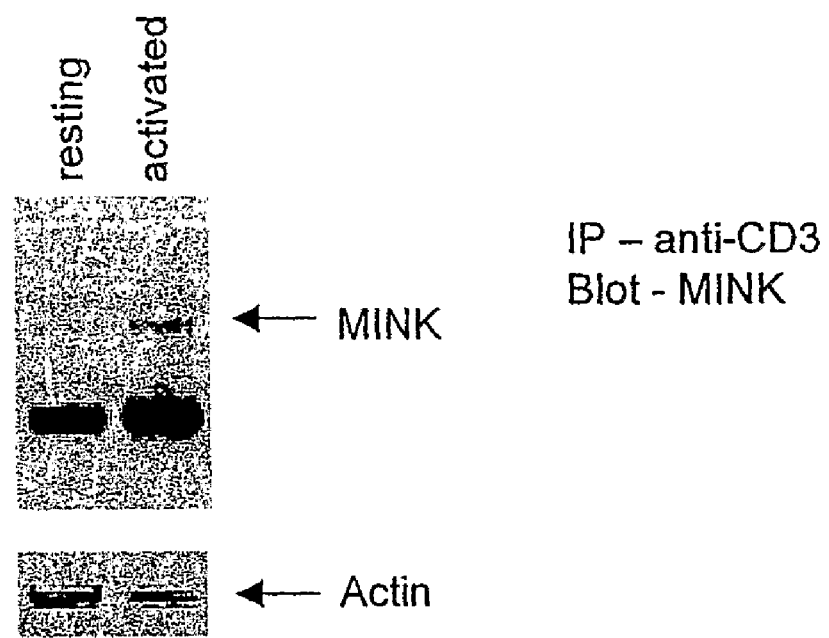
FIG. 7C shows a western blot of anti-CD3 immunoprecipitates from resting (left panel) and activated (right panel) non-T-cell depleted splenocytes, probed for MINK or actin.

Three independent selection models in Example 7 implicate MINK in negative but not positive selection. MINK is a member of the Nck-interacting kinase (NIK) subfamily of germinal center kinases (GCK), and thus may interact with the Nck adaptor protein through binding of proline-rich regions of MINK to SRC homology 3 (SH3) domains of Nck. We therefore asked whether TCR ligation might induce association of MINK with Nck. Immunoprecipitation with anti-Nck followed by Western blot analysis with anti-MINK showed that antibody-dependent CD3 ligation leading to T cell activation promoted association of MINK and Nck (FIG. 7A). Since Nck has been suggested to bind to exposed sequences of CD3ε chains after robust TCRαβ engagement (Gil et al., 2002, Cell 109, 901-912; Davis, 2002, Cell 110, 285-287), lysates were also blotted with anti-CD3ε. Precipitated Nck/MINK complexes from activated but not resting T cells also contained CD3ε (FIG. 7A). The same cell lysates were immunoprecipitated with anti-CD3 followed by western blot analysis with anti-MINK to detect potential recruitment of MINK to the TCR via NIK. The CD3-associated complex from activated but not resting T cells contained MINK protein according to Western blotting (FIG. 7C). Analysis of Vβ5$^+$ and Vβ5$^-$ thymocytes after injection of OVA peptide into OTII mice also showed association of MINK and Nck in Vβ5$^+$ thymocytes (FIG. 7B). Although Nck has been reported to bind to a motif in the CD3ε chain that is revealed upon TCR ligation (Gil et al., 2002, Cell 109, 901-912), additional experiments are performed to determine whether the tripartite association of MINK-Nck-CD3ε in activated T cells reflects Nck recruitment to the CD3ε chain following high affinity TCR engagement in vivo.

Figure 8A:
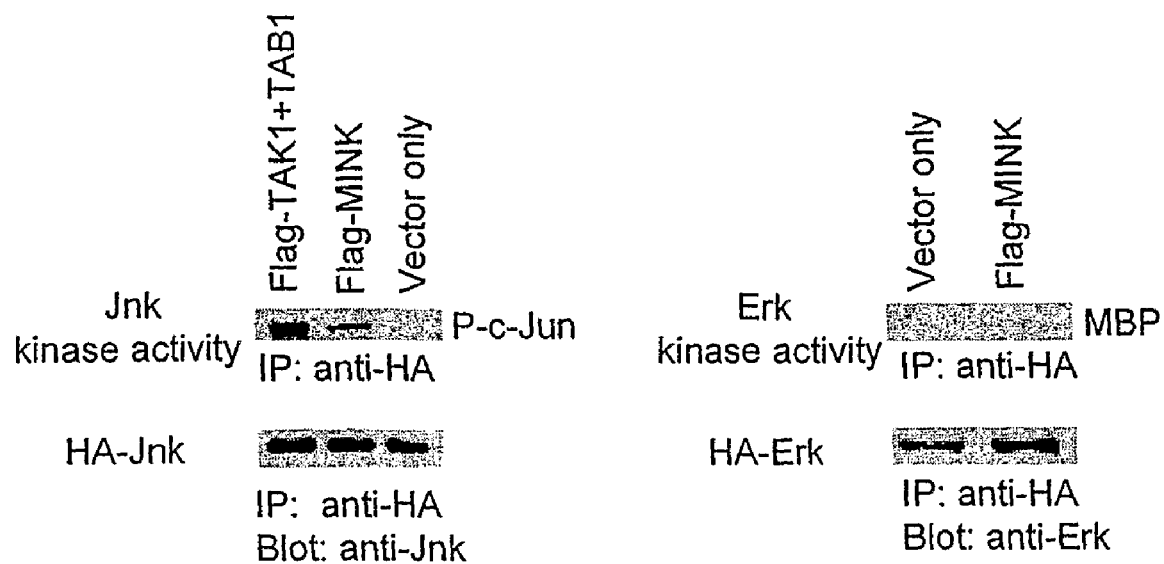
FIG. 8A shows a western blot analysis of lysates from cells co-transfected with HA-JNK and Flag-TAK1+TAB1, Flag-MINK or vector only and immunoprecipitated with anti-HA. The top left panel shows anti-phospho-c-Jun. The bottom left panel shows anti-JNK. The top right panel shows an autoradiograph of phosphorylated MBP. The bottom right panel shows anti-ERK.
Figure 8B:
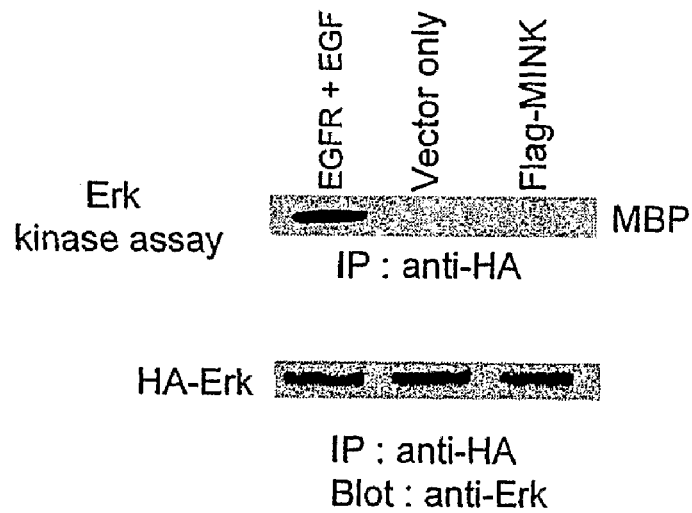
FIG. 8B shows a western blot of immunoprecipitates of anti-HA followed by blotting with anti-ERK (bottom panel) and an autoradiograph of phosphorylated MBP (top panel).
Figure 8C:
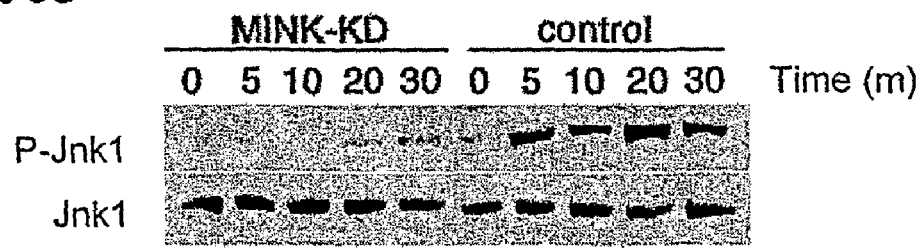
FIG. 8C shows a western blot with antibodies to phospho-JNK1 (top panel) and JNK1 (bottom panel) in fractions of stimulated MINK-KD and control mice.
Figure 8D:
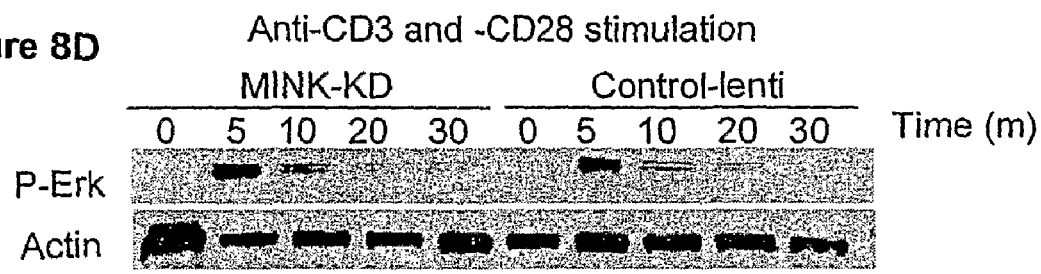
FIG. 8D shows a western blot using antibodies against phospho-ERK (top panel) and actin (bottom panel) in fractions of stimulated MINK-KD and control mice.

Thymocyte apoptosis after TCR ligation has been associated with downstream activation of Jun kinase (Rincon et al., 1998, J. Exp. Med. 188, 1817-1830; Rincon et al., 2000, Free Radic. Biol. Med. 28, 1328-1337). To investigate MINK-associated activation of Jun kinases, flag-tagged MINK was co-transfected into HEK293T cells with HA-tagged JNK before assessment of kinase activity in immunoprecipitated HA-JNK. Transfection with Flag-MINK but not empty vector controls strongly induced JNK activity (FIG. 8A, left panel), but not ERK activity (FIG. 8A, right panel, and FIG. 8B), a kinase that has been associated with positive selection (Sabapathy et al., 1999, Curr. Biol. 9, 116-125; Sabapathy et al., 2001, J. Exp. Med. 193, 317-328). We then examined the interaction of MINK with JNK in DP thymocytes following CD3 ligation. MINK-deficient DP thymocytes express markedly reduced levels of phosphorylated JNK compared with control mice after CD3/CD28 ligation (FIG. 8C), while levels of ERK phosphorylation were indistinguishable in TCR-activated MINK-deficient and wild type thymocytes (FIG. 8D).

Example 9

Analysis of TCR-Linked MINK-Dependent Signaling In Vivo

To investigate the impact of MINK deficiency in activated thymocytes in vivo, intracellular proteins from thymocytes were analyzed shortly after TCR engagement by a negative selection peptide ligand. To this end, thymocytes from OTII TCR tg mice that had been injected with soluble OVA peptide were sorted into $V_\beta 5^+$ and $V_\beta 5^-$ fractions before analysis of thymocyte lysates. As noted above in vitro, administration of a negative-selection ligand in vivo induced association of MINK with Nck and CD3ε in OTII$^+$ ($V_\beta 5^+$) thymocytes, but not in OTII$^-$ ($V_\beta 5^-$) thymocytes (FIG. 7B). Identical immunoprecipitation of these cell lysates with preimmune sera did not reveal MINK protein.

Figure 9A:
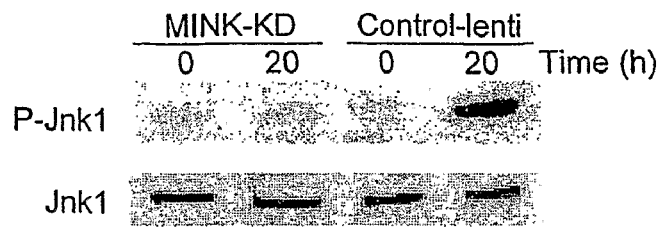
FIG. 9A shows a western blot analysis of DP thymocytes from MINK-KD (left two columns) or control mice (right two columns). Top panel: anti-phospho-JNK1; bottom panel: anti-JNK1.
Figure 9B:
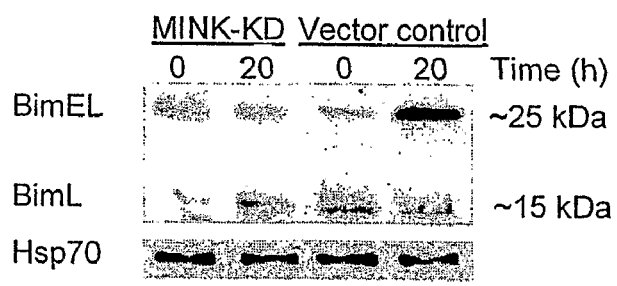
FIG. 9B shows a western blot analysis of DP thymocytes from MINK-KD (left two columns) or control mice (right two columns). Top panel: anti-BimEL; middle panel: anti-BimL; bottom panel: anti-HSP70.
Figure 9C:
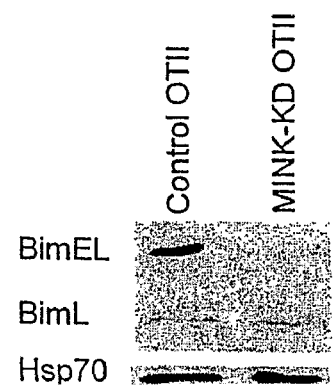
FIG. 9C shows a western blot from MINK-KD OTII (right two columns) and control OTII mice (left two columns). Top panel: anti-BimEL; middle panel: anti-BimL; bottom panel: anti-HSP70.

We next examined the impact of MINK deficiency on JNK phosphorylation in DP thymocytes. MINK-deficient thymocytes contained markedly reduced levels of phosphorylated JNK compared with control mice (FIG. 9A). Analysis of DP thymocytes from MINK-KD and control mice (20-24 h) after injection of either anti-CD3ε antibody or PBS showed that MINK-deficient DP thymocytes failed to display upregulated levels of BimEL protein that were noted in control thymocytes (FIG. 9B). Administration of OVA peptide into MINK-KD and wt OTII mice also showed that MINK-deficient DP thymocytes failed to display upregulated levels of BimEL protein that were noted in control thymocytes (FIG. 9C).

Our analysis indicates that MINK has an essential role in negative selection of thymocytes in vivo, perhaps by coupling the TCR-associated adaptor protein Nck to activation of JNK.

Example 10

Mutational and Yeast Two Hybrid Analysis of MINK/Nck Interactions

While analysis of MINK-deficient thymocytes in vivo and in vitro has suggested that signaling through MINK is necessary for negative selection, the precise role of MINK in this signaling pathway has not been established. In order to dissect the regulatory and catalytic domains of MINK, a variety of MINK mutants are generated.

MINK co-immunoprecipitates with Nck both in activated thymocytes and in OTII TCR+ thymocytes during negative selection following peptide-injection (Example 7). Similar to other GCK-IV family members such as NIK and TNIK, MINK may interact with this adaptor protein through its proline rich motif (Su Y C et al., 1997, *EMBO J.* 16(6):1279-90; Fu C A et al., 1999, *J Biol Chem.* 274(43):30729-37). The Tec kinase, for example, utilizes its PRR (proline rich region) to recruit Src kinases which, in turn, transphosphorylate and activate Tec (Yang W et al., 1995, *J Biol Chem.* 270(35): 20832-40). The protein-protein interaction between Nck and MINK may also constrain MINK into a closed structure that may facilitate catalytic activity. Experiments in this example define the contribution of the MINK PRR region to binding interactions with adaptor proteins such as Nck and determine whether associated conformational changes (e.g., closure of MINK) affect MINK-dependent signaling. Additional binding partners of MINK that interact through the MINK PRR are identified in experiments that combine mutational dissection of MINK with a yeast two hybrid analysis.

In order to analyze MINK/Nck interactions, three mutant MINK PRRs (P551A, P657A, P764A) are independently prepared. After site-directed mutagenesis, constructs tagged with HA or Flag epitopes are co-transfected into 293 T cells or Jurkat T cells with Nck, before immunoprecipitation to identify proline mutations that affect binding to Nck. Alternatively, truncation mutants of the intermediate proline domain of MINK (550-790) cloned by PCR into an expression vector are used to examine PRR-dependent interactions between Nck and MINK in resting and activated T cells or T cell lines; if differences are seen, the relevant PRR deletion mutant(s) are used as controls in a yeast two hybrid system. Findings that MINK does not directly associate with Nck via its PRR suggests the existence of intermediate binding partners between MINK and Nck that may bridge signals from the TCR. Indeed, even if direct MINK:Nck interactions are confirmed, additional adaptor proteins and/or kinases may well be included in this complex. To further define this signaling module, a yeast two hybrid analysis is performed using wild type and mutant PRR of MINK (intermediate region: 550-790) as bait to screen for new binding protein(s). New proteins so identified in this experiment are tested for their functional interaction within the MINK module after activation of T cells with low and high affinity ligands in order to fully delineate the MINK-dependent signaling pathway that is initiated after engagement of the TCR by negative selection ligands.

Example 11

MINK-Dependent Activation of JNK

In this example the effect of mutations on intrinsic MINK kinase activity and downstream activation of JNK are determined. The GCK family of Step 20 kinases, including MINK, activate the JNK pathway in heterologous cells (Yao Z et al., 1999, *J Biol Chem.* 274(4):2118-25; Kiefer F et al., 1996, *EMBO J.* 15(24):7013-25); MINK expression in 293 T cells also activates JNK via a MAP kinase cascade that terminates in the activation of JNK (Dan I et al., 2000, *FEBS Lett* 469: 19-23). Flag tagged MINK and tagged mutant MINK that carry point mutations at discrete kinase sites are expressed in 293 T cells, immunoprecipitated and analyzed for kinase activity using MBP substrate. A mutation of the N-terminal kinase domain of MINK that reduces JNK phosphorylation suggests that phosphorylation by MINK is important for downstream signaling. This observation is incorporated into assays of dominant negative mutant MINK constructs. The possibility that the C-terminal regulatory region of MINK could also be essential for downstream JNK activation is tested by the same mutation/transfection/kinase strategy. The following is intended to serve as an example of the experimental approach used to analyze these catalytic regions.

The K54 residue of MINK, located in the kinase domain, represents the ATP binding residue of MINK. A mutation (K54R) is therefore predicted to block ATP binding of MINK resulting in a kinase-dead mutant (Lim J et al., 2003, *Biochem Biophys Res Commun.* 300(3):694-8). A test of the dominant-negative effect of the K54R MINK kinase mutant entails co-expression of wild type FLAG-tagged MINK kinase with different concentrations of HA-tagged K54R mutant, followed by immunoprecipitation with anti-FLAG antibody and assessment of MINK kinase activity for both autophosphorylation and substrate phosphorylation as described (Lim J et al., 2003, *Biochem Biophys Res Commun.* 300(3):694-8). This region is a target for studies of dominant mutant transgenes.

Example 12

Analysis of Bim Phosphorylation in Negatively or Positively Selected Thymocytes

The proapoptotic Bcl-2 family member Bim (plus Bax and Bak) has been shown to play a key role in apoptosis of autoreactive thymocytes. However, the early molecular events leading to activation of this proapoptotic cascade have not been clear. Example 9 shows that MINK is an important upstream regulator of Bim expression at the transcriptional level. In this example the role of MINK in transcriptional regulation of Bim is further delineated.

Antibodies that specifically recognize JNK phosphorylation sites of Bim (Thr56, Ser44 and Ser58) and ERK phosphorylation sites (Ser55, Ser65, Ser100) (Harada H et al., 2004, *Proc Natl Acad Sci USA.* 101(43):15313-7) were obtained from Stanley Korsmeyer (Dana-Farber Cancer Institute, Boston, Mass.). These antibodies are used to define the phosphorylation status of Bim in negatively and positively selected thymocytes in the presence or absence of MINK.

Negative selection: Thymocytes undergoing negative selection after injecting OVA peptide into OTII mice that lack peripheral CD4 cells (to quench peripheral cytokine release) after treatment of RAG-2/OTII mice with anti-CD4 are generated. Twelve to twenty-four hours later, we determine whether the Bim phosphorylation pattern of negatively-selected DP thymocytes displays the JNK or ERK profile, using phosphorylation site-specific antibodies for Bim, followed by Western blotting. Once the phosphorylation pattern of Bim is determined, the potential role of MINK is established using MINK-deficient thymocytes. Briefly, negatively selecting GFP+ DP thymocytes infected with MINK-RNAi are sorted and western blotted as described in Example 5; negatively selecting thymocytes infected with control vector only or RNAi vector with nonspecific RNAi are used as controls. These studies determine whether a JNK-dependent pattern of Bim phosphorylation is associated with negative selection and if so, whether this phosphorylation pattern is altered in MINK-deficient thymocytes. The latter outcome indicates that MINK directs JNK activity toward a particular pattern of Bim phosphorylation during the process of negative selection. Alternatively, if a JNK-associated phosphorylation pattern of Bim is observed in negatively selecting thymocytes, independent of MINK deficiency, this indicates that MINK does not serve as a direct upstream regulator of Bim phosphorylation and that other upstream kinase(s) may regulate this process.

Positive selection: Positively selected $V_\beta 5^+$ thymocytes from OTII mice are used for these studies. In contrast to JNK-dependent phosphorylation, ERK-dependent phosphorylation of Bim occurs at Ser55, Ser65 and Ser100 (Harada H et al., 2004, Proc Natl Acad Sci USA. 101(43):15313-7). To determine whether MINK-deficiency affects the status or pattern of phosphorylation of Bim protein during positive selection, wild type and MINK-deficient thymocytes are compared for changes in phosphorylation pattern. Since MINK is not upstream of ERK (e.g., knock-down of MINK in thymocytes or T cells does not affect ERK activity after TCR ligation), this system serves as an appropriate control for the above analysis of the role of MINK in Bim phosphorylation during negative selection.

These studies are confirmed and extended in fetal thymic organ culture (FTOC), observing the effects of increasing concentrations of specific peptide on thymocyte deletion (Buch T et al., 2002, Immunity. 16(5):707-18). We are also determining whether the phosphorylation profile of Bim is altered by pharmacological inhibitors of negative and positive selection in FTOC, using HY, OTI and OTII thymocytes. Mice are mated separately, and after 13.5 days thymic lobes are removed and cultured with agonist or antagonist peptide for 9 days on transwells and pharmacological reagents are added to inhibit the ERK pathway (PD98059) or JNK pathway (A20FY09). After 9 days, TCR tg$^+$ thymocytes are sorted for Western blot analysis as described above. If positively selecting cells contain a unique Bim phosphorylation pattern that is associated with ERK (see above), the ERK pharmacological inhibitor should alter Bim phosphorylation, resulting in a different phosphorylation pattern or diminished phosphorylation. Similarly, a role for JNK in Bim phosphorylation of negatively selecting cells is indicated by a change in pattern of phosphorylation or intensity by the JNK inhibitor.

Example 13

Subcellular Localization of MINK Protein in T Cells Engaged with High Affinity Peptide Ligands Engagement of TCR receptor by its ligand results in the down modulation of TCR cell surface expression, which is a central event in TCR signaling and T cell activation (Valitutti S et al., 1995, Nature. 375(6527):148-51). Ligand engagement of T cells prevents TCR recycling back to the cell surface by inducing intracellular retention in the Golgi and their degradation by lysosomes and proteasomes (Carrasco Y R et al., 2003, J Biol. Chem. 278(16):14507-13). The key observation that forms the basis of this approach is the finding that MINK resides in the Golgi apparatus of human and mouse cells (Hu Y et al., 2004, J Biol Chem. 279(52):54387-97). MINK's role in efficient negative selection after high affinity ligand binding may include modulation of surface TCR levels through retention of TCR complex in the Golgi and consequent diminished surface TCR expression in cells undergoing negative selection. Subcellular localization of MINK is examined in thymocytes and in resting and activated T cells from mice using confocal microscopy (Carrasco Y R et al., 2003, J Biol Chem. 278(16):14507-13). Following the observation that mouse MINK localizes in the T cell Golgi, similar to heterologous cells, T cells are activated in vitro using various concentration of anti-CD3ϵ antibody. Surface expression of CD3/TCR complex is examined by FACS using anti-CD3 and anti-TCRβ antibodies. Next, using T cells infected with MINK RNAi that are deficient in MINK activity, levels of surface expression of TCR/CD3 complex are compared to MINK wild type T cells. If MINK deficient T cells express more surface TCR/CD3 complex after robust TCR engagement, MINK may play a role in physical retention and recycling of T cells in the Golgi, e.g., retention may involve structural changes of MINK protein and binding to Nck/TCR complexes through an open vs. closed configuration, rather than phosphorylation by its kinase domain. If confirmed, the use of this surface assay as a monitor for MINK activity, rather than more cumbersome biochemical methods, allows more efficient mutational analysis of the MINK-dependent signaling pathway.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for inhibiting negative selection of thymocytes in a mammal, the method comprising down-regulating MINK in thymocytes in a mammal prior to negative selection of said thymocytes, thereby inhibiting negative selection in thymocytes in a mammal.

2. A method for inhibiting activation-induced cell death of mammalian T cells, the method comprising inhibiting activation-induced cell death of mammalian T cells that are repeatedly stimulated by an antigen by down-regulating MINK in mammalian T cells specific for the antigen.

3. The method of claim 2, wherein the antigen is a microbial antigen.

4. A method for preparing bone marrow cells for use as a bone marrow autograft in a subject in need thereof, the method comprising down-regulating MINK ex vivo in bone marrow cells of the subject, thereby producing a bone marrow autograft for use in said subject in need thereof.

* * * * *

SEQUENCE LISTING

<160> NUMBER OF SEQ ID NOS: 11

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
acacttacgg gcggatca                                                        18

<210> SEQ ID NO 2
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 2
tatggccttc tcacccca                                                       18

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 3
tgtggcctac atctgctcca accag                                               25

<210> SEQ ID NO 4
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 4
tgtactctca ccatcgcaat ttcaagagaa ttgcgatggt gagagtactt ttttc              55

<210> SEQ ID NO 5
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 5
tcgagaaaaa agtactctca ccatcgcaat tctcttgaaa ttgcgatggt gagagtaca          59

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
acacgtacgg aaggatca                                                       18

<210> SEQ ID NO 7
<211> LENGTH: 1300
<212> TYPE: PRT
<213> ORGANISM: Mus musculus

<400> SEQUENCE: 7

Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
```

-continued

```
                85                  90                  95
Asn Asp Asp Gln Leu Trp Leu Val Met Glu Phe Cys Gly Ala Gly Ser
                100                 105                 110

Val Thr Asp Leu Val Lys Asn Thr Lys Gly Asn Ala Leu Lys Glu Asp
                115                 120                 125

Cys Ile Ala Tyr Ile Cys Arg Glu Ile Leu Arg Gly Leu Ala His Leu
                130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
                180                 185                 190

Tyr Trp Met Ala Pro Glu Val Ile Ala Cys Asp Glu Asn Pro Asp Ala
                195                 200                 205

Thr Tyr Asp Tyr Arg Ser Asp Ile Trp Ser Leu Gly Ile Thr Ala Ile
                210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Thr Asp Phe Ile Asp Thr Cys Leu Ile Lys
                260                 265                 270

Thr Tyr Leu Ser Arg Pro Pro Thr Glu Gln Leu Leu Lys Phe Pro Phe
                275                 280                 285

Ile Arg Asp Gln Pro Thr Glu Arg Gln Val Arg Ile Gln Leu Lys Asp
                290                 295                 300

His Ile Asp Arg Ser Arg Lys Lys Arg Gly Glu Lys Glu Thr Glu
305                 310                 315                 320

Tyr Glu Tyr Ser Gly Ser Glu Glu Asp Asp Ser His Gly Glu Glu
                325                 330                 335

Gly Glu Pro Ser Ser Ile Met Asn Val Pro Gly Glu Ser Thr Leu Arg
                340                 345                 350

Arg Glu Phe Leu Arg Leu Gln Gln Glu Asn Lys Ser Asn Ser Glu Ala
                355                 360                 365

Leu Lys Gln Gln Gln Gln Leu Gln Gln Gln Gln Gln Arg Asp Pro Glu
                370                 375                 380

Ala His Ile Lys His Leu Leu His Gln Arg Gln Arg Ile Glu Glu
385                 390                 395                 400

Gln Lys Glu Glu Arg Arg Val Glu Gln Gln Arg Arg Glu Arg
                405                 410                 415

Glu Gln Arg Lys Leu Gln Glu Lys Glu Gln Gln Arg Arg Leu Glu Asp
                420                 425                 430

Met Gln Ala Leu Arg Arg Glu Glu Glu Arg Gln Ala Glu Arg Glu
                435                 440                 445

Gln Glu Tyr Lys Arg Lys Gln Leu Glu Glu Arg Gln Ser Glu Arg
                450                 455                 460

Leu Gln Arg Gln Leu Gln Gln Glu His Ala Tyr Leu Lys Ser Leu Gln
465                 470                 475                 480

Gln Gln Gln Gln Gln Gln Leu Gln Lys Gln Gln Gln Gln Gln
                485                 490                 495

Gln Ile Leu Pro Gly Asp Arg Lys Pro Leu Tyr His Tyr Gly Arg Gly
                500                 505                 510
```

```
Ile Asn Pro Ala Asp Lys Pro Ala Trp Ala Arg Glu Val Glu Arg
    515                 520                 525

Ala Arg Met Asn Lys Gln Gln Asn Ser Pro Leu Ala Lys Arg Ser Gln
    530                 535                 540

Ala Gly Ala Gly Pro Glu Pro Ile Ser Gln Ala Ser Pro Ser Pro
545                 550                 555                 560

Pro Gly Pro Leu Ser Gln Thr Pro Pro Met Gln Arg Pro Val Glu Pro
                565                 570                 575

Gln Glu Gly Pro His Lys Ser Leu Val Ala His Arg Val Pro Leu Lys
                580                 585                 590

Pro Tyr Ala Ala Pro Val Pro Arg Ser Gln Ser Leu Gln Asp Gln Pro
        595                 600                 605

Thr Arg Asn Leu Ala Ala Phe Pro Ala Ser His Asp Pro Asp Pro Ala
    610                 615                 620

Ala Val Pro Thr Pro Thr Ala Thr Pro Ser Ala Arg Gly Ala Val Ile
625                 630                 635                 640

Arg Gln Asn Ser Asp Pro Thr Ser Glu Gly Pro Gly Pro Ser Pro Asn
                645                 650                 655

Pro Pro Ser Trp Val Arg Pro Asp Asn Glu Ala Pro Pro Lys Val Pro
        660                 665                 670

Gln Arg Thr Ser Ser Ile Ala Thr Ala Leu Asn Thr Ser Gly Ala Gly
    675                 680                 685

Gly Ser Arg Pro Ala Gln Ala Val Arg Ala Ser Asn Pro Asp Leu Arg
690                 695                 700

Arg Ser Asp Pro Gly Trp Glu Arg Ser Asp Ser Val Leu Pro Ala Ser
705                 710                 715                 720

His Gly His Leu Pro Gln Ala Gly Ser Leu Glu Arg Asn Arg Asn Arg
                725                 730                 735

Val Gly Ala Ser Thr Lys Leu Asp Ser Ser Pro Val Leu Ser Pro Gly
        740                 745                 750

Asn Lys Ala Lys Pro Glu Asp His Arg Ser Arg Pro Gly Arg Pro Ala
    755                 760                 765

Asp Phe Val Leu Leu Lys Glu Arg Thr Leu Asp Glu Ala Pro Lys Pro
    770                 775                 780

Pro Lys Lys Ala Met Asp Tyr Ser Ser Ser Ser Glu Glu Val Glu Ser
785                 790                 795                 800

Ser Glu Glu Glu Glu Glu Gly Asp Gly Glu Pro Ser Glu Gly Ser
                805                 810                 815

Arg Asp Thr Pro Gly Gly Arg Ser Asp Gly Asp Thr Ser Val Thr
                820                 825                 830

Thr Met Val Val His Asp Val Glu Glu Ile Ser Gly Thr Gln Pro Ser
        835                 840                 845

Tyr Gly Gly Gly Thr Met Val Val Gln Arg Thr Pro Glu Glu Glu Arg
    850                 855                 860

Ser Leu Leu Leu Ala Asp Ser Asn Gly Tyr Thr Asn Leu Pro Asp Val
865                 870                 875                 880

Val Gln Pro Ser His Ser Pro Thr Glu Asn Ser Lys Gly Gln Ser Pro
                885                 890                 895

Pro Thr Lys Asp Gly Gly Ser Asp Tyr Gln Ser Arg Gly Leu Val Lys
        900                 905                 910

Ala Pro Gly Lys Ser Ser Phe Thr Met Phe Val Asp Leu Gly Ile Tyr
    915                 920                 925

Gln Pro Gly Gly Ser Gly Asp Thr Ile Pro Ile Thr Ala Leu Val Gly
    930                 935                 940
```

```
Gly Glu Gly Gly Arg Leu Asp Gln Leu Gln Phe Asp Val Arg Lys Gly
945                 950                 955                 960

Ser Val Val Asn Val Asn Pro Thr Asn Thr Arg Ala His Ser Glu Thr
            965                 970                 975

Pro Glu Ile Arg Lys Tyr Lys Arg Phe Asn Ser Glu Ile Leu Cys
        980                 985                 990

Ala Ala Leu Trp Gly Val Asn Leu Leu Val Gly Thr Glu Asn Gly Leu
        995                 1000                1005

Met Leu Leu Asp Arg Ser Gly Gln Gly Lys Val Tyr Gly Leu Ile
    1010                1015                1020

Gly Arg Arg Arg Phe Gln Gln Met Asp Val Leu Glu Gly Leu Asn
    1025                1030                1035

Leu Leu Ile Thr Ile Ser Gly Lys Arg Asn Lys Leu Arg Val Tyr
    1040                1045                1050

Tyr Leu Ser Trp Leu Arg Asn Lys Ile Leu His Asn Asp Pro Glu
    1055                1060                1065

Val Glu Lys Lys Gln Gly Trp Thr Thr Val Gly Asp Met Glu Gly
    1070                1075                1080

Cys Gly His Tyr Arg Val Val Lys Tyr Glu Arg Ile Lys Phe Leu
    1085                1090                1095

Val Ile Ala Leu Lys Asn Ser Val Glu Val Tyr Ala Trp Ala Pro
    1100                1105                1110

Lys Pro Tyr His Lys Phe Met Ala Phe Lys Ser Phe Ala Asp Leu
    1115                1120                1125

Pro His Arg Pro Leu Leu Val Asp Leu Thr Val Glu Glu Gly Gln
    1130                1135                1140

Arg Leu Lys Val Ile Tyr Gly Ser Ser Ala Gly Phe His Ala Val
    1145                1150                1155

Asp Val Asp Ser Gly Asn Ser Tyr Asp Ile Tyr Ile Pro Val His
    1160                1165                1170

Ile Gln Ser Gln Ile Thr Pro His Ala Ile Ile Phe Leu Pro Asn
    1175                1180                1185

Thr Asp Gly Met Glu Met Leu Leu Cys Tyr Glu Asp Glu Gly Val
    1190                1195                1200

Tyr Val Asn Thr Tyr Gly Arg Ile Ile Lys Asp Val Val Leu Gln
    1205                1210                1215

Trp Gly Glu Met Pro Thr Ser Val Ala Tyr Ile Cys Ser Asn Gln
    1220                1225                1230

Ile Met Gly Trp Gly Glu Lys Ala Ile Glu Ile Arg Ser Val Glu
    1235                1240                1245

Thr Gly His Leu Asp Gly Val Phe Met His Lys Arg Ala Gln Arg
    1250                1255                1260

Leu Lys Phe Leu Cys Glu Arg Asn Asp Lys Val Phe Phe Ala Ser
    1265                1270                1275

Val Arg Ser Gly Gly Ser Ser Gln Val Tyr Phe Met Thr Leu Asn
    1280                1285                1290

Arg Asn Cys Ile Met Asn Trp
    1295                1300

<210> SEQ ID NO 8
<211> LENGTH: 1332
<212> TYPE: PRT
<213> ORGANISM: Homo sapiens

<400> SEQUENCE: 8
```

```
Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
            100                 105                 110

Val Thr Asp Leu Val Lys Asn Thr Lys Gly Asn Ala Leu Lys Glu Asp
            115                 120                 125

Cys Ile Ala Tyr Ile Cys Arg Glu Ile Leu Arg Gly Leu Ala His Leu
130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Ile Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Ile Asp Phe Ile Asp Thr Cys Leu Ile Lys
                260                 265                 270

Thr Tyr Leu Ser Arg Pro Pro Thr Glu Gln Leu Leu Lys Phe Pro Phe
    275                 280                 285

Ile Arg Asp Gln Pro Thr Glu Arg Gln Val Arg Ile Gln Leu Lys Asp
290                 295                 300

His Ile Asp Arg Ser Arg Lys Lys Arg Gly Glu Lys Glu Thr Glu
305                 310                 315                 320

Tyr Glu Tyr Ser Gly Ser Glu Glu Asp Asp Ser His Gly Glu Glu
                325                 330                 335

Gly Glu Pro Ser Ser Ile Met Asn Val Pro Gly Glu Ser Thr Leu Arg
            340                 345                 350

Arg Glu Phe Leu Arg Leu Gln Gln Glu Asn Lys Ser Asn Ser Glu Ala
            355                 360                 365

Leu Lys Gln Gln Gln Gln Leu Gln Gln Gln Gln Arg Asp Pro Glu
370                 375                 380

Ala His Ile Lys His Leu Leu His Gln Gln Arg Arg Ile Glu Glu
385                 390                 395                 400

Gln Lys Glu Glu Arg Arg Val Glu Gln Gln Arg Arg Glu Arg
                405                 410                 415

Glu Gln Arg Lys Leu Gln Glu Lys Glu Gln Gln Arg Arg Leu Glu Asp
```

```
                420             425             430
Met Gln Ala Leu Arg Arg Glu Glu Arg Gln Ala Glu Arg Glu
        435             440             445
Gln Glu Tyr Lys Arg Lys Gln Leu Glu Glu Arg Gln Ser Glu Arg
    450             455             460
Leu Gln Arg Gln Leu Gln Gln Glu His Ala Tyr Leu Lys Ser Leu Gln
465             470             475             480
Gln Gln Gln Gln Gln Gln Leu Gln Lys Gln Gln Gln Gln Leu
            485             490             495
Leu Pro Gly Asp Arg Lys Pro Leu Tyr His Tyr Gly Arg Gly Met Asn
            500             505             510
Pro Ala Asp Lys Pro Ala Trp Ala Arg Glu Val Glu Arg Thr Arg
        515             520             525
Met Asn Lys Gln Gln Asn Ser Pro Leu Ala Lys Ser Lys Pro Gly Ser
        530             535             540
Thr Gly Pro Glu Pro Pro Ile Pro Gln Ala Ser Pro Gly Pro Gly
545             550             555             560
Pro Leu Ser Gln Thr Pro Pro Met Gln Arg Pro Val Glu Pro Gln Glu
                565             570             575
Gly Pro His Lys Ser Leu Val Ala His Arg Val Pro Leu Lys Pro Tyr
            580             585             590
Ala Ala Pro Val Pro Arg Ser Gln Ser Leu Gln Asp Gln Pro Thr Arg
            595             600             605
Asn Leu Ala Ala Phe Pro Ala Ser His Asp Pro Asp Pro Ala Ile Pro
    610             615             620
Ala Pro Thr Ala Thr Pro Ser Ala Arg Gly Ala Val Ile Arg Gln Asn
625             630             635             640
Ser Asp Pro Thr Ser Glu Gly Pro Gly Pro Ser Asn Pro Pro Ala
                645             650             655
Trp Val Arg Pro Asp Asn Glu Ala Pro Pro Lys Val Pro Gln Arg Thr
                660             665             670
Ser Ser Ile Ala Thr Ala Leu Asn Thr Ser Gly Ala Gly Gly Ser Arg
        675             680             685
Pro Ala Gln Ala Val Arg Ala Arg Pro Arg Ser Asn Ser Ala Trp Gln
    690             695             700
Ile Tyr Leu Gln Arg Arg Ala Glu Arg Gly Thr Pro Lys Pro Pro Gly
705             710             715             720
Pro Pro Ala Gln Pro Pro Gly Pro Pro Asn Ala Ser Ser Asn Pro Asp
            725             730             735
Leu Arg Arg Ser Asp Pro Gly Trp Glu Arg Ser Asp Ser Val Leu Pro
            740             745             750
Ala Ser His Gly His Leu Pro Gln Ala Gly Ser Leu Glu Arg Asn Arg
        755             760             765
Val Gly Val Ser Ser Lys Pro Asp Ser Ser Pro Val Leu Ser Pro Gly
        770             775             780
Asn Lys Ala Lys Pro Asp Asp His Arg Ser Arg Pro Gly Arg Pro Ala
785             790             795             800
Asp Phe Val Leu Leu Lys Glu Arg Thr Leu Asp Glu Ala Pro Arg Pro
                805             810             815
Pro Lys Lys Ala Met Asp Tyr Ser Ser Ser Ser Glu Val Glu Ser
            820             825             830
Ser Glu Asp Asp Glu Glu Glu Gly Glu Gly Gly Pro Ala Glu Gly Ser
            835             840             845
```

-continued

Arg Asp Thr Pro Gly Gly Arg Ser Asp Gly Asp Thr Asp Ser Val Ser
850                 855                 860

Thr Met Val Val His Asp Val Glu Glu Ile Thr Gly Thr Gln Pro Pro
865                 870                 875                 880

Tyr Gly Gly Gly Thr Met Val Val Gln Arg Thr Pro Glu Glu Arg
        885                 890                 895

Asn Leu Leu His Ala Asp Ser Asn Gly Tyr Thr Asn Leu Pro Asp Val
            900                 905                 910

Val Gln Pro Ser His Ser Pro Thr Glu Asn Ser Lys Gly Gln Ser Pro
        915                 920                 925

Pro Ser Lys Asp Gly Ser Gly Asp Tyr Gln Ser Arg Gly Leu Val Lys
    930                 935                 940

Ala Pro Gly Lys Ser Ser Phe Thr Met Phe Val Asp Leu Gly Ile Tyr
945                 950                 955                 960

Gln Pro Gly Gly Ser Gly Asp Ser Ile Pro Ile Thr Ala Leu Val Gly
            965                 970                 975

Gly Glu Gly Thr Arg Leu Asp Gln Leu Gln Tyr Asp Val Arg Lys Gly
                980                 985                 990

Ser Val Val Asn Val Asn Pro Thr Asn Thr Arg Ala His Ser Glu Thr
        995                 1000                1005

Pro Glu Ile Arg Lys Tyr Lys Lys Arg Phe Asn Ser Glu Ile Leu
    1010                1015                1020

Cys Ala Ala Leu Trp Gly Val Asn Leu Leu Val Gly Thr Glu Asn
    1025                1030                1035

Gly Leu Met Leu Leu Asp Arg Ser Gly Gln Gly Lys Val Tyr Gly
    1040                1045                1050

Leu Ile Gly Arg Arg Arg Phe Gln Gln Met Asp Val Leu Glu Gly
    1055                1060                1065

Leu Asn Leu Leu Ile Thr Ile Ser Gly Lys Arg Asn Lys Leu Arg
    1070                1075                1080

Val Tyr Tyr Leu Ser Trp Leu Arg Asn Lys Ile Leu His Asn Asp
    1085                1090                1095

Pro Glu Val Glu Lys Lys Gln Gly Trp Thr Thr Val Gly Asp Met
    1100                1105                1110

Glu Gly Cys Gly His Tyr Arg Val Val Lys Tyr Glu Arg Ile Lys
    1115                1120                1125

Phe Leu Val Ile Ala Leu Lys Ser Ser Val Glu Val Tyr Ala Trp
    1130                1135                1140

Ala Pro Lys Pro Tyr His Lys Phe Met Ala Phe Lys Ser Phe Ala
    1145                1150                1155

Asp Leu Pro His Arg Pro Leu Leu Val Asp Leu Thr Val Glu Glu
    1160                1165                1170

Gly Gln Arg Leu Lys Val Ile Tyr Gly Ser Ser Ala Gly Phe His
    1175                1180                1185

Ala Val Asp Val Asp Ser Gly Asn Ser Tyr Asp Ile Tyr Ile Pro
    1190                1195                1200

Val His Ile Gln Ser Gln Ile Thr Pro His Ala Ile Ile Phe Leu
    1205                1210                1215

Pro Asn Thr Asp Gly Met Glu Met Leu Leu Cys Tyr Glu Asp Glu
    1220                1225                1230

Gly Val Tyr Val Asn Thr Tyr Gly Arg Ile Ile Lys Asp Val Val
    1235                1240                1245

Leu Gln Trp Gly Glu Met Pro Thr Ser Val Ala Tyr Ile Cys Ser
    1250                1255                1260

```
Asn Gln Ile Met Gly Trp Gly Glu Lys Ala Ile Glu Ile Arg Ser
    1265                1270                1275

Val Glu Thr Gly His Leu Asp Gly Val Phe Met His Lys Arg Ala
    1280                1285                1290

Gln Arg Leu Lys Phe Leu Cys Glu Arg Asn Asp Lys Val Phe Phe
    1295                1300                1305

Ala Ser Val Arg Ser Gly Gly Ser Ser Gln Val Tyr Phe Met Thr
    1310                1315                1320

Leu Asn Arg Asn Cys Ile Met Asn Trp
    1325                1330

<210> SEQ ID NO 9
<211> LENGTH: 1312
<212> TYPE: PRT
<213> ORGANISM: Homo sapiens

<400> SEQUENCE: 9

Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
            100                 105                 110

Val Thr Asp Leu Val Lys Asn Thr Lys Gly Asn Ala Leu Lys Glu Asp
        115                 120                 125

Cys Ile Ala Tyr Ile Cys Arg Glu Ile Leu Arg Gly Leu Ala His Leu
    130                 135                 140

His Ala His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Ile Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Pro Arg Leu Lys Ser Lys
                245                 250                 255

Lys Trp Ser Lys Lys Phe Ile Asp Phe Ile Asp Thr Cys Leu Ile Lys
            260                 265                 270

Thr Tyr Leu Ser Arg Pro Pro Thr Glu Gln Leu Leu Lys Phe Pro Phe
        275                 280                 285

Ile Arg Asp Gln Pro Thr Glu Arg Gln Val Arg Ile Gln Leu Lys Asp
    290                 295                 300
```

-continued

```
His Ile Asp Arg Ser Arg Lys Lys Arg Gly Lys Glu Thr Glu
305                 310                 315                 320

Tyr Glu Tyr Ser Gly Ser Glu Glu Asp Asp Ser His Gly Glu Glu
                325                 330                 335

Gly Glu Pro Ser Ser Ile Met Asn Val Pro Gly Glu Ser Thr Leu Arg
            340                 345                 350

Arg Glu Phe Leu Arg Leu Gln Gln Glu Asn Lys Ser Asn Ser Glu Ala
        355                 360                 365

Leu Lys Gln Gln Gln Gln Leu Gln Gln Gln Gln Arg Asp Pro Glu
    370                 375                 380

Ala His Ile Lys His Leu Leu His Gln Arg Gln Arg Ile Glu Glu
385                 390                 395                 400

Gln Lys Glu Glu Arg Arg Val Glu Glu Gln Arg Gln Arg Glu Arg
                405                 410                 415

Glu Gln Arg Lys Leu Gln Glu Lys Glu Gln Arg Arg Leu Glu Asp
            420                 425                 430

Met Gln Ala Leu Arg Arg Glu Glu Arg Arg Gln Ala Glu Arg Glu
        435                 440                 445

Gln Glu Tyr Lys Arg Lys Gln Leu Glu Glu Gln Arg Gln Ser Glu Arg
    450                 455                 460

Leu Gln Arg Gln Leu Gln Gln Glu His Ala Tyr Leu Lys Ser Leu Gln
465                 470                 475                 480

Gln Gln Gln Gln Gln Gln Leu Gln Lys Gln Gln Gln Gln Leu
                485                 490                 495

Leu Pro Gly Asp Arg Lys Pro Leu Tyr His Tyr Gly Arg Gly Met Asn
            500                 505                 510

Pro Ala Asp Lys Pro Ala Trp Ala Arg Glu Val Glu Glu Arg Thr Arg
        515                 520                 525

Met Asn Lys Gln Gln Asn Ser Pro Leu Ala Lys Ser Lys Pro Gly Ser
    530                 535                 540

Thr Gly Pro Glu Pro Ile Pro Gln Ala Ser Pro Gly Pro Gly
545                 550                 555                 560

Pro Leu Ser Gln Thr Pro Met Gln Arg Pro Val Glu Pro Gln Glu
                565                 570                 575

Gly Pro His Lys Ser Leu Gln Asp Gln Pro Thr Arg Asn Leu Ala Ala
            580                 585                 590

Phe Pro Ala Ser His Asp Pro Asp Ala Ile Pro Ala Pro Thr Ala
        595                 600                 605

Thr Pro Ser Ala Arg Gly Ala Val Ile Arg Gln Asn Ser Asp Pro Thr
    610                 615                 620

Ser Glu Gly Pro Gly Pro Ser Pro Asn Pro Pro Ala Trp Val Arg Pro
625                 630                 635                 640

Asp Asn Glu Ala Pro Pro Lys Val Pro Gln Arg Thr Ser Ser Ile Ala
                645                 650                 655

Thr Ala Leu Asn Thr Ser Gly Ala Gly Gly Ser Arg Pro Ala Gln Ala
            660                 665                 670

Val Arg Ala Arg Pro Arg Ser Asn Ser Ala Trp Gln Ile Tyr Leu Gln
        675                 680                 685

Arg Arg Ala Glu Arg Gly Thr Pro Lys Pro Gly Pro Pro Ala Gln
    690                 695                 700

Pro Pro Gly Pro Pro Asn Ala Ser Ser Asn Pro Asp Leu Arg Arg Ser
705                 710                 715                 720

Asp Pro Gly Trp Glu Arg Ser Asp Ser Val Leu Pro Ala Ser His Gly
```

-continued

```
                725                 730                 735
His Leu Pro Gln Ala Gly Ser Leu Glu Arg Asn Arg Val Gly Ala Ser
            740                 745                 750

Ser Lys Leu Asp Ser Ser Pro Val Leu Ser Pro Gly Asn Lys Ala Lys
        755                 760                 765

Pro Asp Asp His Arg Ser Arg Pro Gly Arg Pro Ala Asp Phe Val Leu
    770                 775                 780

Leu Lys Glu Arg Thr Leu Asp Glu Ala Pro Arg Pro Lys Lys Ala
785                 790                 795                 800

Met Asp Tyr Ser Ser Ser Glu Glu Val Glu Ser Ser Glu Asp Asp
                805                 810                 815

Glu Glu Glu Gly Glu Gly Gly Pro Ala Glu Gly Ser Arg Asp Thr Pro
            820                 825                 830

Gly Gly Arg Ser Asp Gly Asp Thr Asp Ser Val Ser Thr Met Val Val
        835                 840                 845

His Asp Val Glu Glu Ile Thr Gly Thr Gln Pro Pro Tyr Gly Gly Gly
    850                 855                 860

Thr Met Val Val Gln Arg Thr Pro Glu Glu Arg Asn Leu Leu His
865                 870                 875                 880

Ala Asp Ser Asn Gly Tyr Thr Asn Leu Pro Asp Val Val Gln Pro Ser
                885                 890                 895

His Ser Pro Thr Glu Asn Ser Lys Gly Gln Ser Pro Ser Lys Asp
            900                 905                 910

Gly Ser Gly Asp Tyr Gln Ser Arg Gly Leu Val Lys Ala Pro Gly Lys
        915                 920                 925

Ser Ser Phe Thr Met Phe Val Asp Leu Gly Ile Tyr Gln Pro Gly Gly
    930                 935                 940

Ser Gly Asp Ser Ile Pro Ile Thr Ala Leu Val Gly Gly Glu Gly Thr
945                 950                 955                 960

Arg Leu Asp Gln Leu Gln Tyr Asp Val Arg Lys Gly Ser Val Val Asn
                965                 970                 975

Val Asn Pro Thr Asn Thr Arg Ala His Ser Glu Thr Pro Glu Ile Arg
            980                 985                 990

Lys Tyr Lys Lys Arg Phe Asn Ser  Glu Ile Leu Cys Ala  Ala Leu Trp
        995                 1000                 1005

Gly Val  Asn Leu Leu Val Gly  Thr Glu Asn Gly Leu  Met Leu Leu
    1010                 1015                 1020

Asp Arg  Ser Gly Gln Gly Lys  Val Tyr Gly Leu Ile  Gly Arg Arg
    1025                 1030                 1035

Arg Phe  Gln Gln Met Asp Val  Leu Glu Gly Leu Asn  Leu Leu Ile
    1040                 1045                 1050

Thr Ile  Ser Gly Lys Arg Asn  Lys Leu Arg Val Tyr  Tyr Leu Ser
    1055                 1060                 1065

Trp Leu  Arg Asn Lys Ile Leu  His Asn Asp Pro Glu  Val Glu Lys
    1070                 1075                 1080

Lys Gln  Gly Trp Thr Thr Val  Gly Asp Met Glu Gly  Cys Gly His
    1085                 1090                 1095

Tyr Arg  Val Val Lys Tyr Glu  Arg Ile Lys Phe Leu  Val Ile Ala
    1100                 1105                 1110

Leu Lys  Ser Ser Val Glu Val  Tyr Ala Trp Ala Pro  Lys Pro Tyr
    1115                 1120                 1125

His Lys  Phe Met Ala Phe Lys  Ser Phe Ala Asp Leu  Pro His Arg
    1130                 1135                 1140
```

```
Pro  Leu  Leu  Val  Asp  Leu  Thr  Val  Glu  Glu  Gly  Gln  Arg  Leu  Lys
     1145                1150                1155

Val  Ile  Tyr  Gly  Ser  Ser  Ala  Gly  Phe  His  Ala  Val  Asp  Val  Asp
     1160                1165                1170

Ser  Gly  Asn  Ser  Tyr  Asp  Ile  Tyr  Ile  Pro  Val  His  Ile  Gln  Ser
     1175                1180                1185

Gln  Ile  Thr  Pro  His  Ala  Ile  Ile  Phe  Leu  Pro  Asn  Thr  Asp  Gly
     1190                1195                1200

Met  Glu  Met  Leu  Leu  Cys  Tyr  Glu  Asp  Glu  Gly  Val  Tyr  Val  Asn
     1205                1210                1215

Thr  Tyr  Gly  Arg  Ile  Ile  Lys  Asp  Val  Val  Leu  Gln  Trp  Gly  Glu
     1220                1225                1230

Met  Pro  Thr  Ser  Val  Ala  Tyr  Ile  Cys  Ser  Asn  Gln  Ile  Met  Gly
     1235                1240                1245

Trp  Gly  Glu  Lys  Ala  Ile  Glu  Ile  Arg  Ser  Val  Glu  Thr  Gly  His
     1250                1255                1260

Leu  Asp  Gly  Val  Phe  Met  His  Lys  Arg  Ala  Gln  Arg  Leu  Lys  Phe
     1265                1270                1275

Leu  Cys  Glu  Arg  Asn  Asp  Lys  Val  Phe  Phe  Ala  Ser  Val  Arg  Ser
     1280                1285                1290

Gly  Gly  Ser  Ser  Gln  Val  Tyr  Phe  Met  Thr  Leu  Asn  Arg  Asn  Cys
     1295                1300                1305

Ile  Met  Asn  Trp
     1310

<210> SEQ ID NO 10
<211> LENGTH: 1303
<212> TYPE: PRT
<213> ORGANISM: Homo sapiens

<400> SEQUENCE: 10

Met  Gly  Asp  Pro  Ala  Pro  Ala  Arg  Ser  Leu  Asp  Ile  Asp  Leu  Ser
1                   5                   10                  15

Ala  Leu  Arg  Asp  Pro  Ala  Gly  Ile  Phe  Glu  Leu  Val  Glu  Val  Gly
                    20                  25                  30

Asn  Gly  Thr  Tyr  Gly  Gln  Val  Tyr  Lys  Gly  Arg  His  Val  Lys  Thr  Gly
            35                  40                  45

Gln  Leu  Ala  Ala  Ile  Lys  Val  Met  Asp  Val  Thr  Glu  Asp  Glu  Glu  Glu
        50                  55                  60

Glu  Ile  Lys  Gln  Glu  Ile  Asn  Met  Leu  Lys  Lys  Tyr  Ser  His  His  Arg
65                  70                  75                  80

Asn  Ile  Ala  Thr  Tyr  Tyr  Gly  Ala  Phe  Ile  Lys  Lys  Ser  Pro  Pro  Gly
                85                  90                  95

Asn  Asp  Asp  Gln  Leu  Trp  Leu  Val  Met  Glu  Phe  Cys  Gly  Ala  Gly  Ser
            100                 105                 110

Val  Thr  Asp  Leu  Val  Lys  Asn  Thr  Lys  Gly  Asn  Ala  Leu  Lys  Glu  Asp
        115                 120                 125

Cys  Ile  Ala  Tyr  Ile  Cys  Arg  Glu  Ile  Leu  Arg  Gly  Leu  Ala  His  Leu
    130                 135                 140

His  Ala  His  Lys  Val  Ile  His  Arg  Asp  Ile  Lys  Gly  Gln  Asn  Val  Leu
145                 150                 155                 160

Leu  Thr  Glu  Asn  Ala  Glu  Val  Lys  Leu  Val  Asp  Phe  Gly  Val  Ser  Ala
                165                 170                 175

Gln  Leu  Asp  Arg  Thr  Val  Gly  Arg  Arg  Asn  Thr  Phe  Ile  Gly  Thr  Pro
            180                 185                 190
```

-continued

```
Tyr Trp Met Ala Pro Glu Val Ile Ala Cys Asp Glu Asn Pro Asp Ala
            195                 200                 205

Thr Tyr Asp Tyr Arg Ser Asp Ile Trp Ser Leu Gly Ile Thr Ala Ile
            210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Ile Asp Phe Ile Asp Thr Cys Leu Ile Lys
                260                 265                 270

Thr Tyr Leu Ser Arg Pro Thr Glu Gln Leu Leu Lys Phe Pro Phe
            275                 280                 285

Ile Arg Asp Gln Pro Thr Glu Arg Gln Val Arg Ile Gln Leu Lys Asp
            290                 295                 300

His Ile Asp Arg Ser Arg Lys Lys Arg Gly Glu Lys Glu Thr Glu
305                 310                 315                 320

Tyr Glu Tyr Ser Gly Ser Glu Glu Glu Asp Ser His Gly Glu Glu
                325                 330                 335

Gly Glu Pro Ser Ser Ile Met Asn Val Pro Gly Glu Ser Thr Leu Arg
                340                 345                 350

Arg Glu Phe Leu Arg Leu Gln Gln Glu Asn Lys Ser Asn Ser Glu Ala
            355                 360                 365

Leu Lys Gln Gln Gln Gln Leu Gln Gln Gln Gln Arg Asp Pro Glu
370                 375                 380

Ala His Ile Lys His Leu Leu His Gln Arg Gln Arg Ile Glu Glu
385                 390                 395                 400

Gln Lys Glu Glu Arg Arg Arg Val Glu Glu Gln Arg Glu Arg Glu Arg
                405                 410                 415

Glu Gln Arg Lys Leu Gln Glu Lys Glu Gln Gln Arg Arg Leu Glu Asp
            420                 425                 430

Met Gln Ala Leu Arg Arg Glu Glu Glu Arg Arg Gln Ala Glu Arg Glu
            435                 440                 445

Gln Glu Tyr Lys Arg Lys Gln Leu Glu Glu Gln Arg Gln Ser Glu Arg
            450                 455                 460

Leu Gln Arg Gln Leu Gln Gln Glu His Ala Tyr Leu Lys Ser Leu Gln
465                 470                 475                 480

Gln Gln Gln Gln Gln Gln Leu Gln Lys Gln Gln Gln Gln Gln Leu
                485                 490                 495

Leu Pro Gly Asp Arg Lys Pro Leu Tyr His Tyr Gly Arg Gly Met Asn
            500                 505                 510

Pro Ala Asp Lys Pro Ala Trp Ala Arg Glu Val Glu Glu Arg Thr Arg
            515                 520                 525

Met Asn Lys Gln Gln Asn Ser Pro Leu Ala Lys Ser Lys Pro Gly Ser
530                 535                 540

Thr Gly Pro Glu Pro Ile Pro Gln Ala Ser Pro Gly Pro Pro Gly
545                 550                 555                 560

Pro Leu Ser Gln Thr Pro Met Gln Arg Pro Val Glu Pro Gln Glu
                565                 570                 575

Gly Pro His Lys Ser Leu Val Ala His Arg Val Pro Leu Lys Pro Tyr
            580                 585                 590

Ala Ala Pro Val Pro Arg Ser Gln Ser Leu Gln Asp Gln Pro Thr Arg
            595                 600                 605

Asn Leu Ala Ala Phe Pro Ala Ser His Asp Pro Asp Pro Ala Ile Pro
610                 615                 620
```

```
Ala Pro Thr Ala Thr Pro Ser Ala Arg Gly Ala Val Ile Arg Gln Asn
625                 630                 635                 640

Ser Asp Pro Thr Ser Glu Gly Pro Gly Pro Ser Asn Pro Pro Ala
            645                 650                 655

Trp Val Arg Pro Asp Asn Glu Ala Pro Pro Lys Val Pro Gln Arg Thr
        660                 665                 670

Ser Ser Ile Ala Thr Ala Leu Asn Thr Ser Gly Ala Gly Gly Ser Arg
            675                 680                 685

Pro Ala Gln Ala Val Arg Ala Ser Asn Pro Asp Leu Arg Arg Ser Asp
        690                 695                 700

Pro Gly Trp Glu Arg Ser Asp Ser Val Leu Pro Ala Ser His Gly His
705                 710                 715                 720

Leu Pro Gln Ala Gly Ser Leu Glu Arg Asn Arg Val Gly Val Ser Ser
                725                 730                 735

Lys Pro Asp Ser Ser Pro Val Leu Ser Pro Gly Asn Lys Ala Lys Pro
            740                 745                 750

Asp Asp His Arg Ser Arg Pro Gly Arg Pro Ala Ser Tyr Lys Arg Ala
            755                 760                 765

Ile Gly Glu Asp Phe Val Leu Leu Lys Glu Arg Thr Leu Asp Glu Ala
        770                 775                 780

Pro Arg Pro Pro Lys Lys Ala Met Asp Tyr Ser Ser Ser Ser Glu Glu
785                 790                 795                 800

Val Glu Ser Ser Glu Asp Asp Glu Glu Glu Gly Gly Gly Pro Ala
            805                 810                 815

Glu Gly Ser Arg Asp Thr Pro Gly Gly Arg Ser Asp Gly Asp Thr Asp
            820                 825                 830

Ser Val Ser Thr Met Val Val His Asp Val Glu Ile Thr Gly Thr
            835                 840                 845

Gln Pro Pro Tyr Gly Gly Gly Thr Met Val Val Gln Arg Thr Pro Glu
        850                 855                 860

Glu Glu Arg Asn Leu Leu His Ala Asp Ser Asn Gly Tyr Thr Asn Leu
865                 870                 875                 880

Pro Asp Val Val Gln Pro Ser His Ser Pro Thr Glu Asn Ser Lys Gly
                885                 890                 895

Gln Ser Pro Pro Ser Lys Asp Gly Ser Gly Asp Tyr Gln Ser Arg Gly
            900                 905                 910

Leu Val Lys Ala Pro Gly Lys Ser Ser Phe Thr Met Phe Val Asp Leu
        915                 920                 925

Gly Ile Tyr Gln Pro Gly Gly Ser Gly Asp Ser Ile Pro Ile Thr Ala
        930                 935                 940

Leu Val Gly Gly Glu Gly Thr Arg Leu Asp Gln Leu Gln Tyr Asp Val
945                 950                 955                 960

Arg Lys Gly Ser Val Val Asn Val Asn Pro Thr Asn Thr Arg Ala His
            965                 970                 975

Ser Glu Thr Pro Glu Ile Arg Lys Tyr Lys Lys Arg Phe Asn Ser Glu
            980                 985                 990

Ile Leu Cys Ala Ala Leu Trp Gly Val Asn Leu Leu Val Gly Thr Glu
        995                 1000                1005

Asn Gly Leu Met Leu Leu Asp Arg Ser Gly Gln Gly Lys Val Tyr
    1010                1015                1020

Gly Leu Ile Gly Arg Arg Arg Phe Gln Gln Met Asp Val Leu Glu
    1025                1030                1035

Gly Leu Asn Leu Leu Ile Thr Ile Ser Gly Lys Arg Asn Lys Leu
```

```
                    1040              1045              1050

Arg Val Tyr Tyr Leu Ser Trp Leu Arg Asn Lys Ile Leu His Asn
        1055              1060              1065

Asp Pro Glu Val Glu Lys Lys Gln Gly Trp Thr Thr Val Gly Asp
1070              1075              1080

Met Glu Gly Cys Gly His Tyr Arg Val Val Lys Tyr Glu Arg Ile
    1085              1090              1095

Lys Phe Leu Val Ile Ala Leu Lys Ser Ser Val Glu Val Tyr Ala
1100              1105              1110

Trp Ala Pro Lys Pro Tyr His Lys Phe Met Ala Phe Lys Ser Phe
    1115              1120              1125

Ala Asp Leu Pro His Arg Pro Leu Leu Val Asp Leu Thr Val Glu
1130              1135              1140

Glu Gly Gln Arg Leu Lys Val Ile Tyr Gly Ser Ser Ala Gly Phe
    1145              1150              1155

His Ala Val Asp Val Asp Ser Gly Asn Ser Tyr Asp Ile Tyr Ile
    1160              1165              1170

Pro Val His Ile Gln Ser Gln Ile Thr Pro His Ala Ile Ile Phe
1175              1180              1185

Leu Pro Asn Thr Asp Gly Met Glu Met Leu Leu Cys Tyr Glu Asp
    1190              1195              1200

Glu Gly Val Tyr Val Asn Thr Tyr Gly Arg Ile Ile Lys Asp Val
    1205              1210              1215

Val Leu Gln Trp Gly Glu Met Pro Thr Ser Val Ala Tyr Ile Cys
    1220              1225              1230

Ser Asn Gln Ile Met Gly Trp Gly Glu Lys Ala Ile Glu Ile Arg
    1235              1240              1245

Ser Val Glu Thr Gly His Leu Asp Gly Val Phe Met His Lys Arg
    1250              1255              1260

Ala Gln Arg Leu Lys Phe Leu Cys Glu Arg Asn Asp Lys Val Phe
    1265              1270              1275

Phe Ala Ser Val Arg Ser Gly Gly Ser Ser Gln Val Tyr Phe Met
    1280              1285              1290

Thr Leu Asn Arg Asn Cys Ile Met Asn Trp
    1295              1300

<210> SEQ ID NO 11
<211> LENGTH: 1295
<212> TYPE: PRT
<213> ORGANISM: Homo sapiens

<400> SEQUENCE: 11

Met Gly Asp Pro Ala Pro Ala Arg Ser Leu Asp Asp Ile Asp Leu Ser
1               5                   10                  15

Ala Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

Asn Asp Asp Gln Leu Trp Leu Val Met Glu Phe Cys Gly Ala Gly Ser
```

```
                   100                 105                 110
        Val Thr Asp Leu Val Lys Asn Thr Lys Gly Asn Ala Leu Lys Glu Asp
                       115                 120                 125

Cys Ile Ala Tyr Ile Cys Arg Glu Ile Leu Arg Gly Leu Ala His Leu
            130                 135                 140

His Ala His Lys Val Ile His Arg Asp Ile Lys Gly Gln Asn Val Leu
        145                 150                 155                 160

Leu Thr Glu Asn Ala Glu Val Lys Leu Val Asp Phe Gly Val Ser Ala
                        165                 170                 175

Gln Leu Asp Arg Thr Val Gly Arg Arg Asn Thr Phe Ile Gly Thr Pro
                    180                 185                 190

Tyr Trp Met Ala Pro Glu Val Ile Ala Cys Asp Glu Asn Pro Asp Ala
                    195                 200                 205

Thr Tyr Asp Tyr Arg Ser Asp Ile Trp Ser Leu Gly Ile Thr Ala Ile
            210                 215                 220

Glu Met Ala Glu Gly Ala Pro Pro Leu Cys Asp Met His Pro Met Arg
        225                 230                 235                 240

Ala Leu Phe Leu Ile Pro Arg Asn Pro Pro Pro Arg Leu Lys Ser Lys
                        245                 250                 255

Lys Trp Ser Lys Lys Phe Ile Asp Phe Ile Asp Thr Cys Leu Ile Lys
                    260                 265                 270

Thr Tyr Leu Ser Arg Pro Pro Thr Glu Gln Leu Leu Lys Phe Pro Phe
            275                 280                 285

Ile Arg Asp Gln Pro Thr Glu Arg Gln Val Arg Ile Gln Leu Lys Asp
            290                 295                 300

His Ile Asp Arg Ser Arg Lys Lys Arg Gly Glu Lys Glu Glu Thr Glu
        305                 310                 315                 320

Tyr Glu Tyr Ser Gly Ser Glu Glu Asp Asp Ser His Gly Glu Glu
                        325                 330                 335

Gly Glu Pro Ser Ser Ile Met Asn Val Pro Gly Glu Ser Thr Leu Arg
                    340                 345                 350

Arg Glu Phe Leu Arg Leu Gln Gln Glu Asn Lys Ser Asn Ser Glu Ala
                    355                 360                 365

Leu Lys Gln Gln Gln Gln Leu Gln Gln Gln Gln Arg Asp Pro Glu
        370                 375                 380

Ala His Ile Lys His Leu Leu His Gln Arg Gln Arg Arg Ile Glu Glu
        385                 390                 395                 400

Gln Lys Glu Glu Arg Arg Val Glu Glu Gln Arg Arg Glu Arg
                    405                 410                 415

Glu Gln Arg Lys Leu Gln Glu Lys Glu Gln Arg Arg Leu Glu Asp
                        420                 425                 430

Met Gln Ala Leu Arg Arg Glu Glu Arg Arg Gln Ala Glu Arg Glu
                    435                 440                 445

Gln Glu Tyr Lys Arg Lys Gln Leu Glu Glu Gln Arg Gln Ser Glu Arg
                    450                 455                 460

Leu Gln Arg Gln Leu Gln Gln Glu His Ala Tyr Leu Lys Ser Leu Gln
        465                 470                 475                 480

Gln Gln Gln Gln Gln Gln Leu Gln Lys Gln Gln Gln Gln Leu
                        485                 490                 495

Leu Pro Gly Asp Arg Lys Pro Leu Tyr His Tyr Gly Arg Gly Met Asn
                    500                 505                 510

Pro Ala Asp Lys Pro Ala Trp Ala Arg Glu Val Glu Glu Arg Thr Arg
                    515                 520                 525
```

-continued

```
Met Asn Lys Gln Gln Asn Ser Pro Leu Ala Lys Ser Lys Pro Gly Ser
            530                 535                 540

Thr Gly Pro Glu Pro Pro Ile Pro Gln Ala Ser Pro Gly Pro Pro Gly
545                 550                 555                 560

Pro Leu Ser Gln Thr Pro Pro Met Gln Arg Pro Val Glu Pro Gln Glu
                565                 570                 575

Gly Pro His Lys Ser Leu Val Ala His Arg Val Pro Leu Lys Pro Tyr
            580                 585                 590

Ala Ala Pro Val Pro Arg Ser Gln Ser Leu Gln Asp Gln Pro Thr Arg
            595                 600                 605

Asn Leu Ala Ala Phe Pro Ala Ser His Asp Pro Asp Pro Ala Ile Pro
            610                 615                 620

Ala Pro Thr Ala Thr Pro Ser Ala Arg Gly Ala Val Ile Arg Gln Asn
625                 630                 635                 640

Ser Asp Pro Thr Ser Glu Gly Pro Gly Pro Ser Pro Asn Pro Pro Ala
                645                 650                 655

Trp Val Arg Pro Asp Asn Glu Ala Pro Pro Lys Val Pro Gln Arg Thr
            660                 665                 670

Ser Ser Ile Ala Thr Ala Leu Asn Thr Ser Gly Ala Gly Gly Ser Arg
            675                 680                 685

Pro Ala Gln Ala Val Arg Ala Ser Asn Pro Asp Leu Arg Arg Ser Asp
            690                 695                 700

Pro Gly Trp Glu Arg Ser Asp Ser Val Leu Pro Ala Ser His Gly His
705                 710                 715                 720

Leu Pro Gln Ala Gly Ser Leu Glu Arg Asn Arg Val Gly Val Ser Ser
                725                 730                 735

Lys Pro Asp Ser Ser Pro Val Leu Ser Pro Gly Asn Lys Ala Lys Pro
            740                 745                 750

Asp Asp His Arg Ser Arg Pro Gly Arg Pro Ala Asp Phe Val Leu Leu
            755                 760                 765

Lys Glu Arg Thr Leu Asp Glu Ala Pro Arg Pro Lys Lys Ala Met
            770                 775                 780

Asp Tyr Ser Ser Ser Glu Glu Val Glu Ser Ser Glu Asp Asp Glu
785                 790                 795                 800

Glu Glu Gly Glu Gly Gly Pro Ala Glu Gly Ser Arg Asp Thr Pro Gly
                805                 810                 815

Gly Arg Ser Asp Gly Asp Thr Asp Ser Val Ser Thr Met Val Val His
            820                 825                 830

Asp Val Glu Glu Ile Thr Gly Thr Gln Pro Pro Tyr Gly Gly Gly Thr
            835                 840                 845

Met Val Val Gln Arg Thr Pro Glu Glu Glu Arg Asn Leu Leu His Ala
850                 855                 860

Asp Ser Asn Gly Tyr Thr Asn Leu Pro Asp Val Val Gln Pro Ser His
865                 870                 875                 880

Ser Pro Thr Glu Asn Ser Lys Gly Gln Ser Pro Pro Ser Lys Asp Gly
                885                 890                 895

Ser Gly Asp Tyr Gln Ser Arg Gly Leu Val Lys Ala Pro Gly Lys Ser
            900                 905                 910

Ser Phe Thr Met Phe Val Asp Leu Gly Ile Tyr Gln Pro Gly Gly Ser
            915                 920                 925

Gly Asp Ser Ile Pro Ile Thr Ala Leu Val Gly Gly Glu Gly Thr Arg
            930                 935                 940

Leu Asp Gln Leu Gln Tyr Asp Val Arg Lys Gly Ser Val Val Asn Val
945                 950                 955                 960
```

```
Asn Pro Thr Asn Thr Arg Ala His Ser Glu Thr Pro Glu Ile Arg Lys
            965                 970                 975

Tyr Lys Lys Arg Phe Asn Ser Glu Ile Leu Cys Ala Ala Leu Trp Gly
            980                 985                 990

Val Asn Leu Leu Val Gly Thr Glu Asn Gly Leu Met Leu Leu Asp Arg
            995                1000                1005

Ser Gly Gln Gly Lys Val Tyr Gly Leu Ile Gly Arg Arg Arg Phe
           1010                1015            1020

Gln Gln Met Asp Val Leu Glu Gly Leu Asn Leu Leu Ile Thr Ile
           1025                1030            1035

Ser Gly Lys Arg Asn Lys Leu Arg Val Tyr Tyr Leu Ser Trp Leu
           1040                1045            1050

Arg Asn Lys Ile Leu His Asn Asp Pro Glu Val Glu Lys Lys Gln
           1055                1060            1065

Gly Trp Thr Thr Val Gly Asp Met Glu Gly Cys Gly His Tyr Arg
           1070                1075            1080

Val Val Lys Tyr Glu Arg Ile Lys Phe Leu Val Ile Ala Leu Lys
           1085                1090            1095

Ser Ser Val Glu Val Tyr Ala Trp Ala Pro Lys Pro Tyr His Lys
           1100                1105            1110

Phe Met Ala Phe Lys Ser Phe Ala Asp Leu Pro His Arg Pro Leu
           1115                1120            1125

Leu Val Asp Leu Thr Val Glu Glu Gly Gln Arg Leu Lys Val Ile
           1130                1135            1140

Tyr Gly Ser Ser Ala Gly Phe His Ala Val Asp Val Asp Ser Gly
           1145                1150            1155

Asn Ser Tyr Asp Ile Tyr Ile Pro Val His Ile Gln Ser Gln Ile
           1160                1165            1170

Thr Pro His Ala Ile Ile Phe Leu Pro Asn Thr Asp Gly Met Glu
           1175                1180            1185

Met Leu Leu Cys Tyr Glu Asp Glu Gly Val Tyr Val Asn Thr Tyr
           1190                1195            1200

Gly Arg Ile Ile Lys Asp Val Val Leu Gln Trp Gly Glu Met Pro
           1205                1210            1215

Thr Ser Val Ala Tyr Ile Cys Ser Asn Gln Ile Met Gly Trp Gly
           1220                1225            1230

Glu Lys Ala Ile Glu Ile Arg Ser Val Glu Thr Gly His Leu Asp
           1235                1240            1245

Gly Val Phe Met His Lys Arg Ala Gln Arg Leu Lys Phe Leu Cys
           1250                1255            1260

Glu Arg Asn Asp Lys Val Phe Phe Ala Ser Val Arg Ser Gly Gly
           1265                1270            1275

Ser Ser Gln Val Tyr Phe Met Thr Leu Asn Arg Asn Cys Ile Met
           1280                1285            1290

Asn Trp
       1295
```